US012487524B2

(12) United States Patent
Hatakeyama

(10) Patent No.: US 12,487,524 B2
(45) Date of Patent: Dec. 2, 2025

(54) RESIST MATERIAL AND PATTERNING PROCESS

(71) Applicant: SHIN-ETSU CHEMICAL CO., LTD., Tokyo (JP)

(72) Inventor: Jun Hatakeyama, Joetsu (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 741 days.

(21) Appl. No.: 17/834,319

(22) Filed: Jun. 7, 2022

(65) Prior Publication Data

US 2023/0022129 A1 Jan. 26, 2023

(30) Foreign Application Priority Data

Jun. 22, 2021 (JP) ................................ 2021-102932

(51) Int. Cl.
*G03F 7/004* (2006.01)
*C07C 381/12* (2006.01)
*C07D 207/448* (2006.01)
*G03F 7/06* (2006.01)

(52) U.S. Cl.
CPC .......... *G03F 7/0045* (2013.01); *C07C 381/12* (2013.01); *C07D 207/448* (2013.01); *G03F 7/004* (2013.01); *G03F 7/066* (2013.01)

(58) Field of Classification Search
None
See application file for complete search history.

(56) References Cited

U.S. PATENT DOCUMENTS

2006/0228648 A1 10/2006 Ohsawa et al.
2007/0231708 A1 10/2007 Matsumaru et al.
2007/0231738 A1 10/2007 Kaneko et al.
2008/0044738 A1 2/2008 Harada et al.
2008/0085469 A1 4/2008 Ohsawa et al.
2008/0090172 A1 4/2008 Hatakeyama et al.
2008/0118860 A1 5/2008 Harada et al.
2008/0153030 A1 6/2008 Kobayashi et al.
2008/0241736 A1 10/2008 Kobayashi et al.
2009/0246694 A1 10/2009 Ohsawa et al.
2010/0035185 A1 2/2010 Hagiwara et al.
2010/0209827 A1 8/2010 Ohashi et al.
2011/0159433 A1* 6/2011 Takahashi ............ C08F 212/20 526/287
2012/0045724 A1 2/2012 Ohsawa et al.
2012/0100486 A1 4/2012 Sagehashi et al.
2013/0084529 A1 4/2013 Hatakeyama et al.
2013/0089820 A1 4/2013 Hatakeyama et al.
2014/0199629 A1 7/2014 Ohashi et al.
2015/0301449 A1 10/2015 Ohashi et al.
2017/0010532 A1* 1/2017 Iimori ........................ G03F 7/20
2018/0180998 A1* 6/2018 Kotake ................. G03F 7/2053
2019/0094698 A1* 3/2019 Carcasi ................. G03F 7/2022

FOREIGN PATENT DOCUMENTS

JP 2006-045311 A 2/2006
JP 3790649 B2 6/2006
JP 2006-178317 A 7/2006
JP 2007-145797 A 6/2007
JP 2007-297590 A 11/2007
JP 2008-013551 A 1/2008
JP 2008-106045 A 5/2008
JP 2008-111103 A 5/2008
JP 2008-122932 A 5/2008
JP 2008-158339 A 7/2008
JP 2008-239918 A 10/2008
JP 2009-007327 A 1/2009
JP 2009-258695 A 11/2009
JP 2010-215608 A 9/2010
JP 2012-041320 A 3/2012
JP 2012-106986 A 6/2012
JP 2012-153644 A 8/2012
JP 2013-080033 A 5/2013
JP 2013-083821 A 5/2013
JP 2014-133723 A 7/2014
JP 2015-206932 A 11/2015
WO 2011/048919 A1 4/2011

OTHER PUBLICATIONS

Kishikawa et al., "Assessment of trade-off between resist resolution and sensitivity for optimization of hyper-NA immersion lithography," Optical Microlithography XX, Proc. of SPIE vol. 6520, 2007, pp. 65203L-1-65203L-9.
Okazaki, Eiichi, "Analysis of UV curing behavior of maleimide compounds using Raman spectroscopy," Toagosei Annual Report, TREND, 2002, No. 5, pp. 11-15.

* cited by examiner

*Primary Examiner* — Mark F. Huff
*Assistant Examiner* — Kevin J Drummey
(74) *Attorney, Agent, or Firm* — Oliff PLC

(57) ABSTRACT

The present invention is a resist material containing a quencher, where the quencher contains a sulfonium salt of a carboxylic acid bonded to a maleimide group. In a chemically amplified resist material in which an acid is used as a catalyst, it is desired to develop a quencher that makes it possible to reduce LWR of line patterns and critical dimension uniformity (CDU) of hole patterns, and to improve sensitivity. For this purpose, it is necessary to reduce image blurs due to acid diffusion considerably. An object of the present invention is to provide: a resist material having high sensitivity, low LWR, and low CDU in both a positive resist material and a negative resist material; and a patterning process using the same.

20 Claims, No Drawings

RESIST MATERIAL AND PATTERNING PROCESS

TECHNICAL FIELD

The present invention relates to: a resist material; and a patterning process.

BACKGROUND ART

As LSIs advance toward higher integration and higher processing speed, miniaturization of pattern rule is progressing rapidly. This is because the spread of high-speed communication of 5 G and artificial intelligence (AI) has progressed, and high-performance devices for processing these are needed. As a cutting-edge technology for miniaturization, 5-nm node devices have been mass-produced by extreme ultraviolet ray (EUV) lithography at a wavelength of 13.5 nm. Furthermore, studies are also in progress on employing EUV lithography in next-generation 3-nm node and the following-generation 2-nm node devices.

As the miniaturization progresses, image blurs due to acid diffusion become a problem. To ensure resolution for fine patterns with dimensional sizes of 45 nm and smaller, there is a proposal that it is important to not only improve dissolution contrast as previously reported, but also control acid diffusion (Non Patent Document 1). Nevertheless, since chemically amplified resist materials enhance the sensitivity and contrast through acid diffusion, an attempt to minimize acid diffusion by reducing the temperature and/or time of post-exposure bake (PEB) results in significant reductions of sensitivity and contrast.

A triangular tradeoff relationship among sensitivity, resolution, and edge roughness has been pointed out. Specifically, resolution improvement requires suppression of acid diffusion, whereas shortening acid diffusion distance lowers sensitivity.

The addition of an acid generator capable of generating a bulky acid is effective in suppressing acid diffusion. Hence, it has been proposed to incorporate in a polymer a repeating unit derived from an onium salt having a polymerizable unsaturated bond. In this case, the polymer also functions as an acid generator (polymer-bound acid generator). Patent Document 1 proposes a sulfonium and iodonium salt having a polymerizable unsaturated bond that generates a particular sulfonic acid. Patent Document 2 proposes a sulfonium salt having a sulfonate acid moiety directly bonded to the main chain.

In an acid-labile group used for a (meth)acrylate polymer for an ArF resist material, a deprotection reaction progresses by the use of a photo-acid generator that generates a sulfonic acid having fluorine substituted at α position. However, a deprotection reaction does not progress when using an acid generator that generates a sulfonic acid not having fluorine substituted at α position or generates carboxylic acid. When a sulfonium salt or iodonium salt that generates a sulfonic acid having fluorine substituted at α position is mixed with a sulfonium salt or iodonium salt that generates a sulfonic acid not having fluorine substituted at α position, the sulfonium salt or iodonium salt that generates the sulfonic acid not having fluorine substituted at α position undergoes ion exchange with the sulfonic acid having fluorine substituted at α position. A sulfonic acid having fluorine substituted at α position generated by light returns to being a sulfonium salt or iodonium salt by ion exchange. Therefore, a sulfonium salt or iodonium salt of a sulfonic acid not having fluorine substituted at α position or of carboxylic acid functions as a quencher. A resist composition in which a sulfonium salt or iodonium salt that generates carboxylic acid is used as a quencher is proposed (Patent Document 3).

An acid generator of a bissulfonium salt, having two sulfonium salts in one molecule, is proposed (Patent Documents 3 to 5). An acid that is generated from a bissulfonium salt has a short diffusion, and is favorable. However, bissulfonium salt has poor solubility to resist solvents, and therefore, easily coheres. Thus, bissulfonium salt potentially has a fault that pattern defects and edge roughness (LWR) become large.

Photoreaction of a maleimide compound is reported (Non Patent Document 2). Here, it is shown that a compound having a substituent on a double bond of a maleimide group undergoes a dimerization reaction and a maleimide compound not having a substituent undergoes polymerization as well as a dimerization reaction. In addition, the generation of radicals from maleimide and the polymerization of an acrylate thereby is described.

CITATION LIST

Patent Literature

Patent Document 1: JP 2006-045311 A
Patent Document 2: JP 2006-178317 A
Patent Document 3: JP 2015-206932 A
Patent Document 4: JP 2008-013551 A
Patent Document 5: WO 2011/048919

Non Patent Literature

Non Patent Document 1: SPIE Vol. 6520 65203L-1 (2007)
Non Patent Document 2: Toagosei Kenkyu Nenpo (Toagosei Annual Report) TREND, 2002, issue 5, p. 11

SUMMARY OF INVENTION

Technical Problem

In a chemically amplified resist material in which an acid is used as a catalyst, it is desired to develop a quencher that makes it possible to reduce LWR of line patterns and critical dimension uniformity (CDU) of hole patterns, and to improve sensitivity. For this purpose, it is necessary to reduce image blurs due to acid diffusion considerably.

The present invention has been made in view of the above circumstances, and an object thereof is to provide: a resist material having high sensitivity and low CDU in both a positive resist material and a negative resist material; and a patterning process using the same.

Solution to Problem

To achieve the object, the present invention provides a resist material comprising a quencher, wherein the quencher contains a sulfonium salt of a carboxylic acid bonded to a maleimide group.

When such a quencher is contained, LWR of line patterns and CDU of hole patterns can be reduced, and in addition, sensitivity can also be enhanced.

The sulfonium salt of the carboxylic acid bonded to the maleimide group is preferably represented by the following general formula (1), (1)

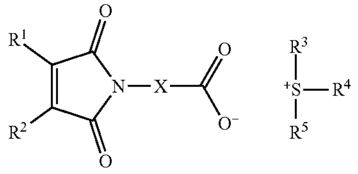

wherein $R^1$ and $R^2$ each represent a hydrogen atom or a linear, branched, or cyclic alkyl group having 1 to 10 carbon atoms, $R^1$ and $R^2$ optionally being bonded to each other to form a ring; X represents a single bond or a divalent linking group having 1 to 20 carbon atoms and optionally contains an ether group, a carbonyl group, an ester group, an amide group, a sultone group, a lactam group, a carbonate group, a halogen atom, a hydroxy group, or a carboxy group; $R^3$ to $R^5$ each independently represent a monovalent hydrocarbon group having 1 to 25 carbon atoms and optionally containing a heteroatom; and any two of $R^3$, $R^4$, and $R^5$ are optionally bonded with each other to form a ring with a sulfur atom that is bonded thereto.

When a quencher having such a structure is used, LWR of line patterns and CDU of hole patterns can be reduced more certainly, and moreover, sensitivity can also be improved.

The resist material preferably further comprises one or more selected from an acid generator for generating an acid, an organic solvent, and a surfactant.

Such a resist material is more excellent.

The acid generator preferably generates a sulfonic acid, imide acid, or methide acid.

When such an acid generator is used, it is possible to make the sulfonium salt of the carboxylic acid bonded to the maleimide group function as a quencher more certainly.

The resist material preferably further comprises a base polymer.

The base polymer preferably further contains at least one repeating unit selected from repeating units represented by the following general formulae (f1) to (f3), (f1)

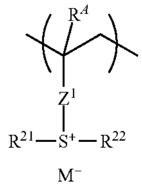

(f2)

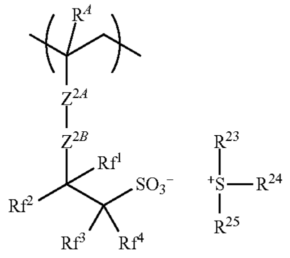

-continued (f3)

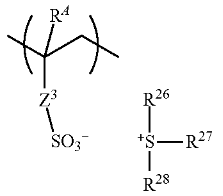

wherein each $R^A$ independently represents a hydrogen atom or a methyl group; $Z^1$ represents a single bond, a phenylene group, a naphthylene group, $-Z^{11}-$, $-O-Z^{11}-$, $-C(=O)-O-Z^{11}-$, or $-C(=O)-NH-Z^{11}-$; $Z^{11}$ represents an alkanediyl group having 1 to 6 carbon atoms, an alkenediyl group having 2 to 6 carbon atoms, or a hydrocarbon group having 1 to 20 carbon atoms and optionally containing a phenylene group and optionally contains a carbonyl group, an ester bond, an ether bond, or a hydroxy group; $Z^{2A}$ represents a single bond or an ester bond; $Z^{2B}$ represents a single bond or a divalent group having 1 to 18 carbon atoms and optionally contains an ester bond, an ether bond, a lactone ring, a bromine atom, or an iodine atom; $Z^3$ represents a single bond, a methylene group, an ethylene group, a phenylene group, a fluorinated phenylene group, a phenylene group substituted with a trifluoromethyl group, $-Z^{31}-$, $-O-Z^{31}-$, $-C(=O)-O-Z^{31}-$, or $-C(=O)-NH-$ $Z^{31}-$; $Z^{31}$ represents an alkanediyl group having 1 to 15 carbon atoms, an alkenediyl group having 2 to 15 carbon atoms, or a group containing a phenylene group and optionally contains a carbonyl group, an ester bond, an ether bond, a halogen atom, or a hydroxy group; $Rf^1$ to $Rf^4$ each independently represent a hydrogen atom, a fluorine atom, an oxygen atom, or a trifluoromethyl group, provided that at least one is a fluorine atom, and that when $Rf^1$ and $Rf^2$ are respectively an oxygen atom, $Rf^1$ and $Rf^2$ are a single oxygen atom bonded to a single carbon atom to form a carbonyl group; $R^{21}$ to $R^{28}$ each independently represent a monovalent hydrocarbon group having 1 to 25 carbon atoms and optionally containing a heteroatom; any two of $R^{23}$, $R^{24}$, and $R^{25}$ or any two of $R^{26}$, $R^{27}$, and $R^{28}$ are optionally bonded with each other to form a ring with a sulfur atom that is bonded thereto; and $M^-$ represents a non-nucleophilic counter ion.

When the base polymer contains such a repeating unit, the repeating unit can function as an acid generator.

Furthermore, the base polymer preferably contains a repeating unit represented by the following general formula (a1) or a repeating unit represented by the following formula (a2) as a repeating unit having an acid-labile group, (a1)

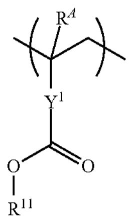

-continued (a2)

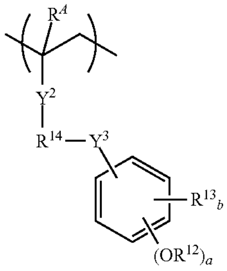

wherein each $R^A$ independently represents a hydrogen atom or a methyl group; $R^{11}$ and $R^{12}$ each represent an acid-labile group; $Y^1$ represents a single bond or a linking group having 1 to 12 carbon atoms containing at least one selected from a phenylene group, a naphthylene group, an ester bond, and a lactone ring; $Y^2$ represents a single bond, an ester bond, or an amide bond; $Y^3$ represents a single bond, an ether bond, or an ester bond; $R^{13}$ represents a fluorine atom, a trifluoromethyl group, a cyano group, or a saturated hydrocarbyl group having 1 to 6 carbon atoms; $R^{14}$ represents a single bond or an alkanediyl group having 1 to 6 carbon atoms, and some of the carbon atoms are optionally substituted with an ether bond or an ester bond; and "a" represents 1 or 2 and "b" represents an integer of 0 to 4, provided that $1 \leq a+b \leq 5$.

When the base polymer contains a repeating unit having an acid-labile group, the resist material is preferably a chemically amplified positive resist material.

When the base polymer contains a repeating unit having an acid-labile group as described, the resist material functions excellently as a positive resist material.

The base polymer preferably does not contain an acid-labile group.

When the base polymer does not contain a repeating unit having an acid-labile group, the resist material is preferably a chemically amplified negative resist material.

When the base polymer does not contain a repeating unit having an acid-labile group as described, the resist material functions excellently as a negative resist material.

In addition, the present invention provides a patterning process comprising the steps of:

(1) forming a resist film on a substrate by using the above-described resist material;
(2) exposing the resist film to a high-energy beam; and
(3) developing the exposed resist film by using a developer.

According to such a patterning process, the target pattern can be formed excellently.

After the step (1) and before the step (2), (1') an entire surface of the resist film is preferably exposed to light having a wavelength at which the sulfonium salt of the carboxylic acid bonded to the maleimide group does not decompose.

The wavelength at which the sulfonium salt does not decompose is preferably longer than a wavelength of 300 nm.

When the entire surface of the resist film is exposed to such light, the diffusion of acid can be further prevented by the maleimide group undergoing polymerization and/or coupling.

The high-energy beam is preferably a KrF excimer laser beam, an ArF excimer laser beam, an electron beam, or an extreme ultraviolet ray having a wavelength of 3 to 15 nm.

When such a high-energy beam is used, the target pattern can be formed excellently.

Advantageous Effects of Invention

The above-described sulfonium salt of the carboxylic acid bonded to the maleimide group is a quencher for suppressing acid diffusion. This provides properties of low acid diffusion, so that LWR and CDU can be reduced and sensitivity can also be improved. This makes it possible to construct a resist material having low LWR, low CDU, and high sensitivity.

DESCRIPTION OF EMBODIMENTS

It has been desired to develop a quencher that makes it possible to reduce LWR in line patterns and critical dimension uniformity (CDU) in hole patterns and to enhance sensitivity in a chemically amplified resist material in which an acid is a catalyst.

To achieve the object, the present inventor has earnestly studied and found out that a resist material in which a sulfonium salt of a carboxylic acid bonded to a maleimide group is contained is a quencher for suppressing acid diffusion, and that an increase in molecular weight owing to a coupling reaction caused by light-irradiation of the maleimide group has a high effect of suppressing acid diffusion. The present inventor has thus found out that low acid diffusion makes it possible to obtain a resist material having little LWR, little CDU, excellent resolution, and a wide process margin. Thus, the present invention has been completed.

That is, the present invention is a resist material comprising a quencher, wherein the quencher contains a sulfonium salt of a carboxylic acid bonded to a maleimide group.

Hereinafter, the present invention will be described, but the present invention is not limited thereto.

[Resist Material]

The inventive resist material contains a quencher which is a sulfonium salt of a carboxylic acid bonded to a maleimide group.

[Sulfonium Salt of Carboxylic Acid Bonded to Maleimide Group]

The sulfonium salt of the carboxylic acid bonded to the maleimide group is preferably represented by the following general formula (1).

(1)

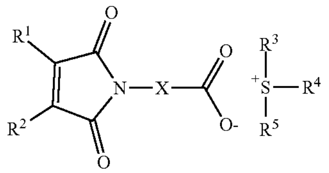

In the formula, $R^1$ and $R^2$ each represent a hydrogen atom or a linear, branched, or cyclic alkyl group having 1 to 10 carbon atoms, $R^1$ and $R^2$ optionally being bonded to each other to form a ring. X represents a single bond or a divalent linking group having 1 to 20 carbon atoms and optionally contains an ether group, a carbonyl group, an ester group, an amide group, a sultone group, a lactam group, a carbonate group, a halogen atom, a hydroxy group, or a carboxy group. $R^3$ to $R^5$ each independently represent a monovalent hydrocarbon group having 1 to 25 carbon atoms and optionally containing a heteroatom. In addition, any two of $R^3$, $R^4$, and $R^5$ are optionally bonded with each other to form a ring with a sulfur atom that is bonded thereto.
Examples of the carboxylic acid anion bonded to the maleimide group shown in the general formula (1) include those given below, but are not limited thereto.
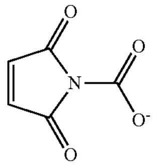
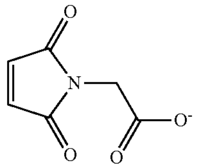
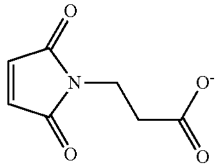
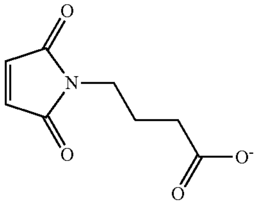
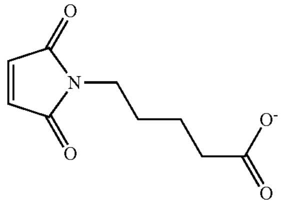
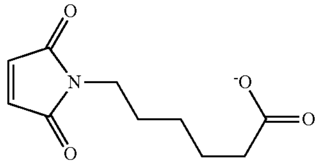
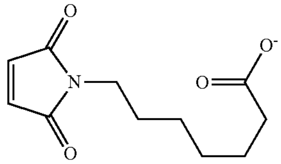
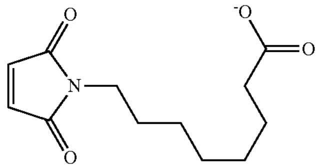
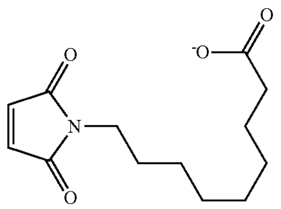
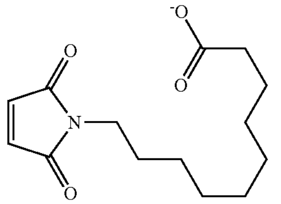
-continued
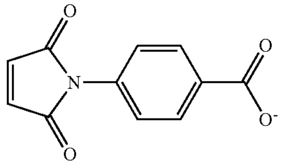
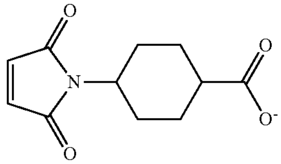
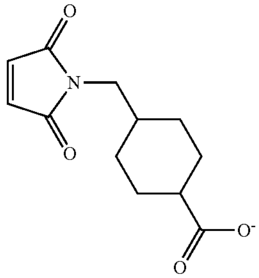
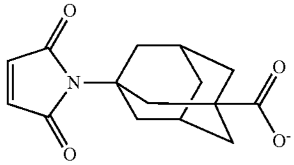
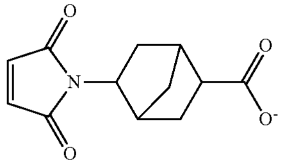
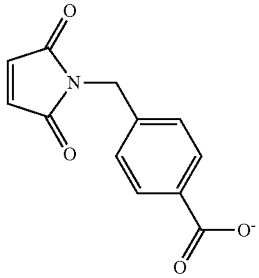
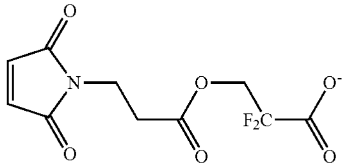
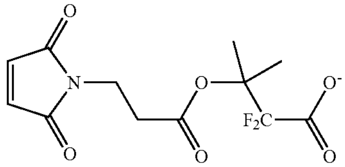
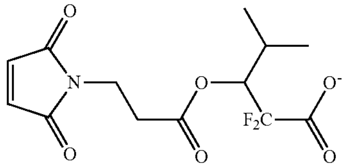

-continued
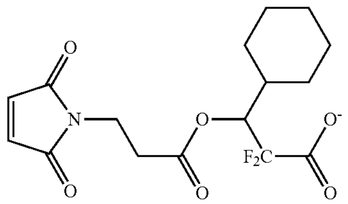
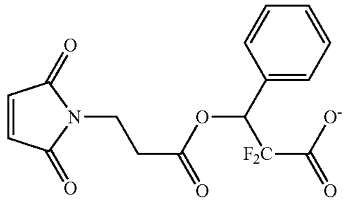
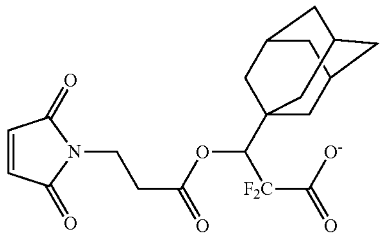
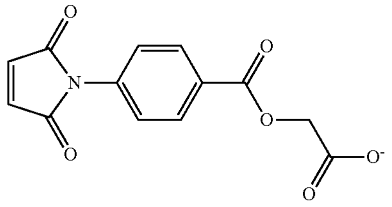
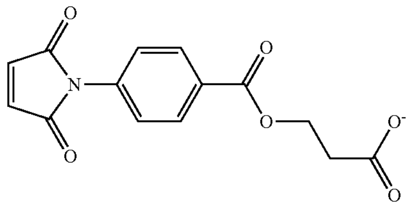
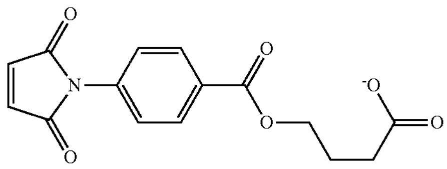
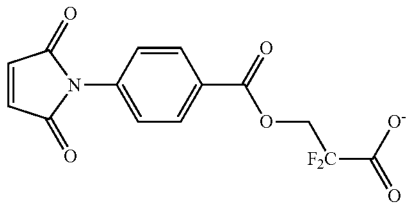
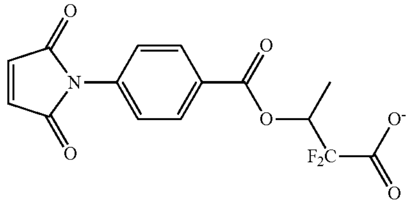
-continued
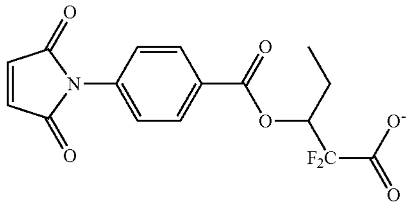
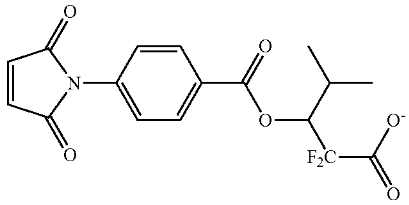
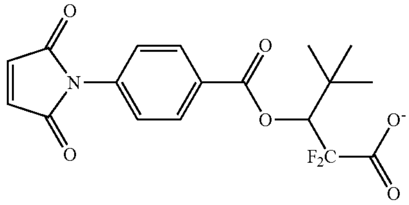
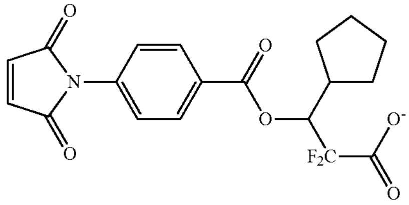
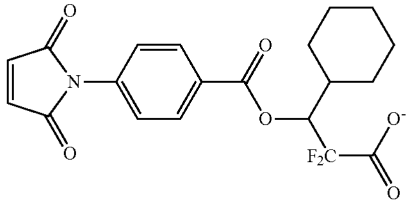
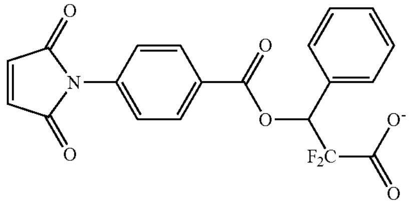
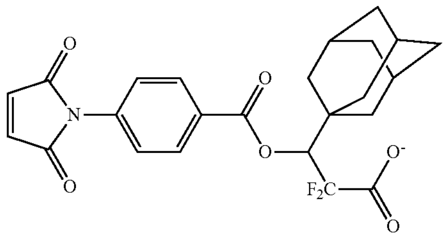
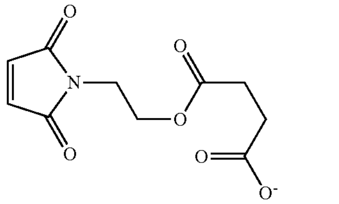

-continued
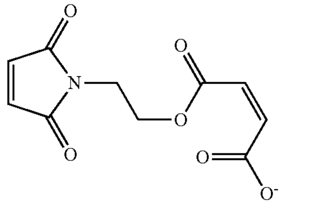
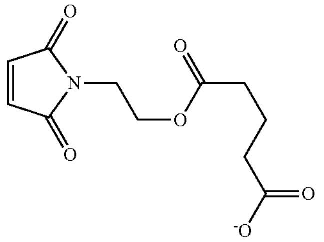
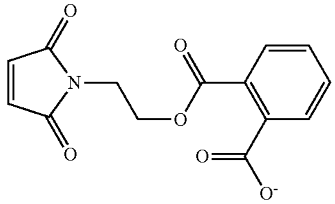
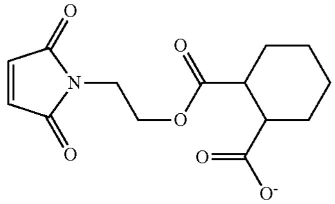
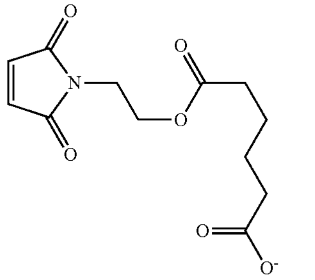
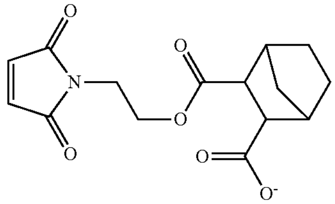
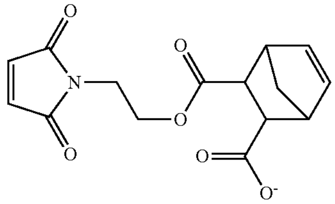
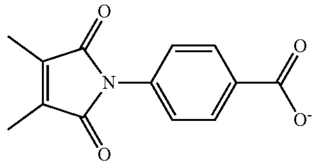
-continued
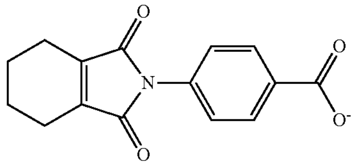
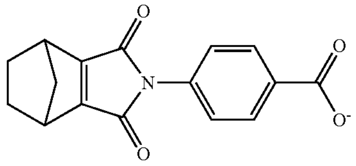
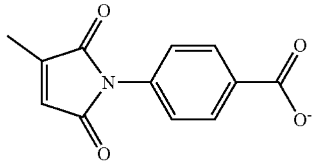
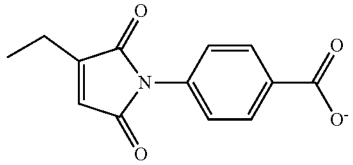
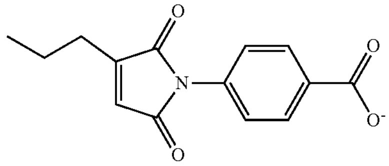
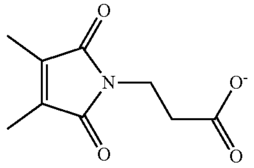
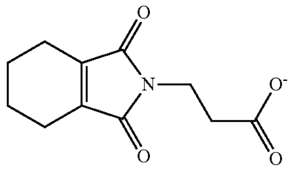
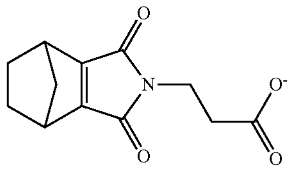
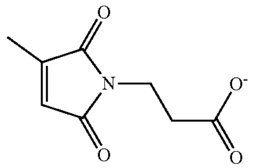
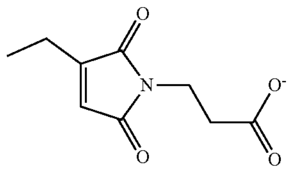

-continued
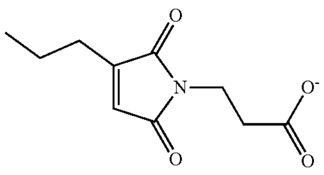
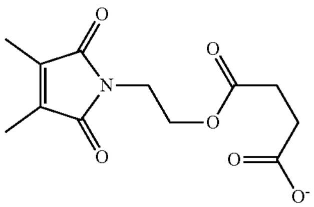
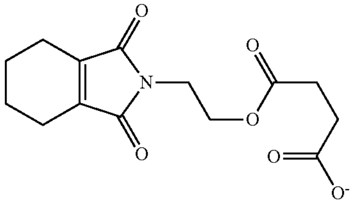
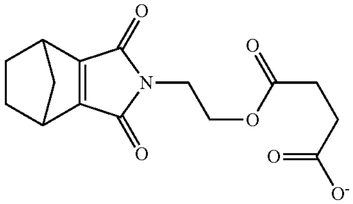
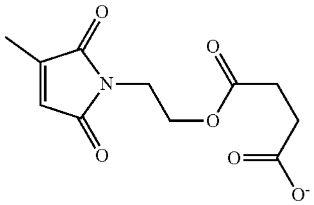
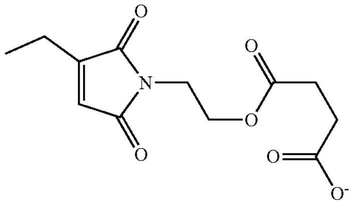
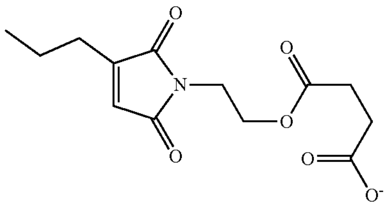
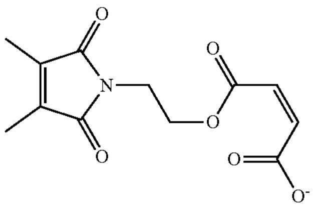
-continued
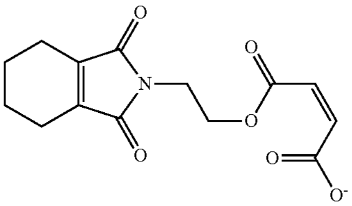
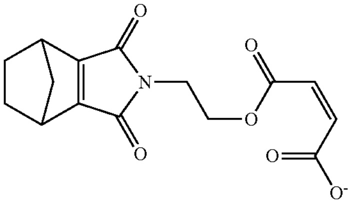
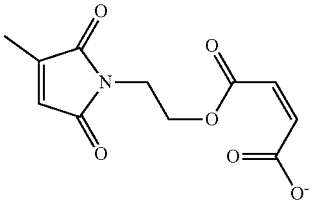
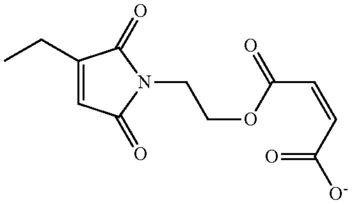
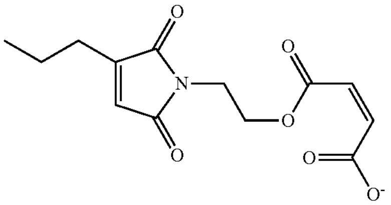
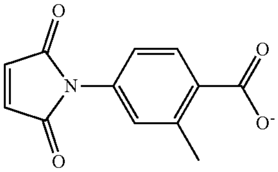
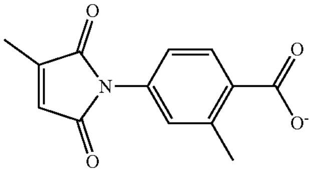
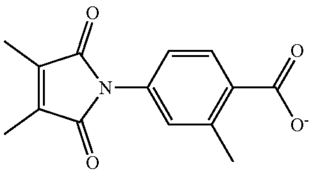
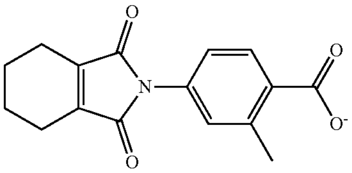

-continued
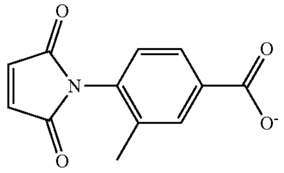
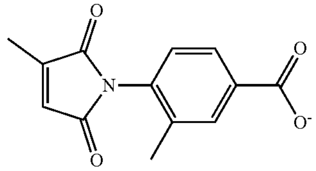
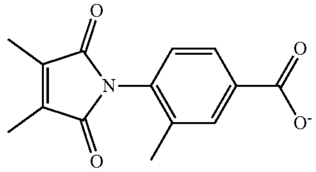
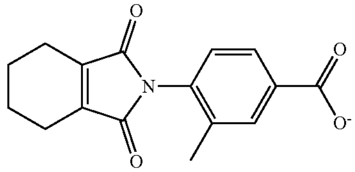
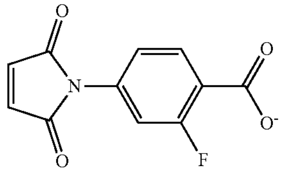
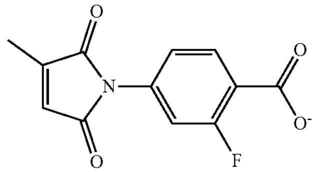
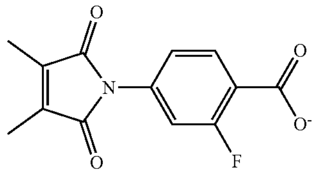
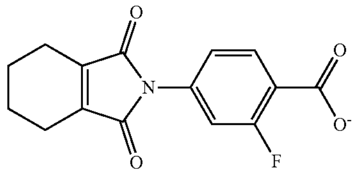
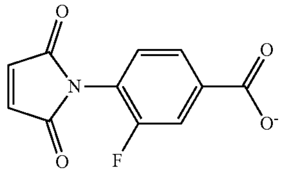
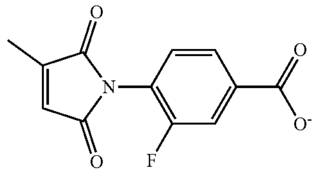
-continued
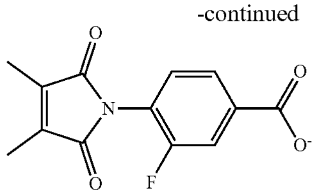
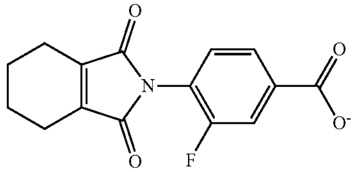
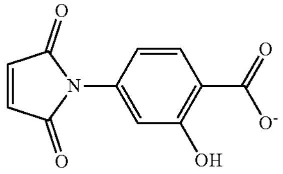
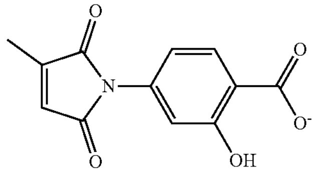
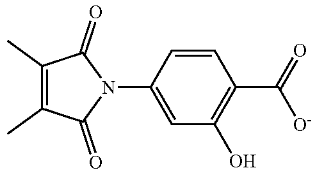
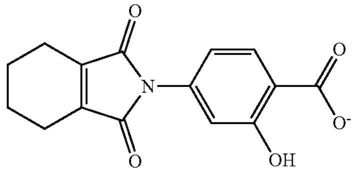
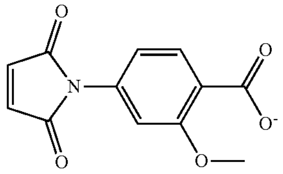
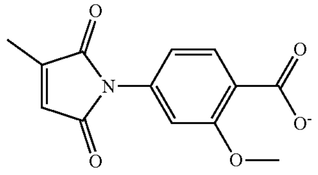
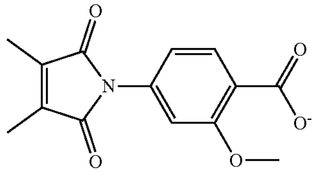
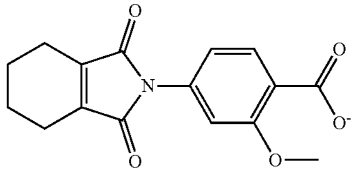

-continued
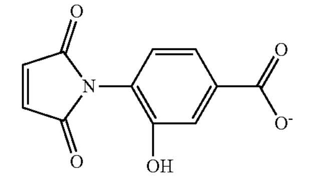
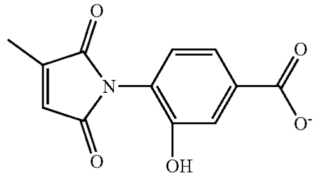
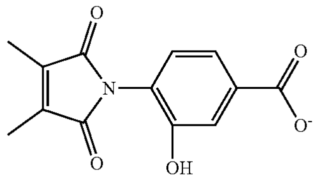
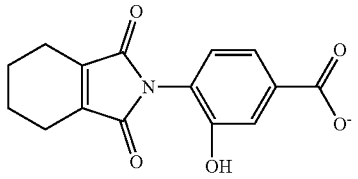
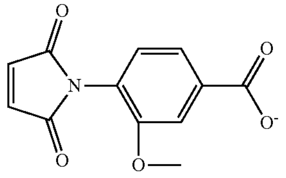
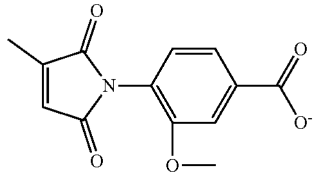
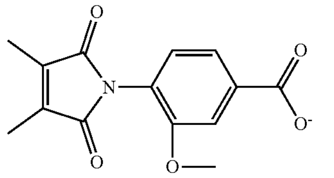
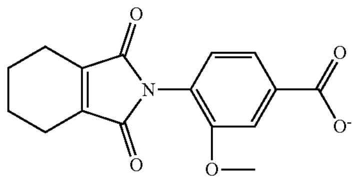
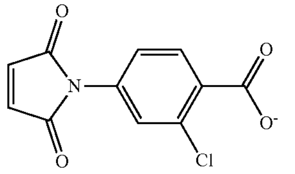
-continued
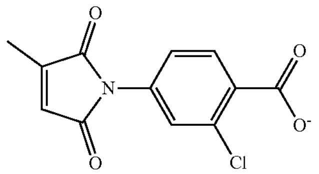
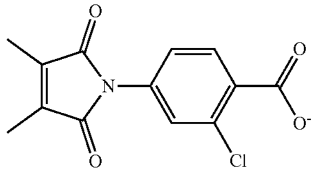
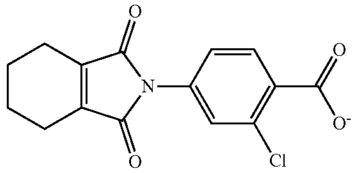
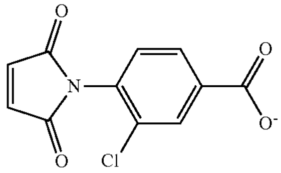
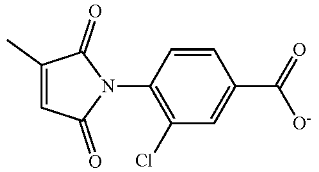
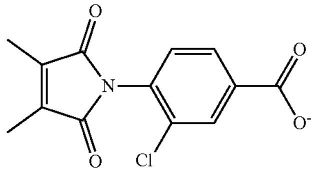
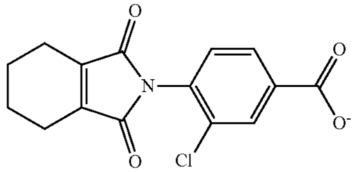
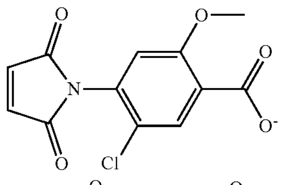
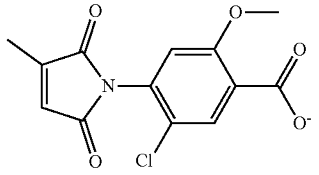
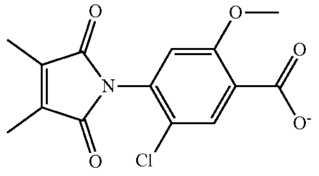

-continued
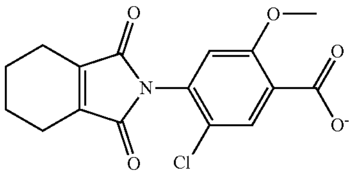
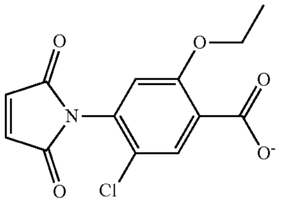
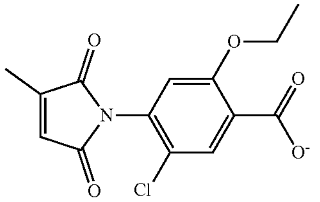
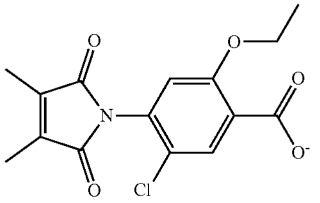
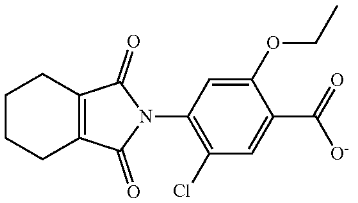
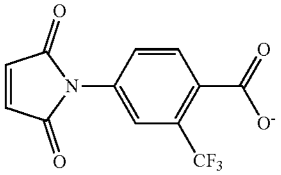
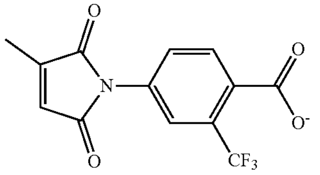
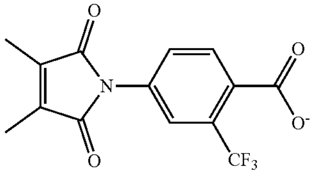
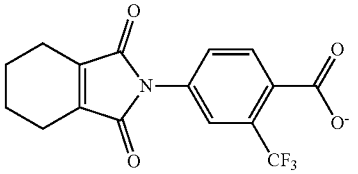
-continued
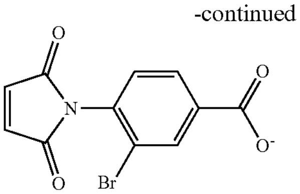
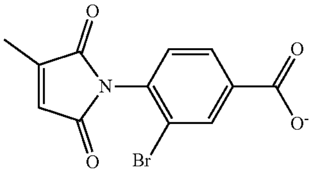
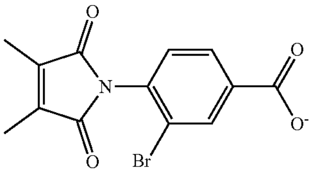
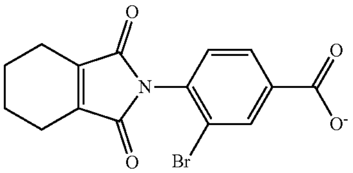
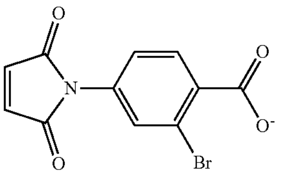
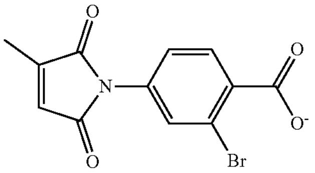
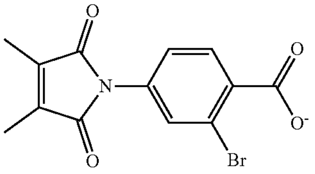
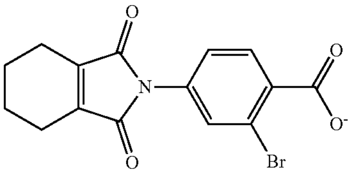
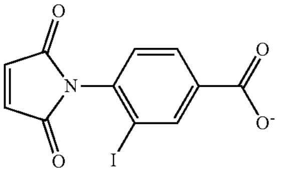
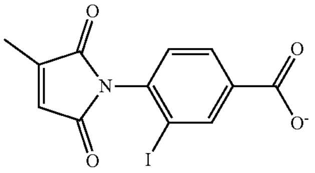

-continued
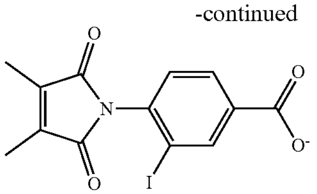
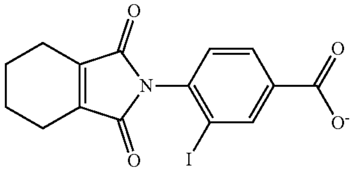
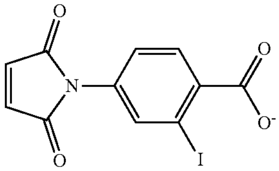
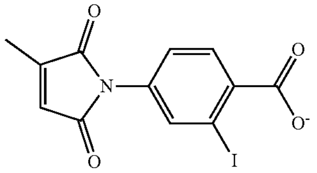
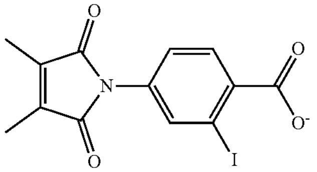
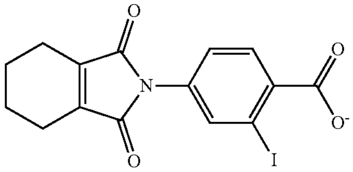
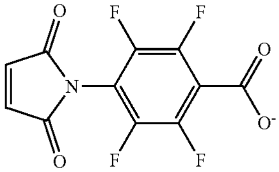
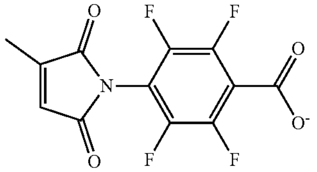
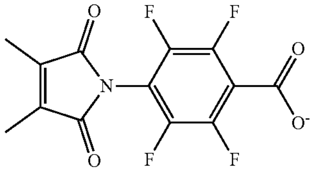
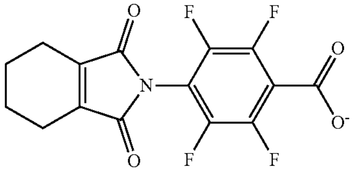
-continued
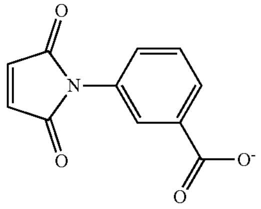
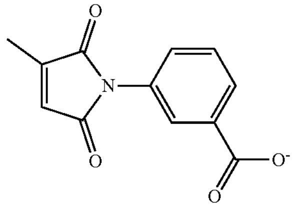
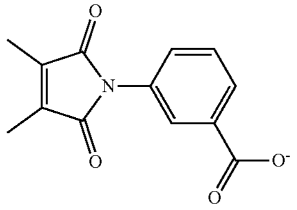
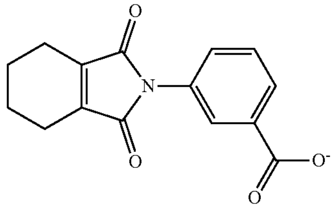
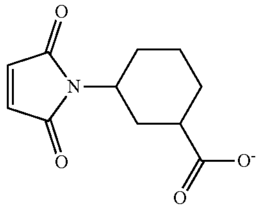
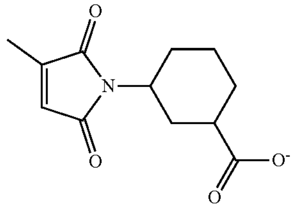
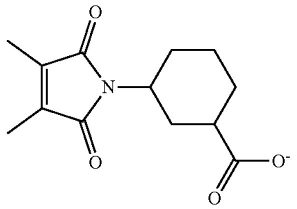
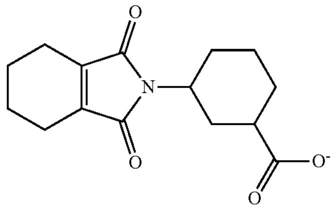

-continued
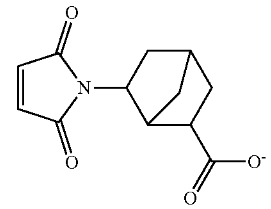
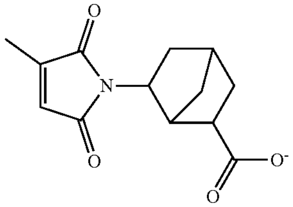
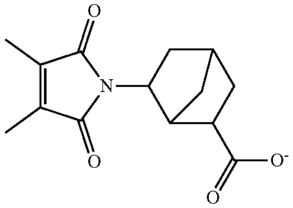
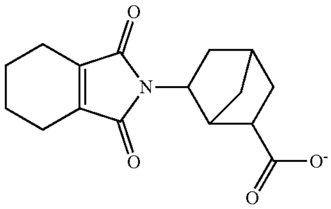
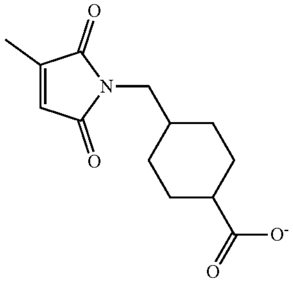
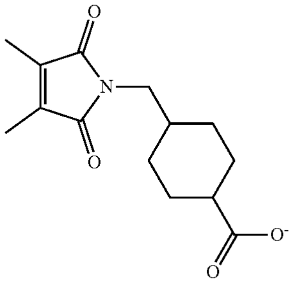
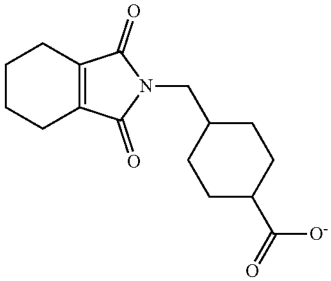
-continued
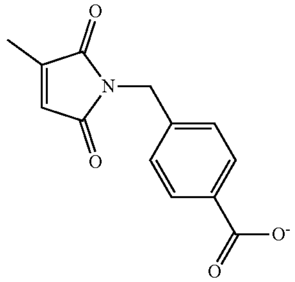
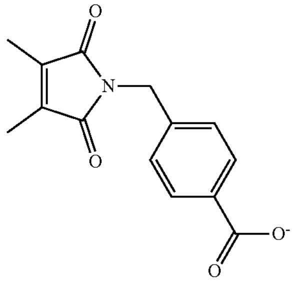
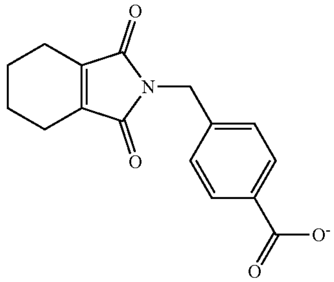
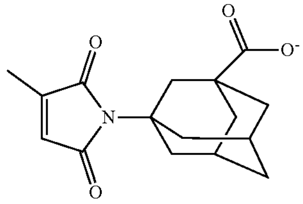
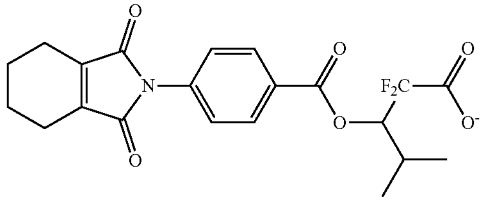
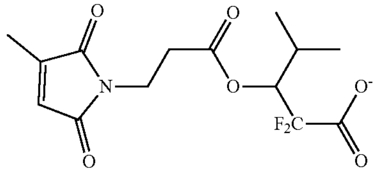
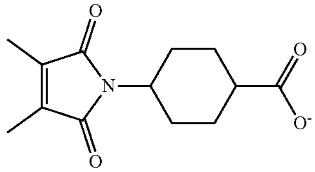

-continued
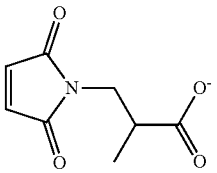
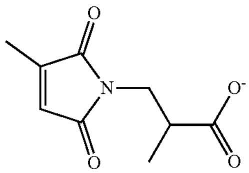
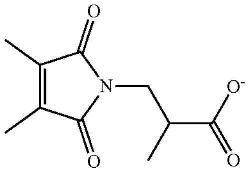
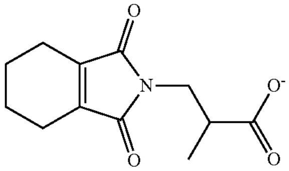
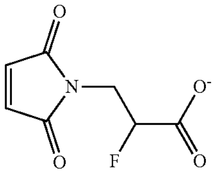
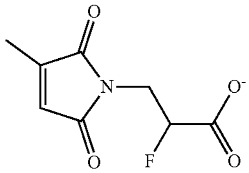
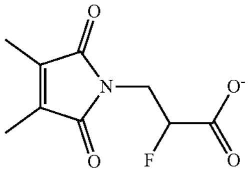
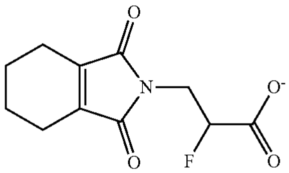
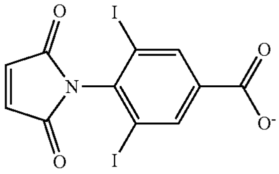
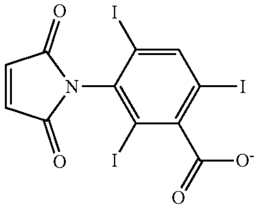
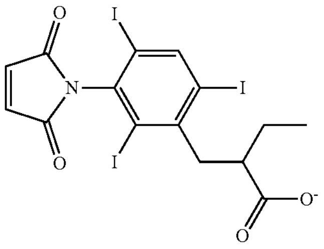
-continued
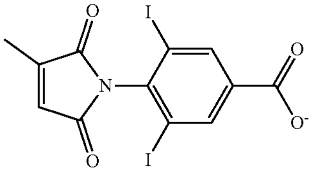
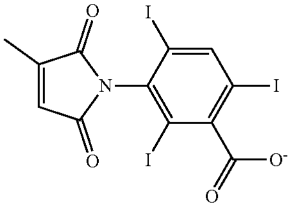
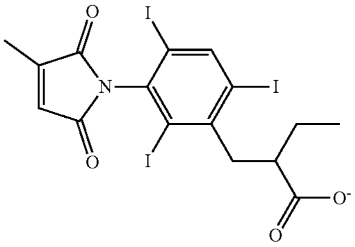
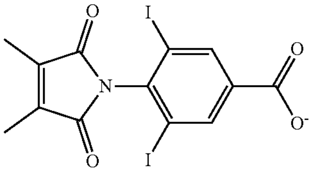
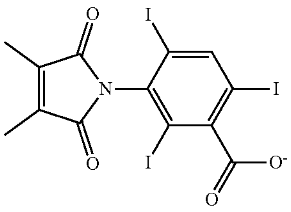
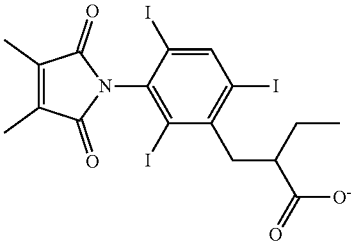
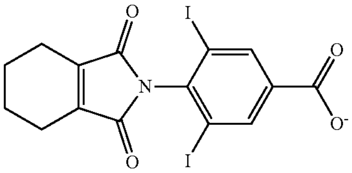
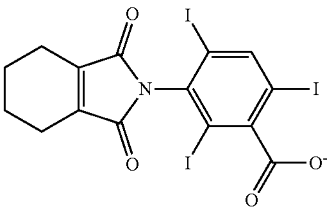

-continued
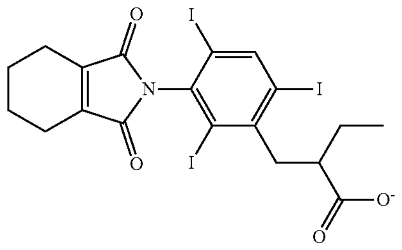
Examples of the cation in the sulfonium salt represented by the general formula (1) include those given below, but are not limited thereto.
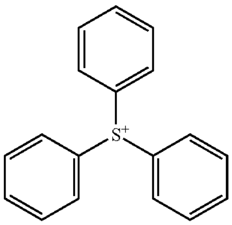
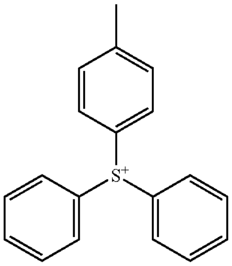
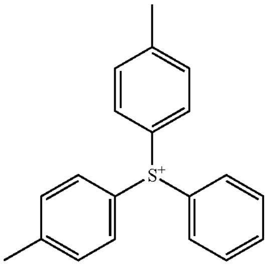
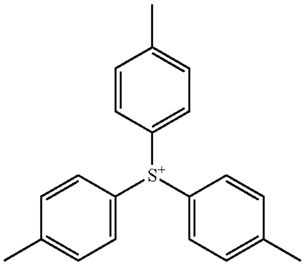
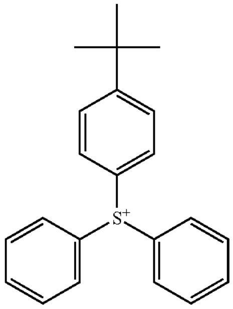
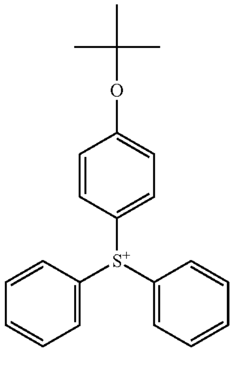
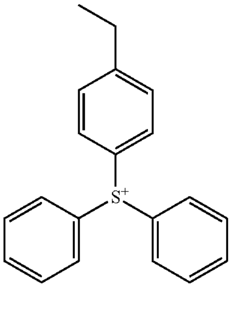
-continued
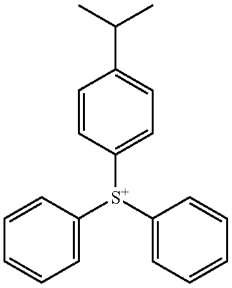
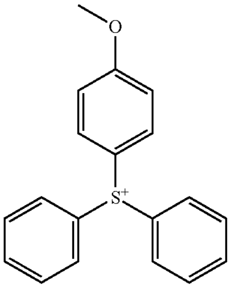
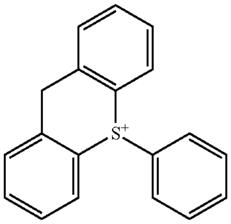
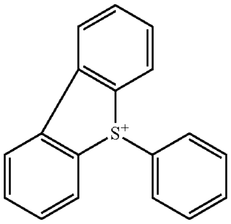
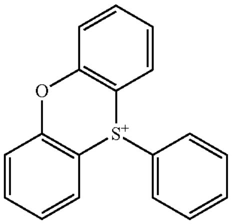
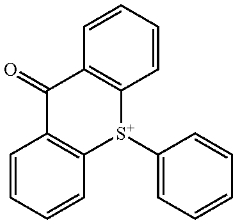
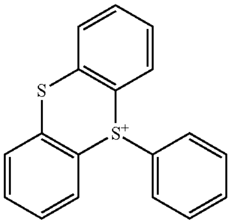
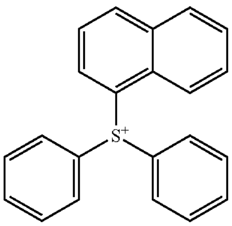
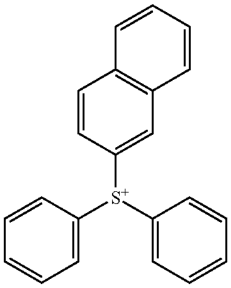
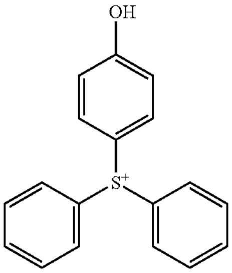
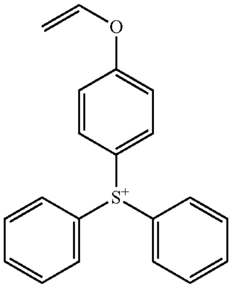
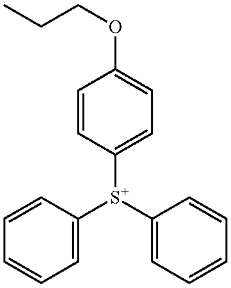

-continued
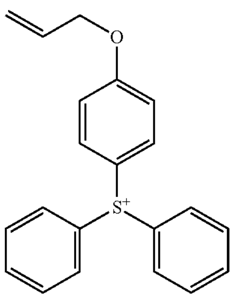
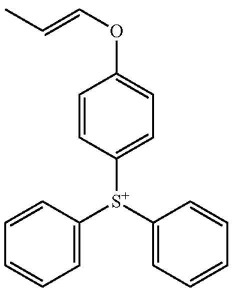
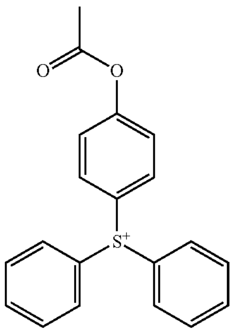
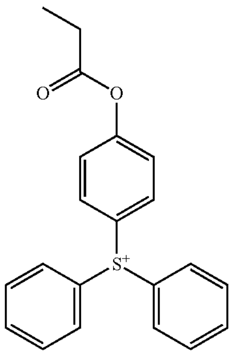
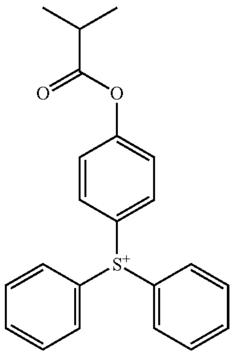
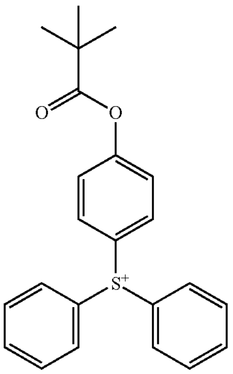
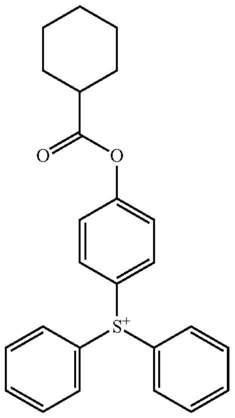
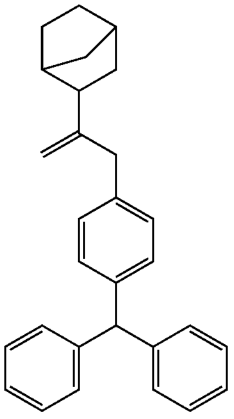
-continued
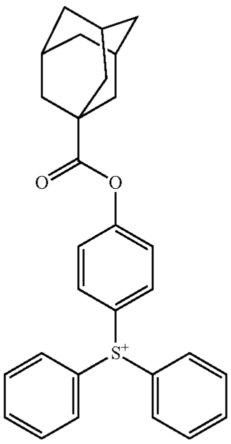
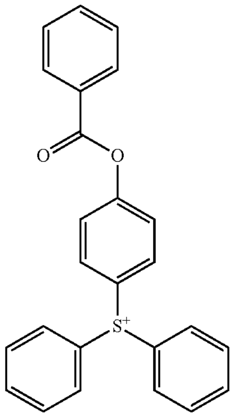
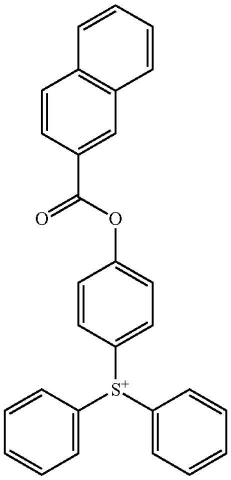
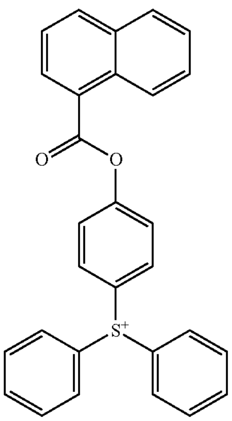
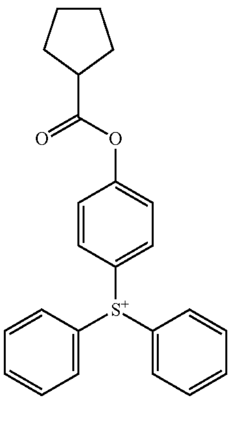
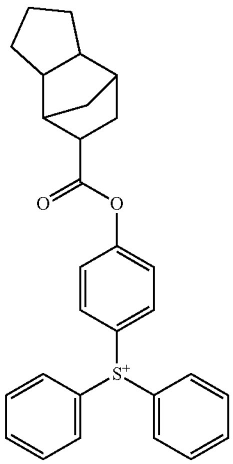

-continued
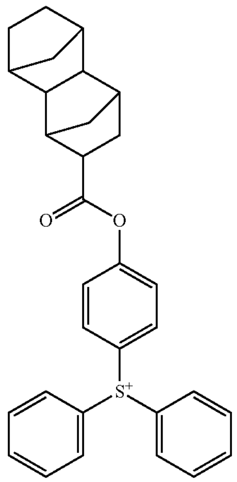
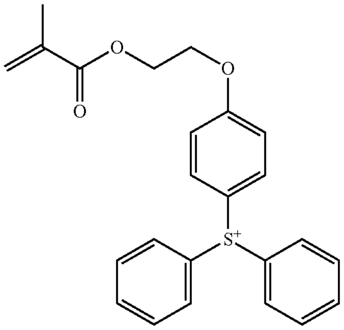
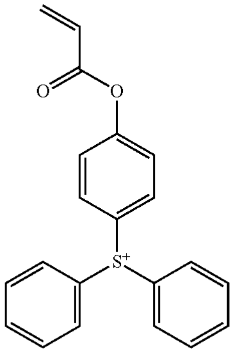
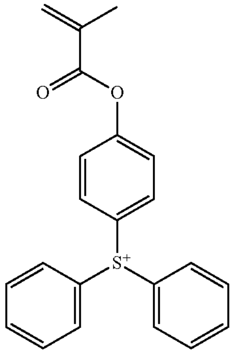
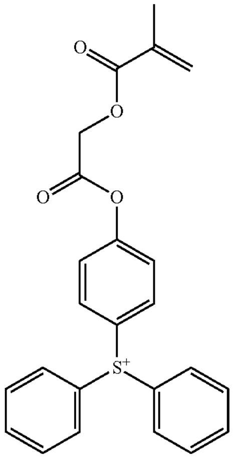
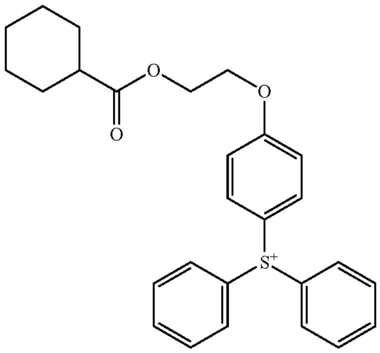
-continued
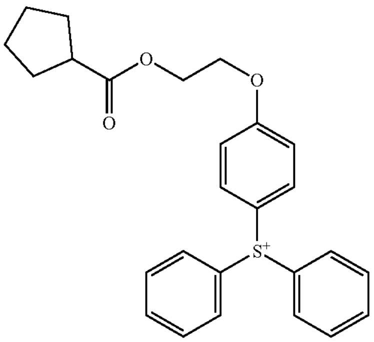
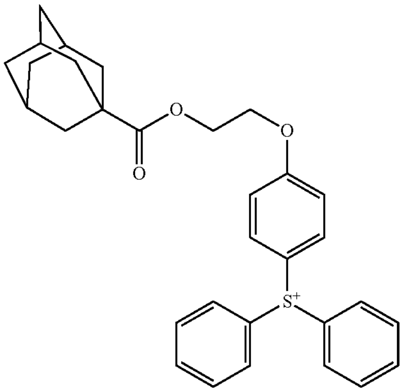
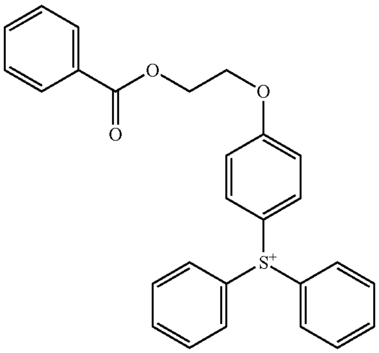
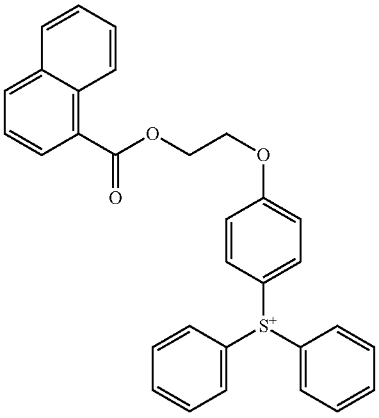

-continued
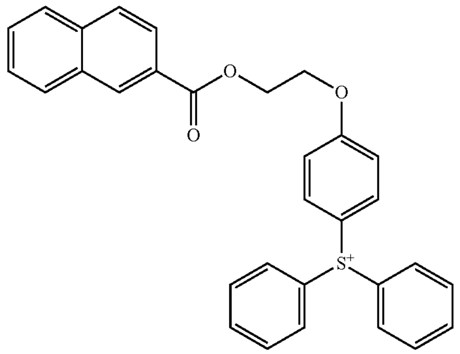
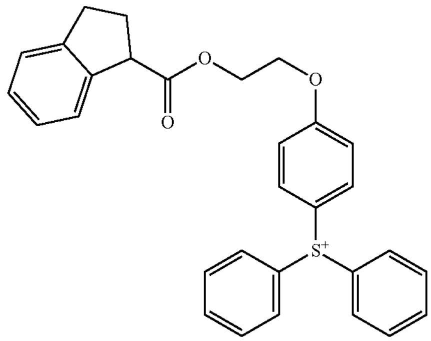
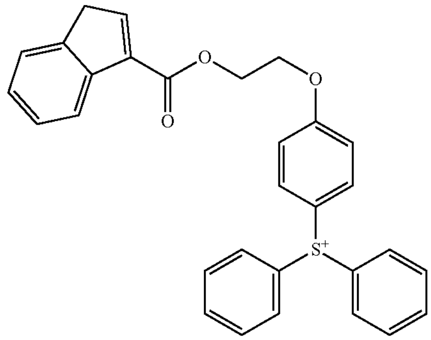
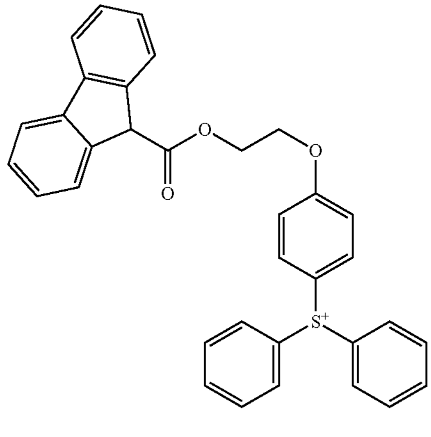
-continued
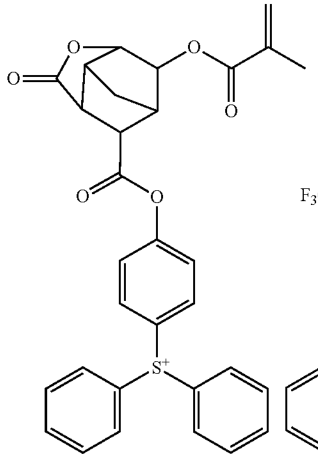
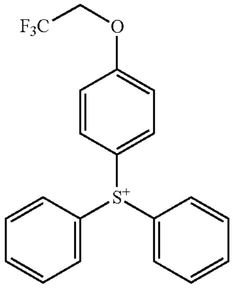
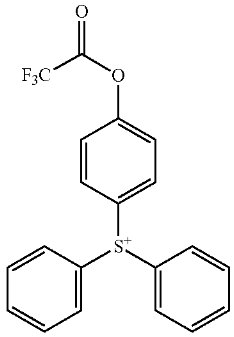
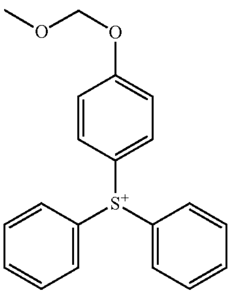
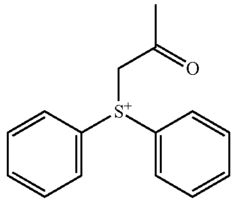
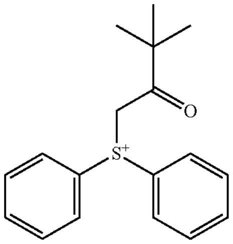
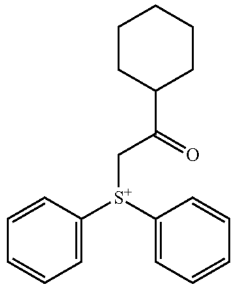
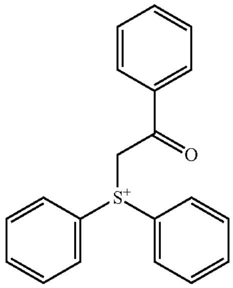
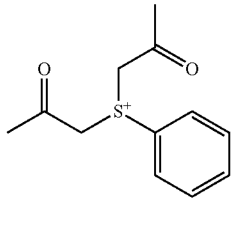
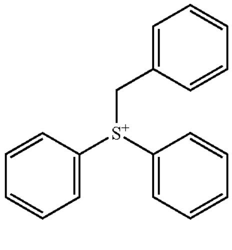

-continued
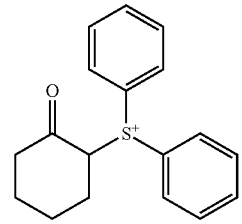
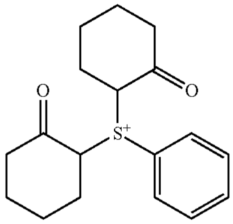
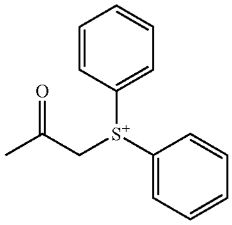
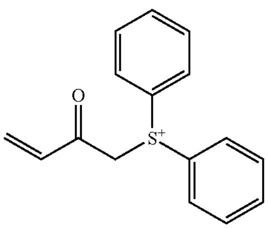
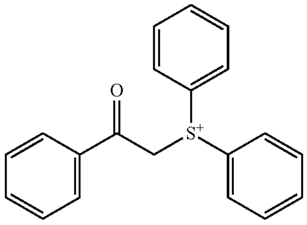
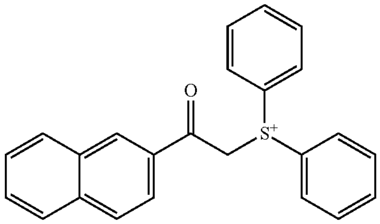
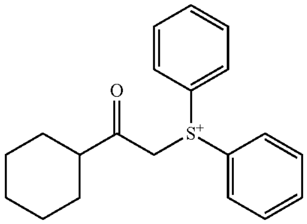
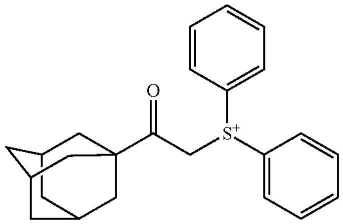
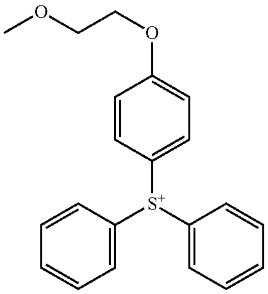
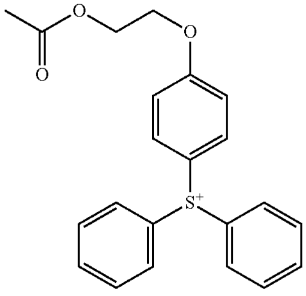
-continued
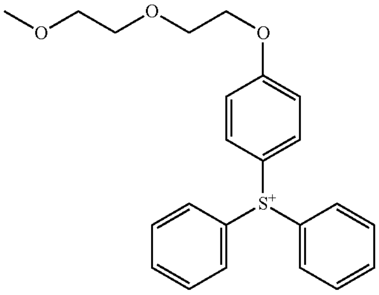
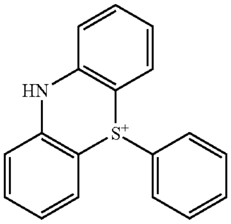
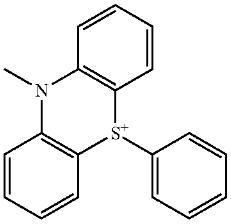
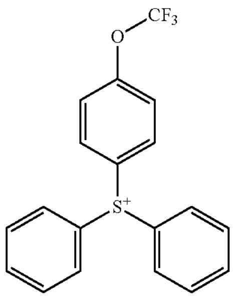
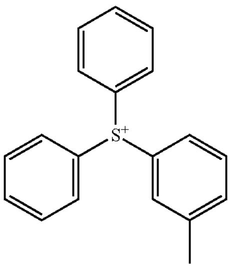
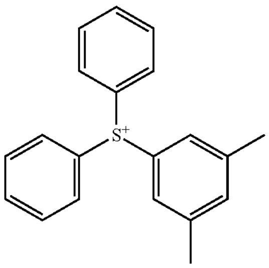
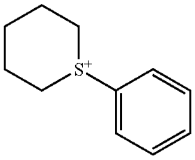
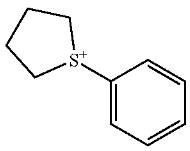
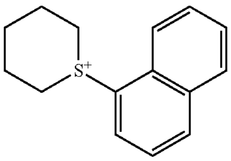
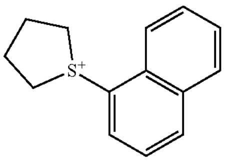
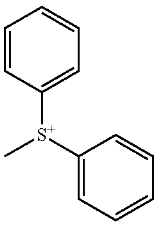
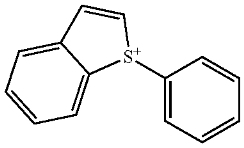

-continued
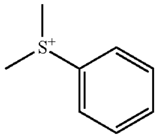
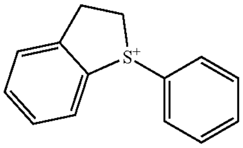
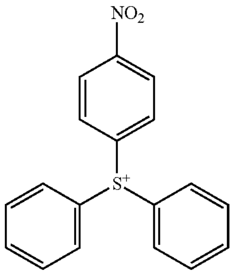
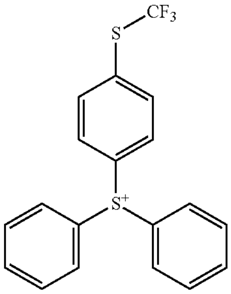
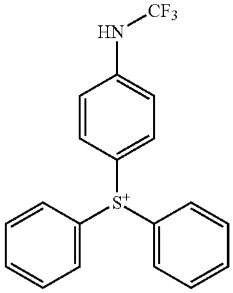
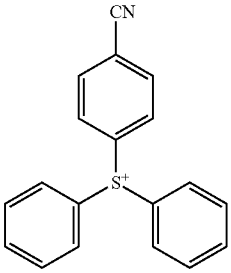
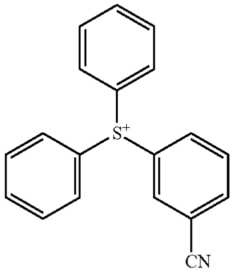
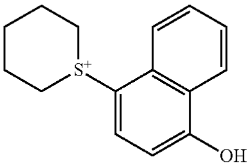
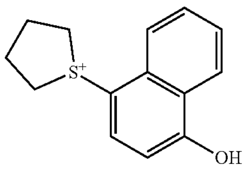
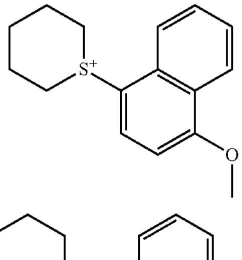
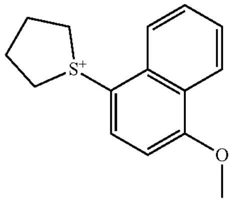
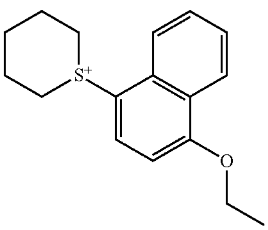
-continued
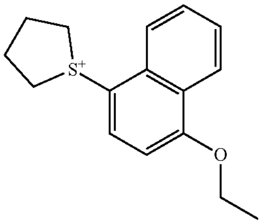
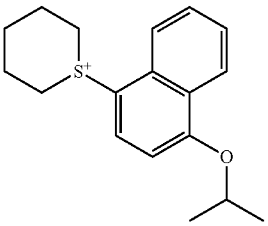
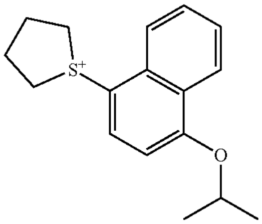
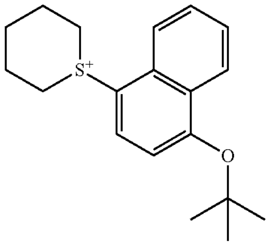
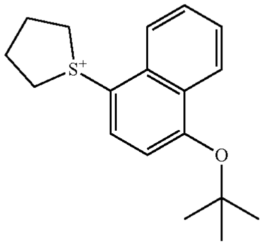
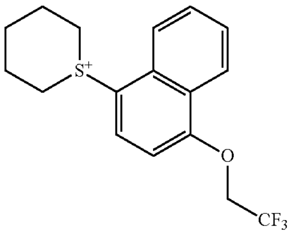
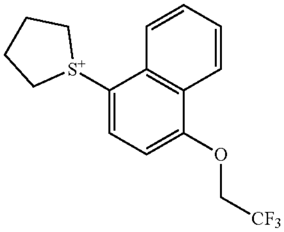
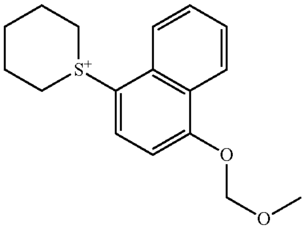
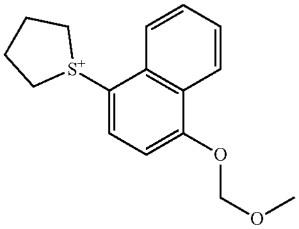
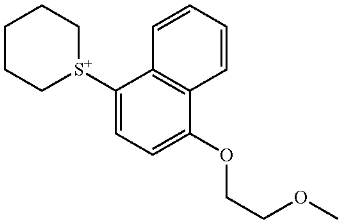

-continued
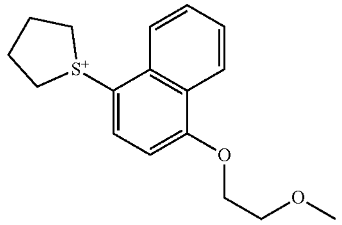
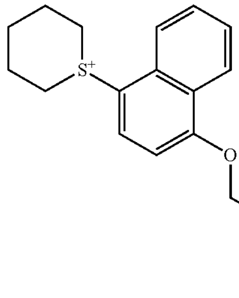
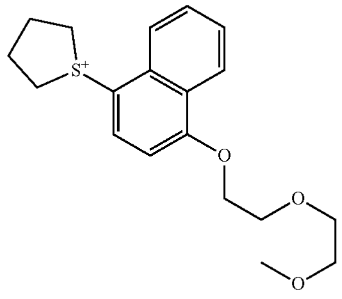
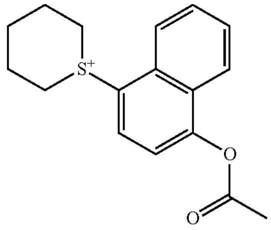
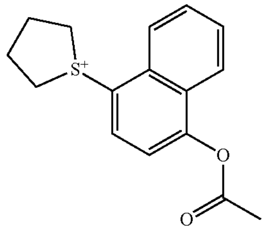
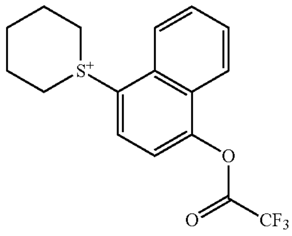
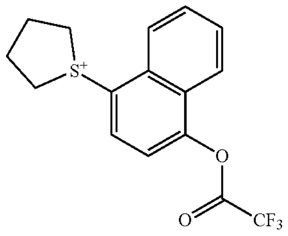
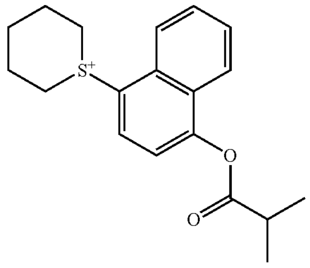
-continued
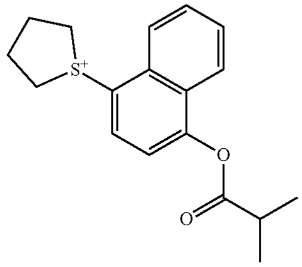
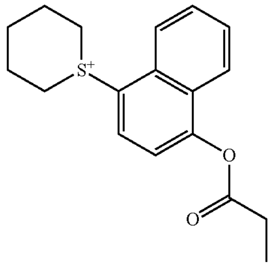
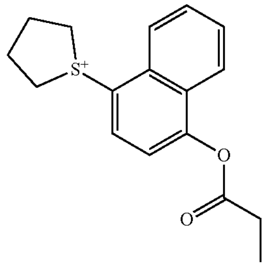
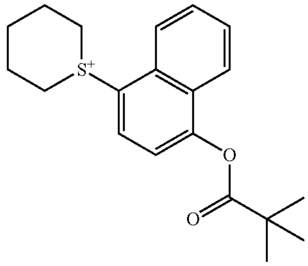
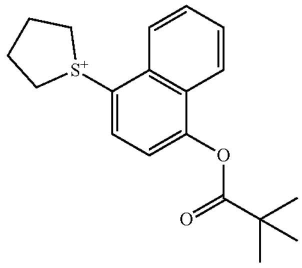
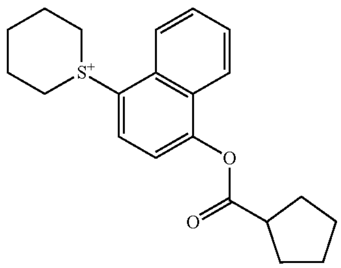

-continued
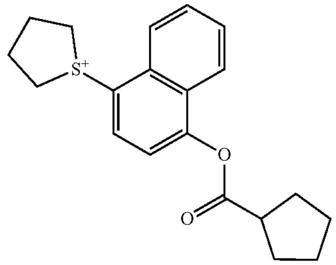
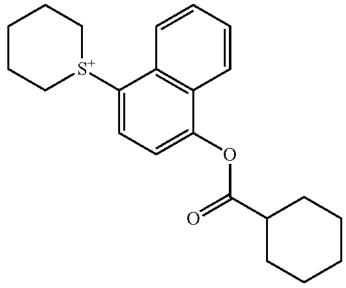
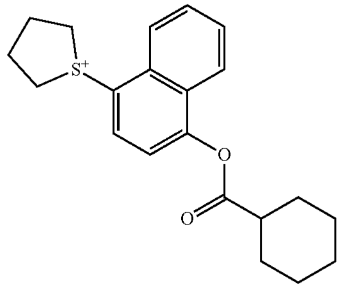
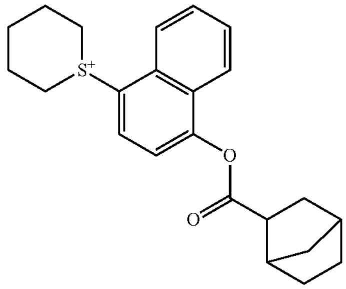
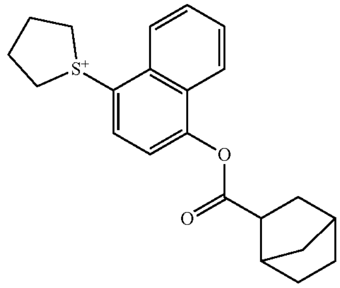
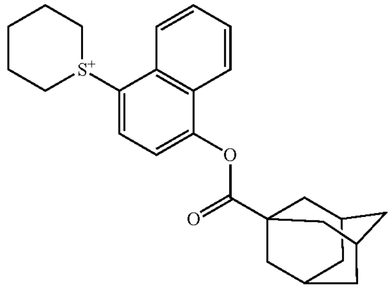
-continued
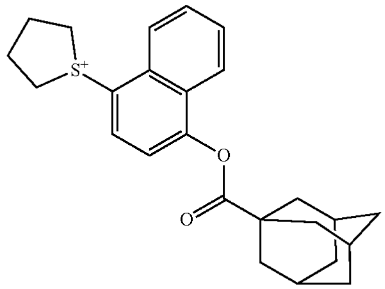
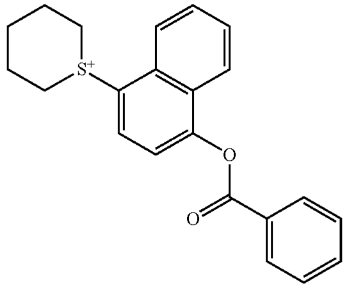
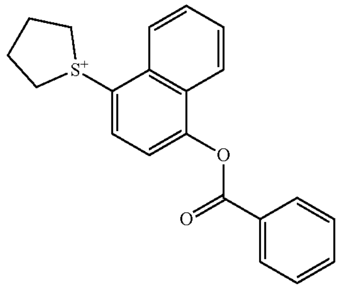
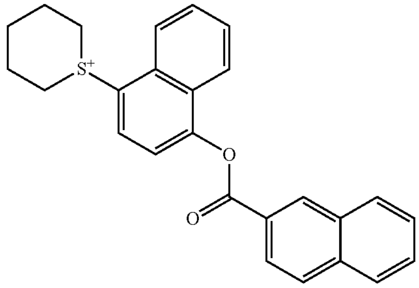
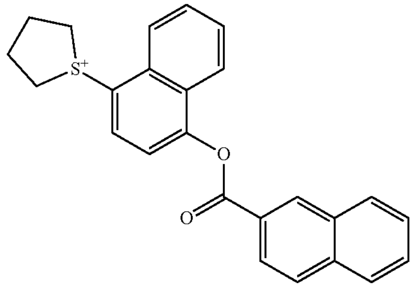
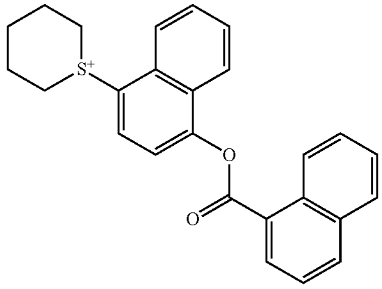

-continued
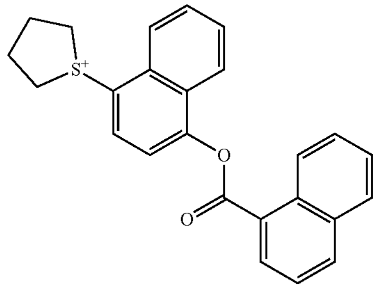
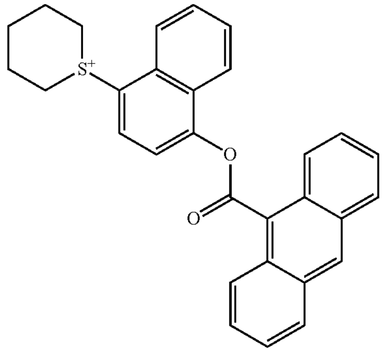
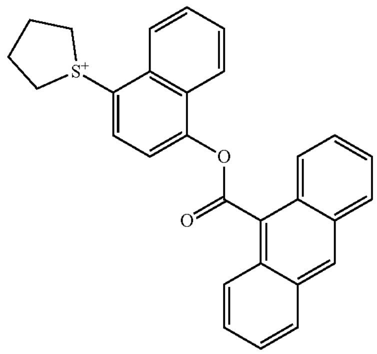
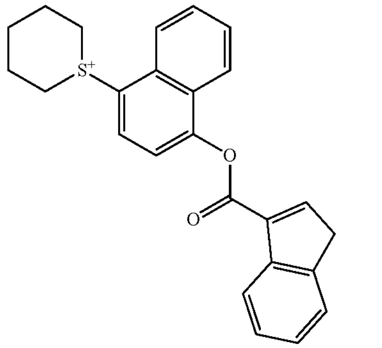
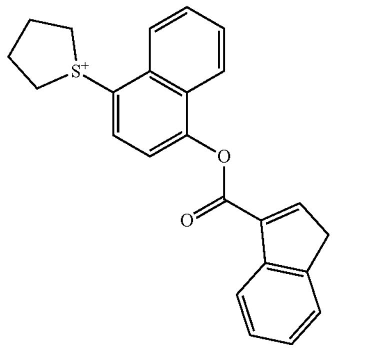
-continued
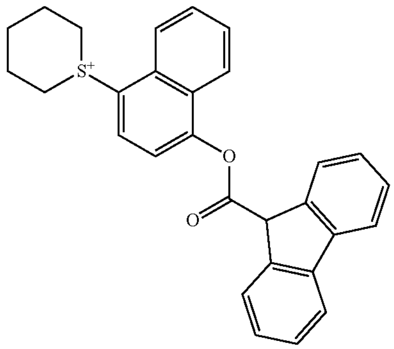
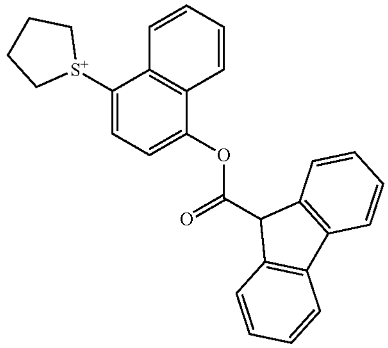
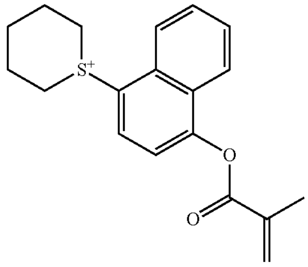
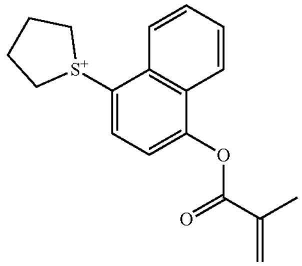
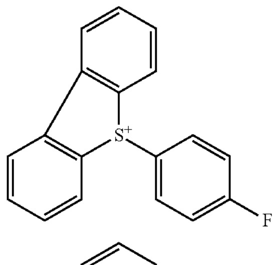
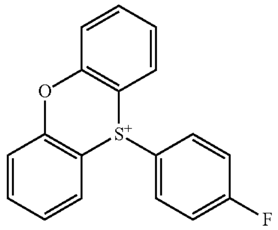

-continued
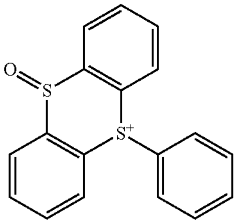
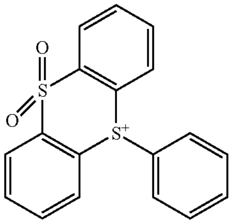
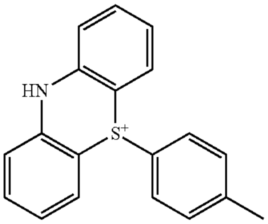
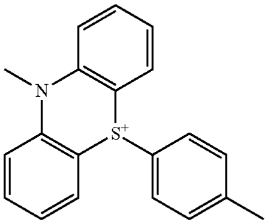
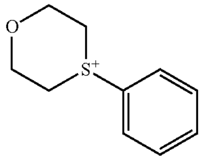
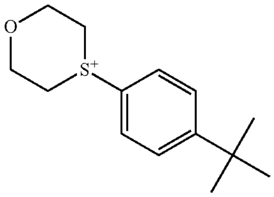
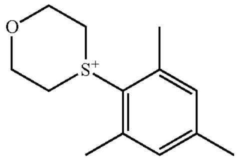
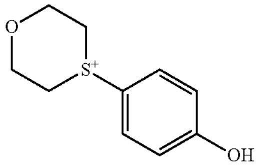
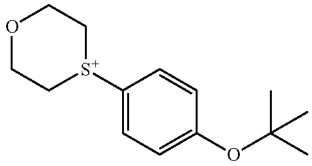
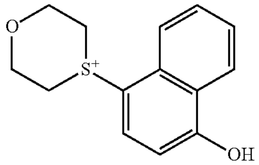
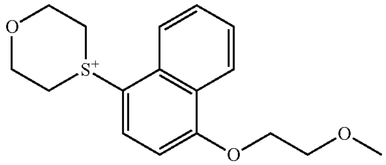
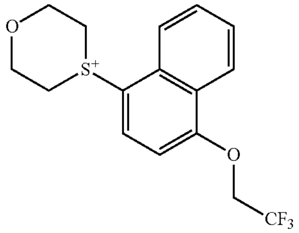
-continued
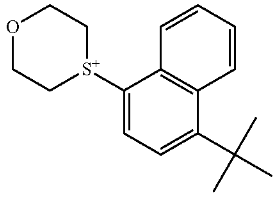
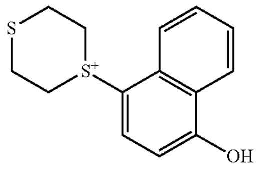
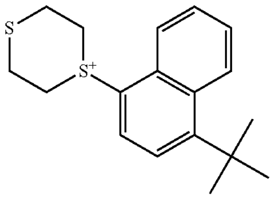
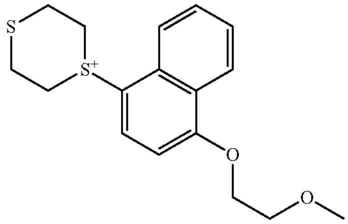
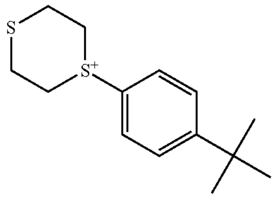
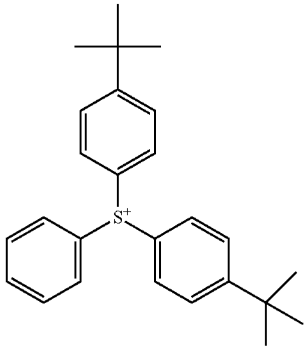
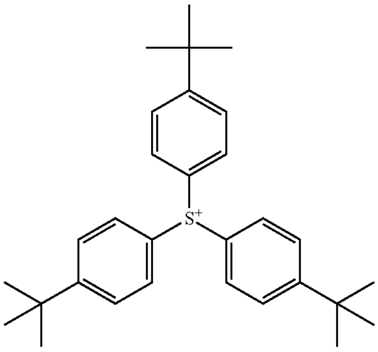

-continued
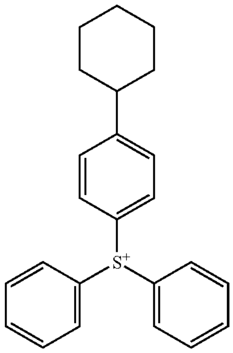
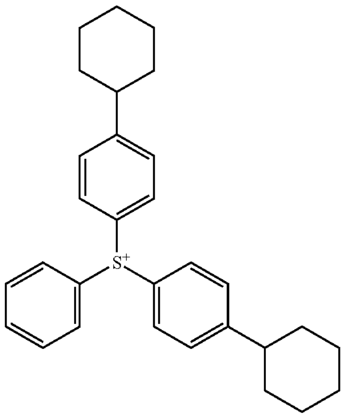
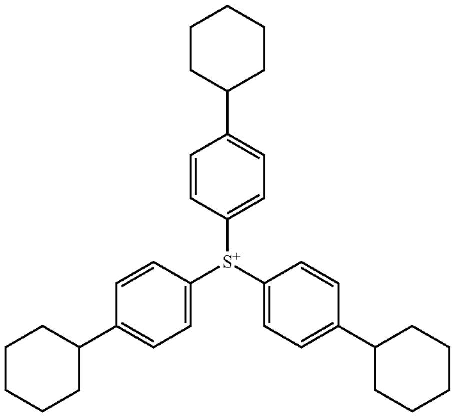
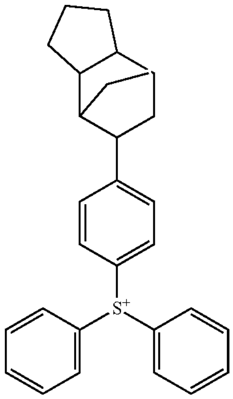
-continued
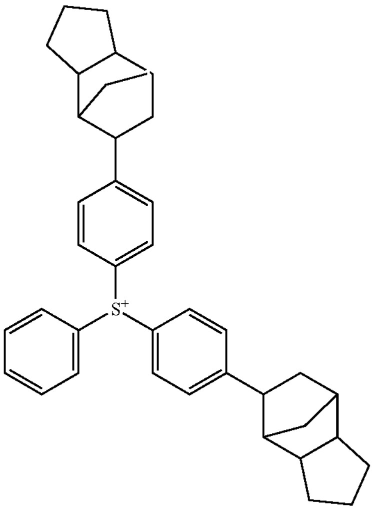
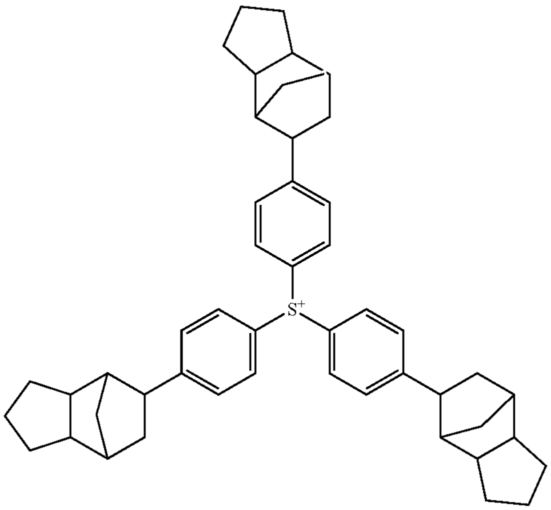
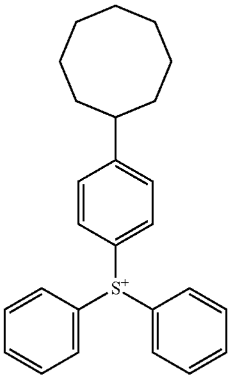

-continued
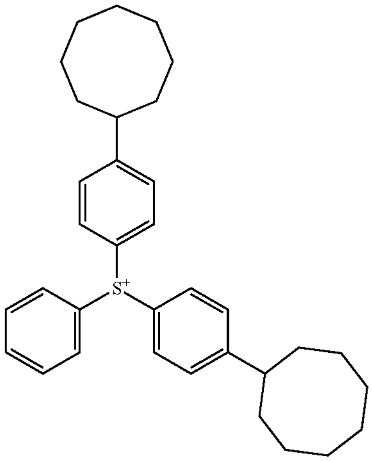
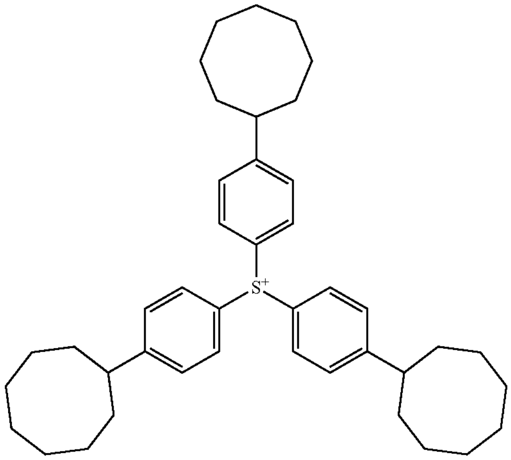
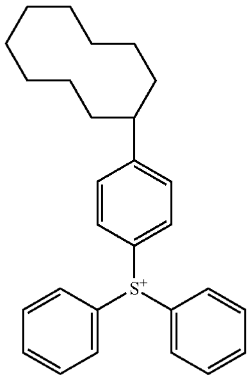
-continued
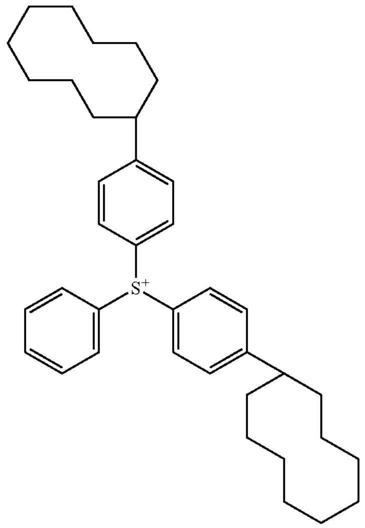
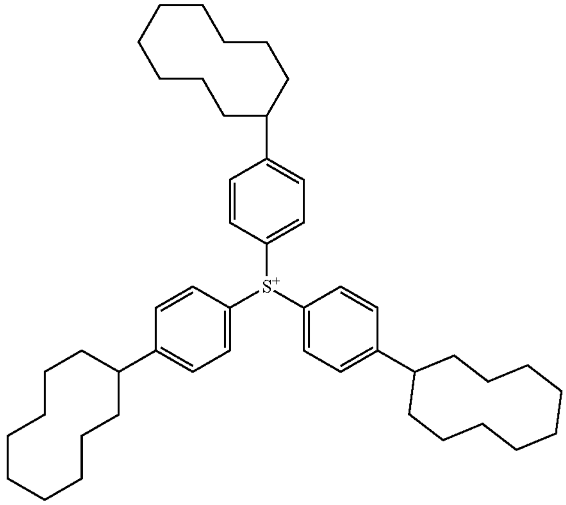
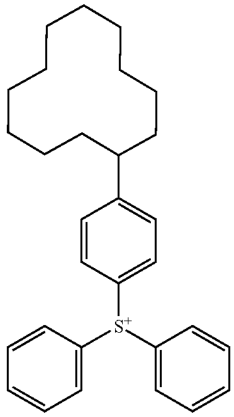

-continued
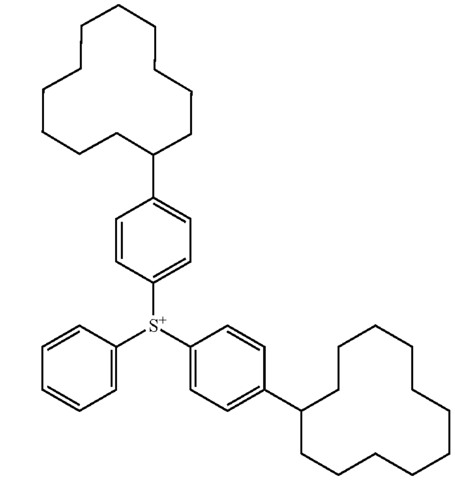
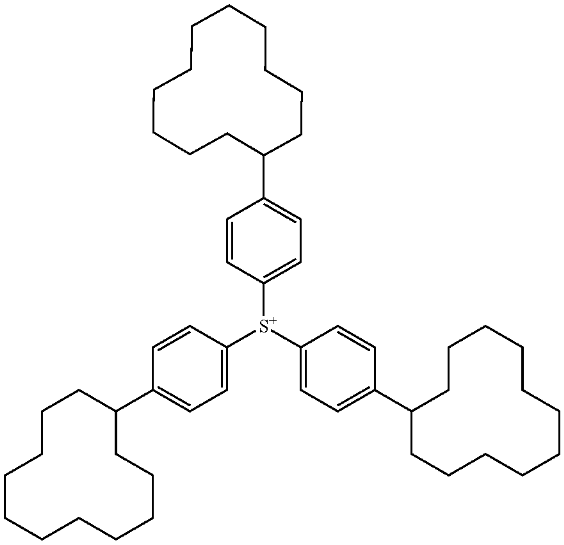
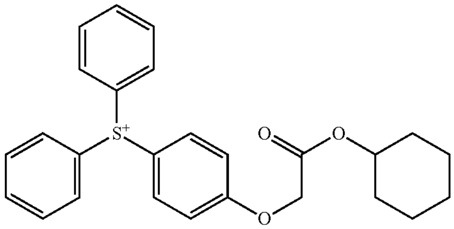
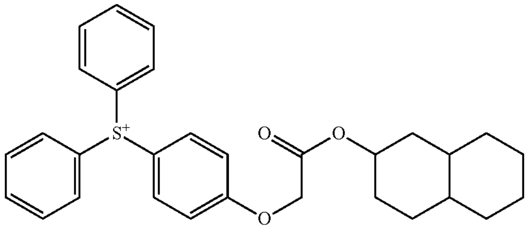
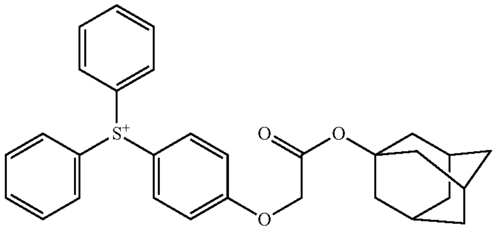
-continued
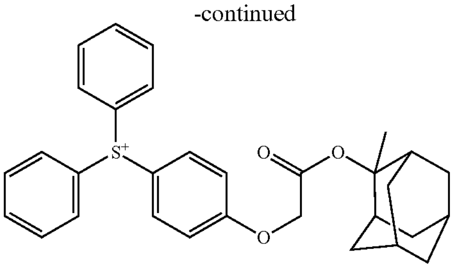
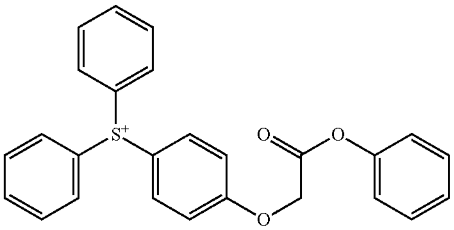
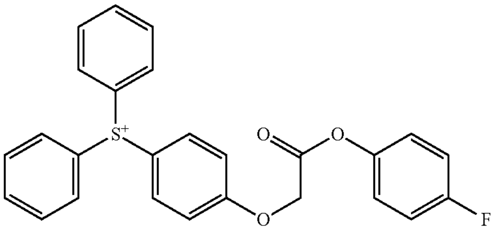
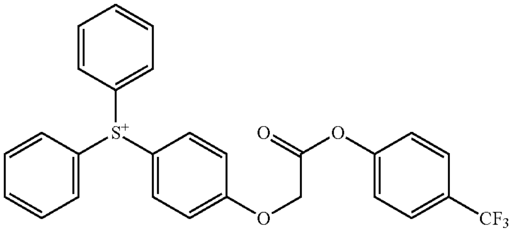
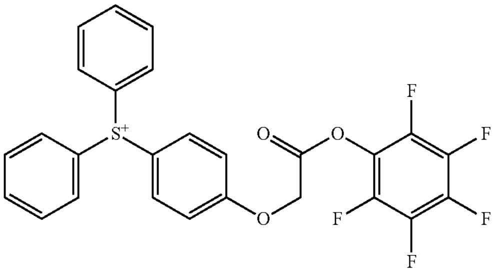

-continued
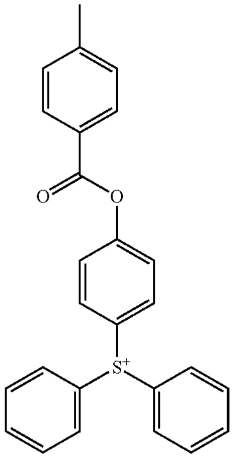
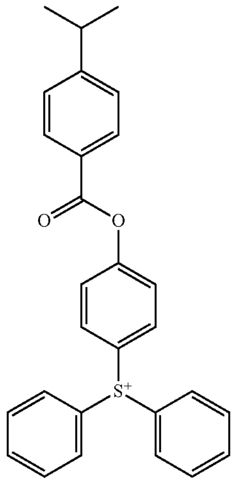
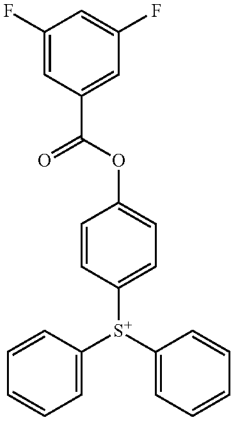
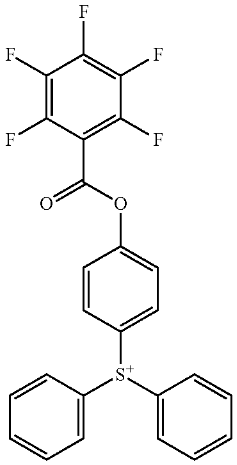
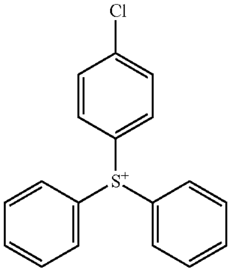
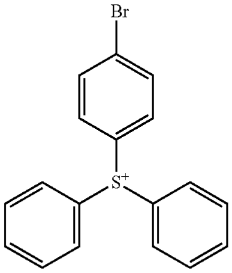
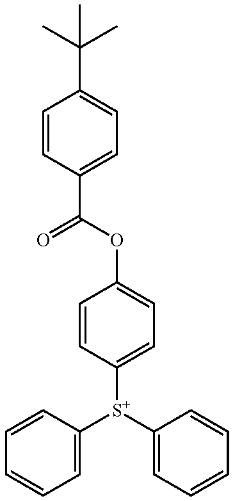
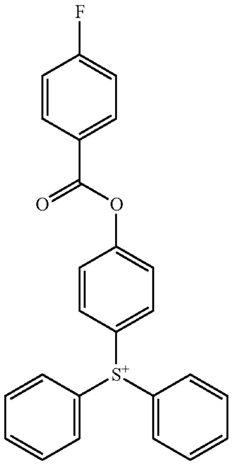
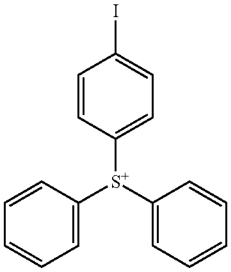
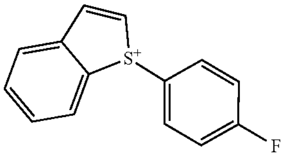
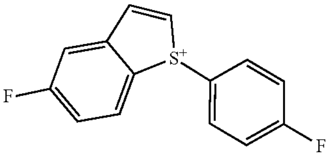
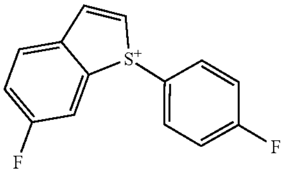
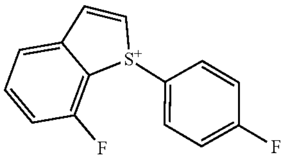
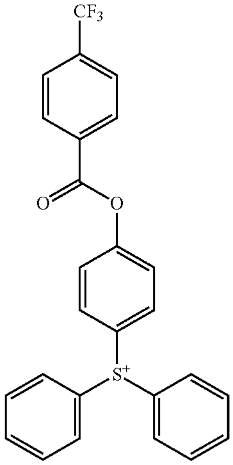
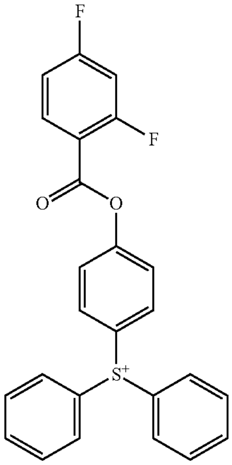
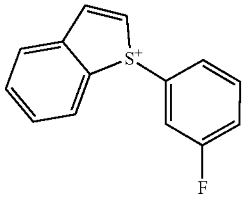
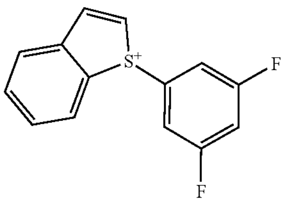
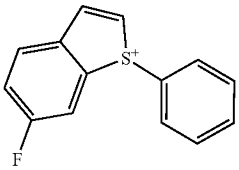
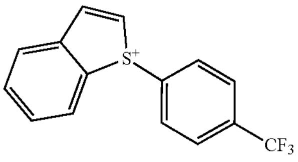

-continued
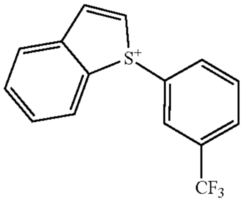
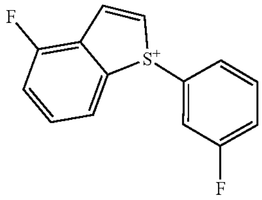
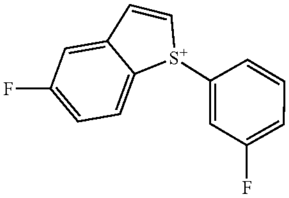
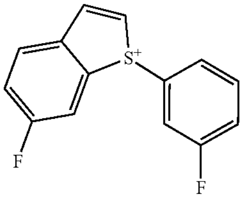
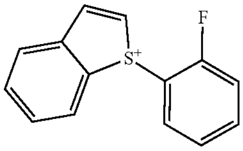
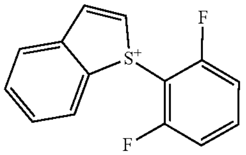
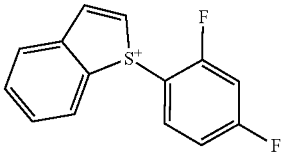
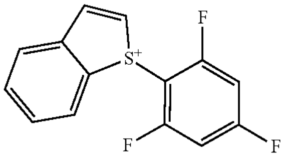
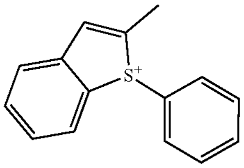
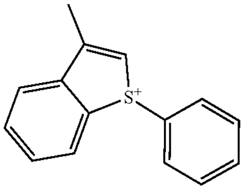
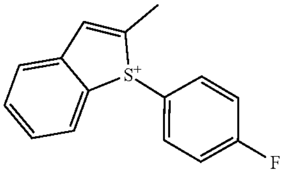
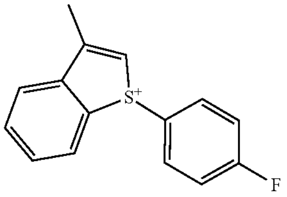
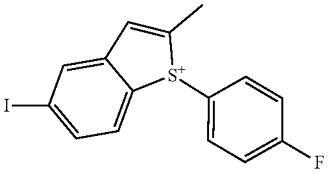
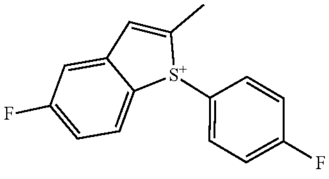
-continued
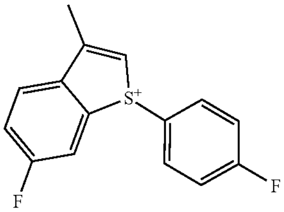
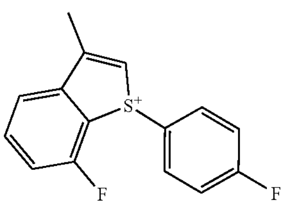
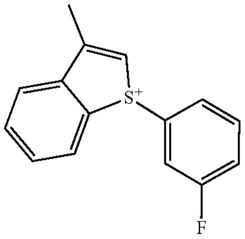
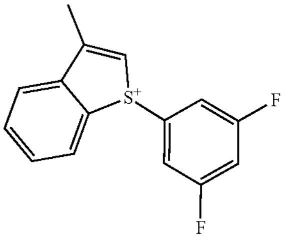
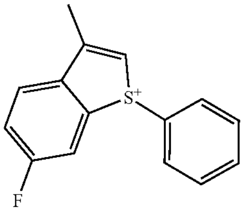
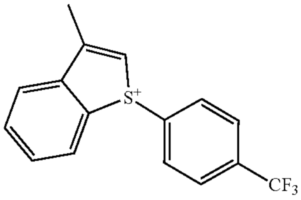
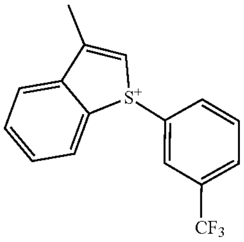
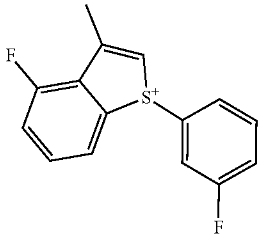
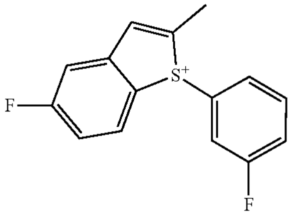
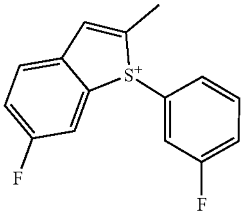
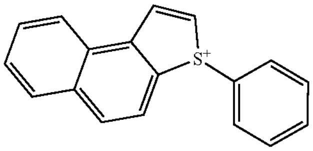
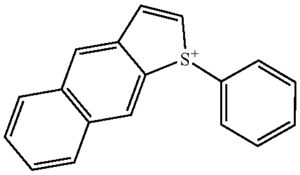
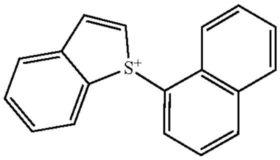

-continued
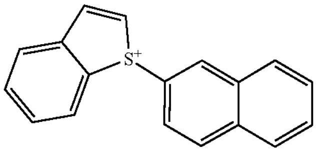
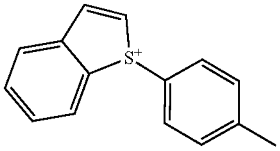
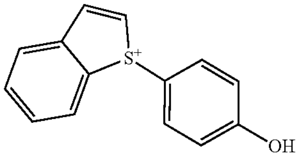
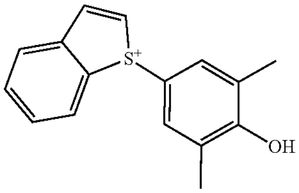
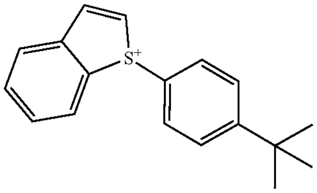
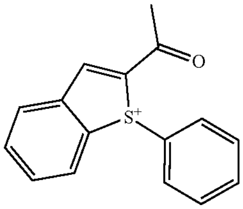
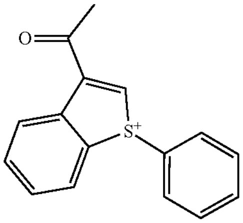
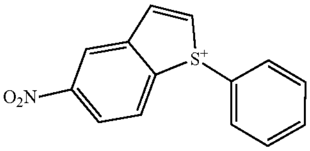
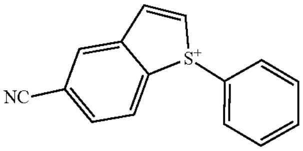
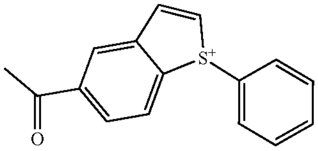
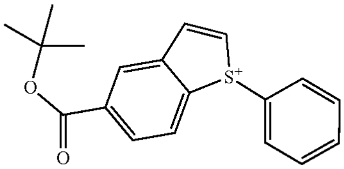
-continued
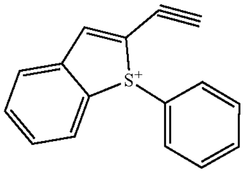
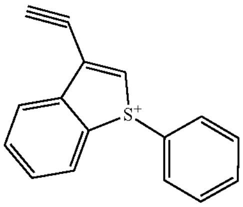
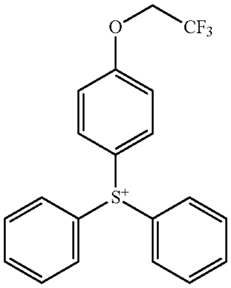
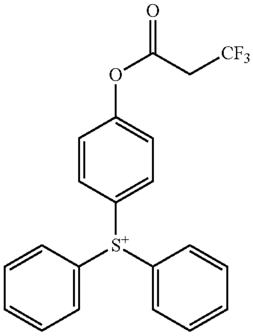
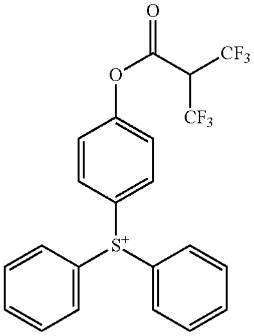
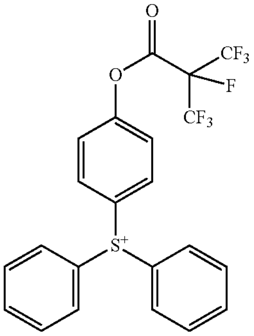
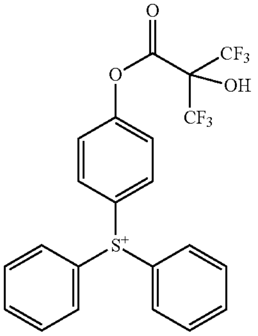
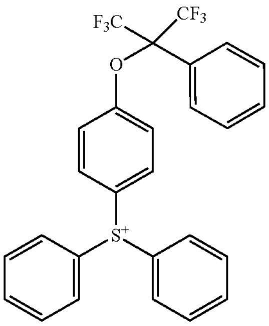
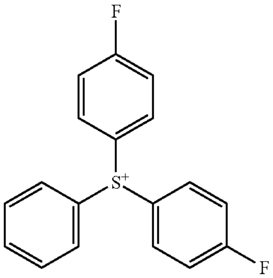

-continued
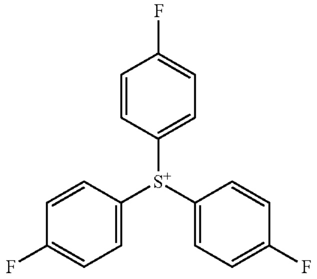
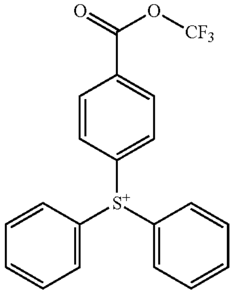
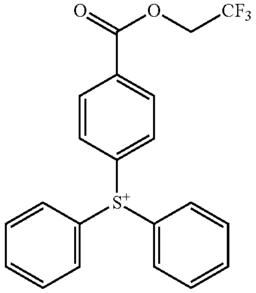
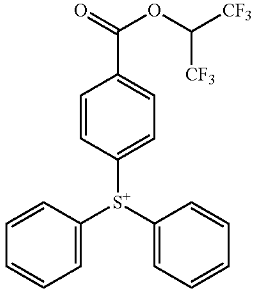
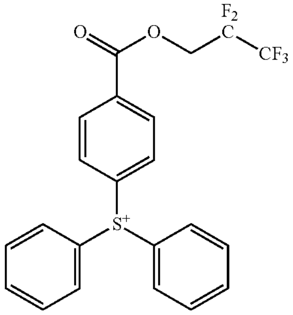
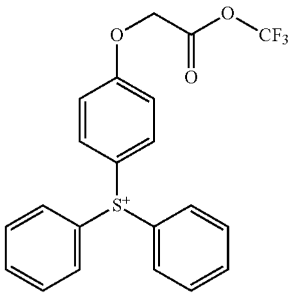
-continued
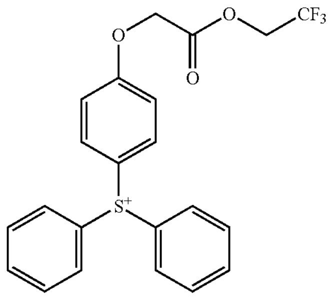
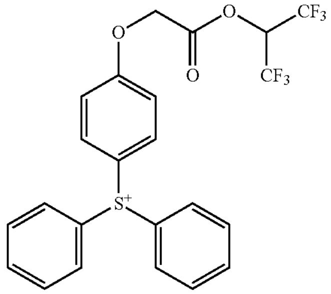
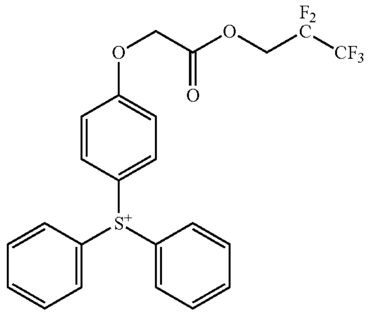
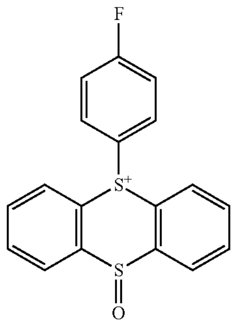
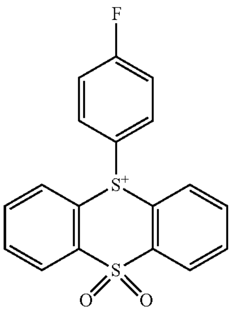
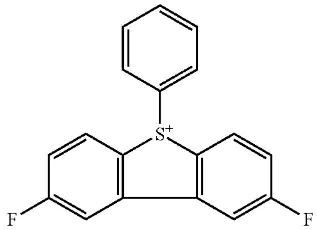
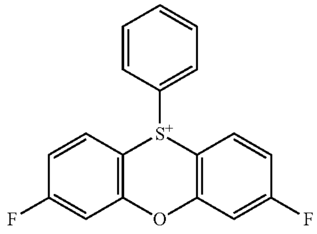

-continued
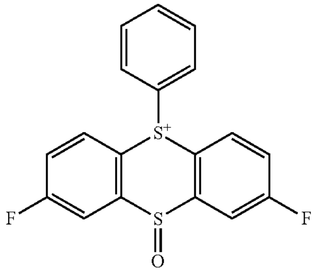
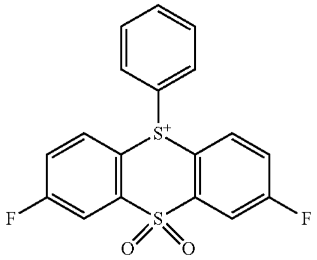
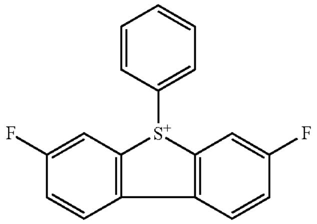
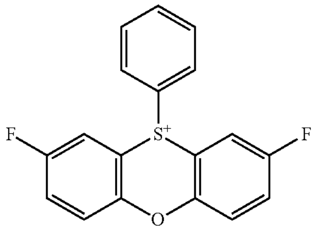
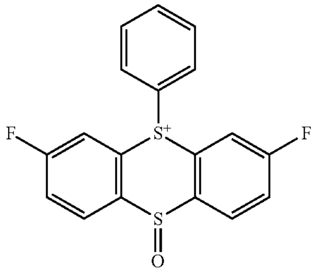
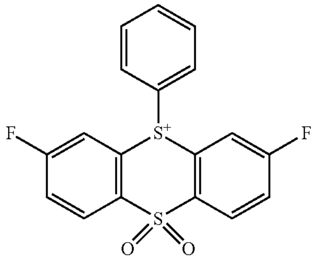
-continued
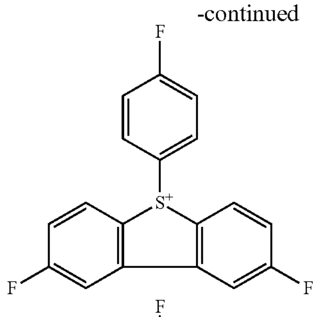
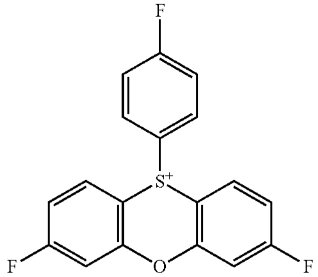
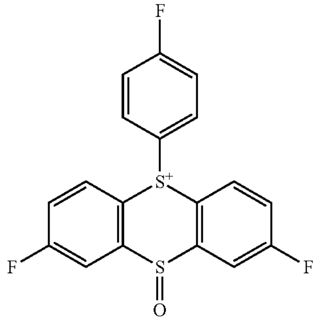
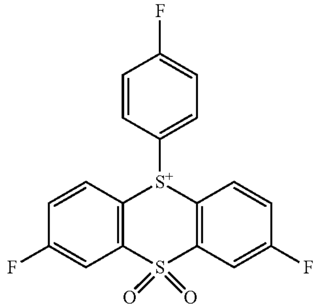
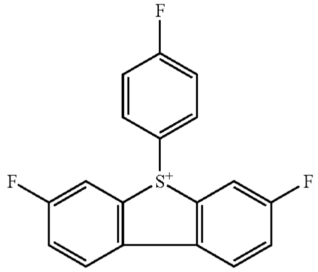
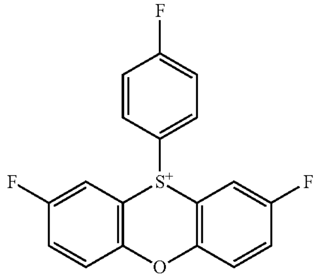

-continued
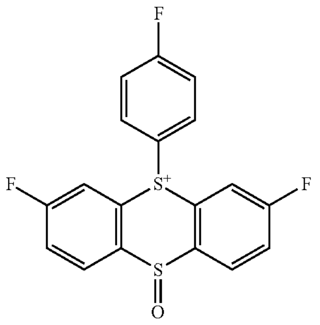
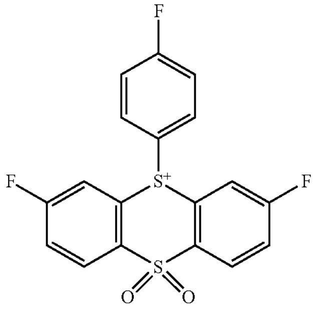
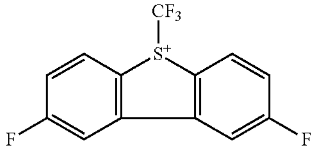
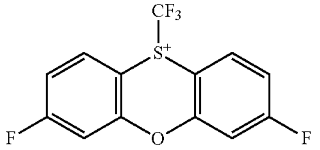
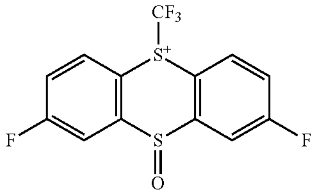
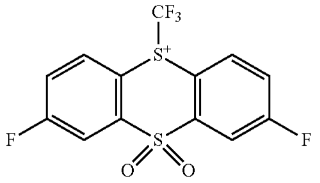
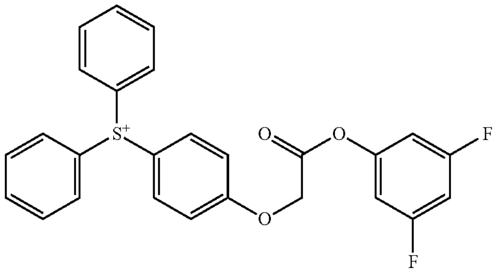
-continued
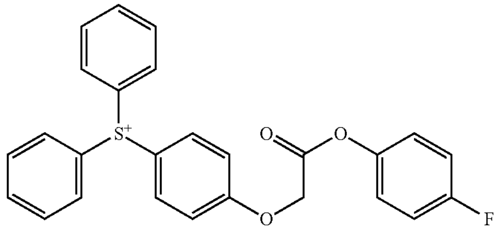
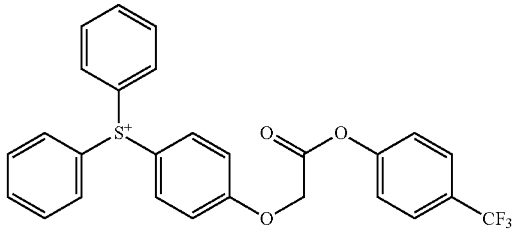
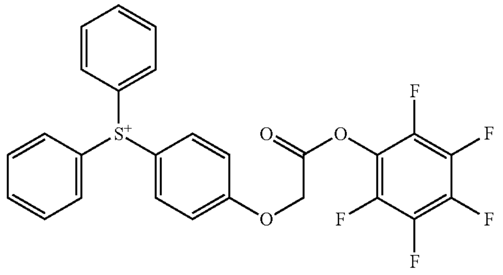
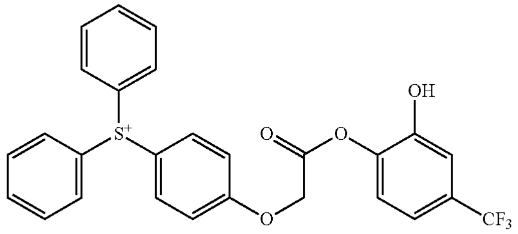
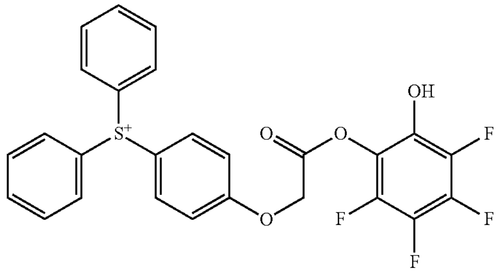
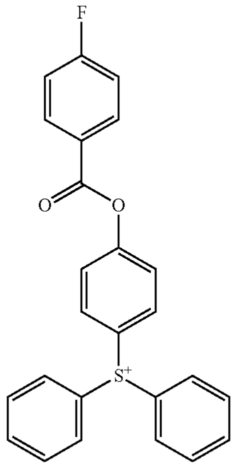
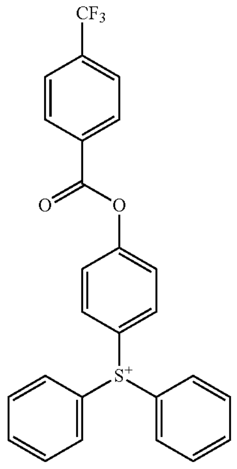

-continued
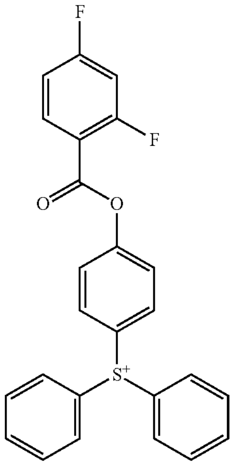
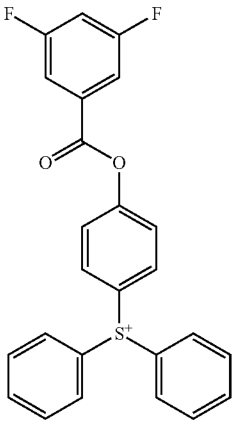
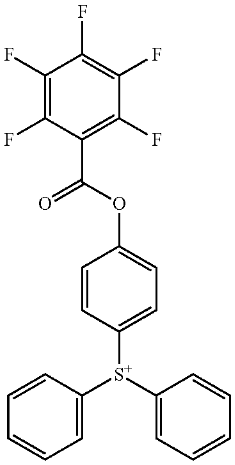
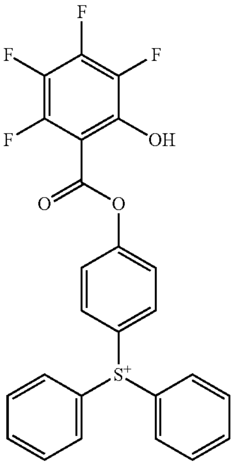
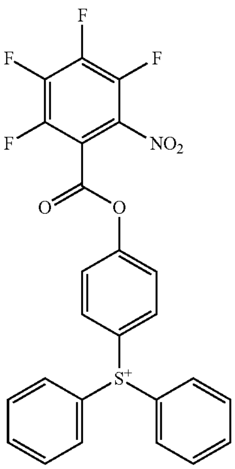
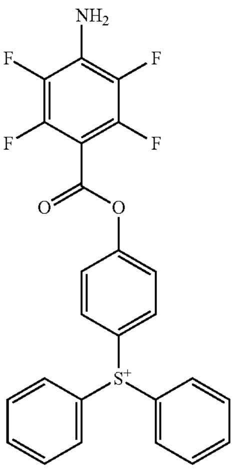
-continued
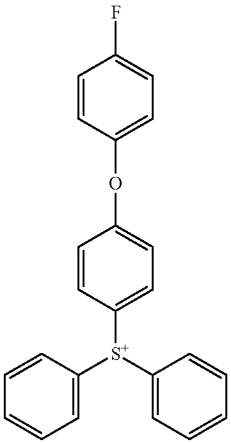
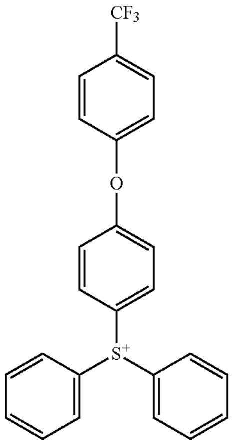
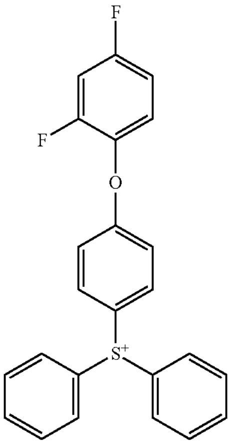
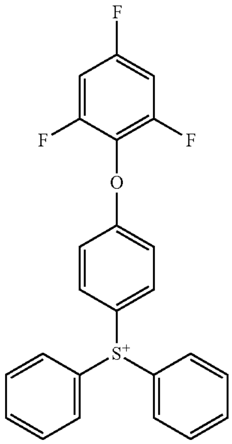
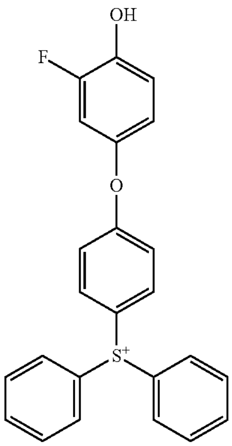
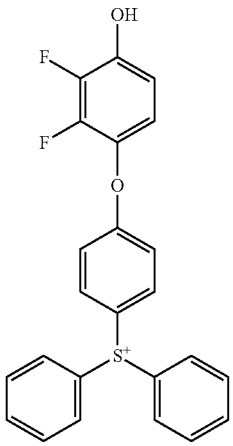

-continued
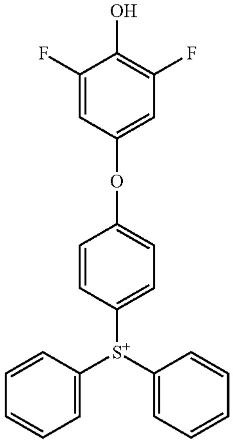
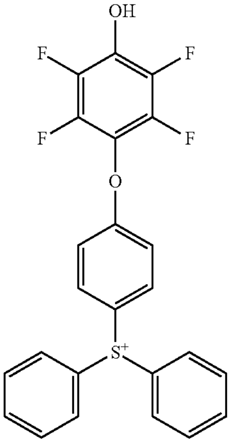
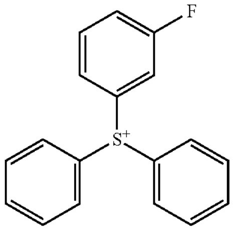
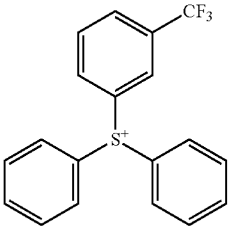
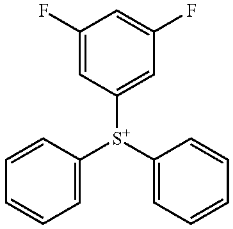
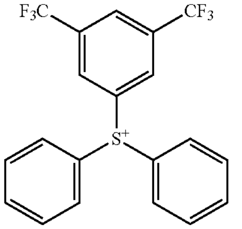
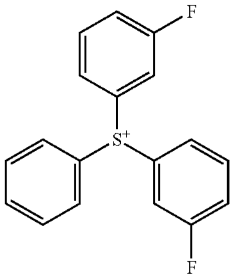
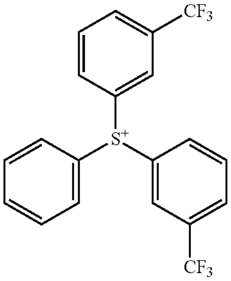
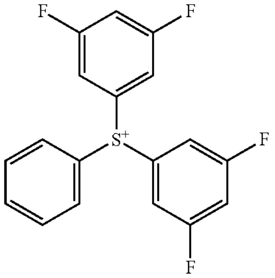
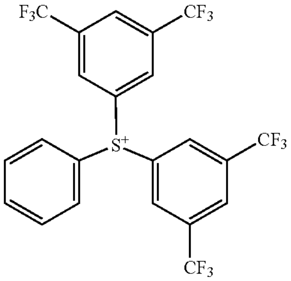
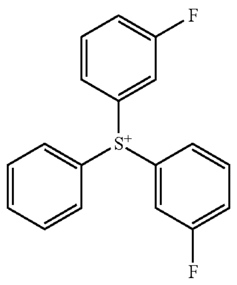
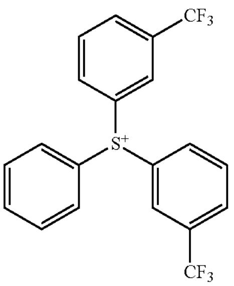
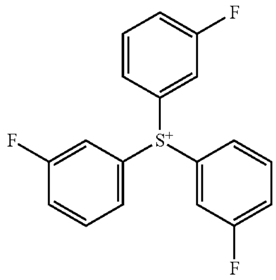
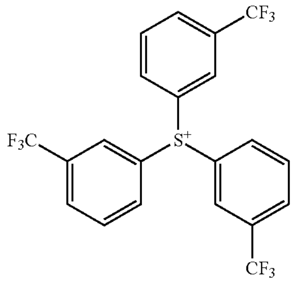
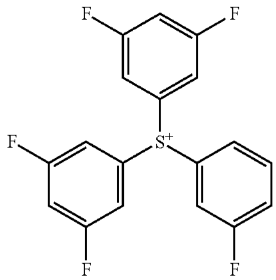
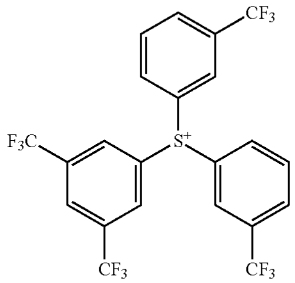
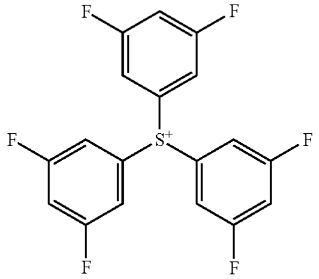

-continued
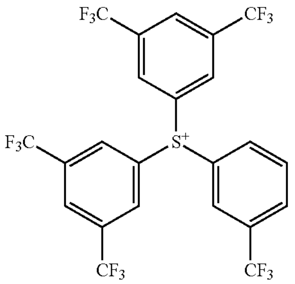
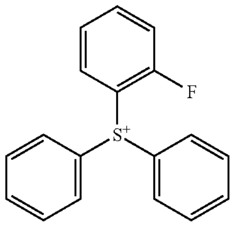
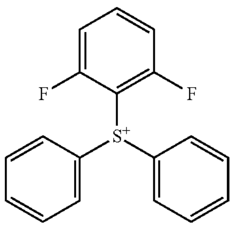
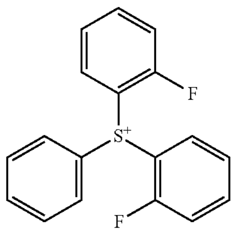
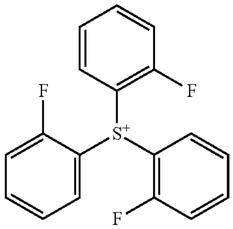
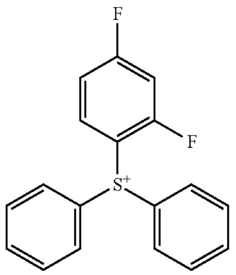
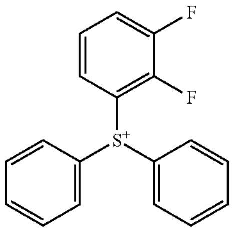
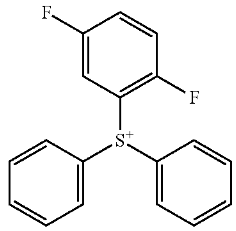
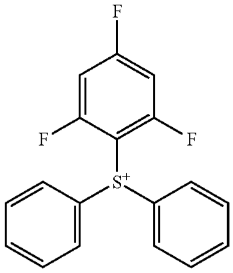
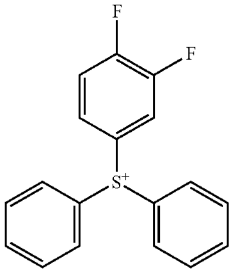
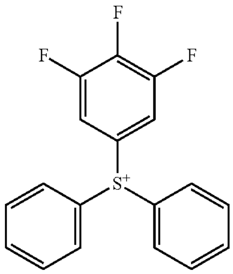
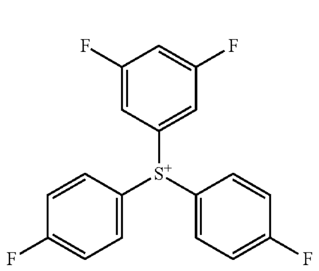
-continued
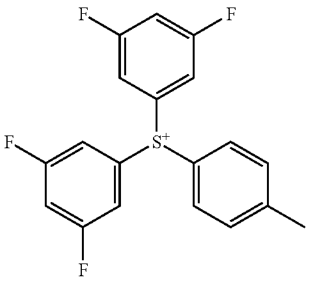
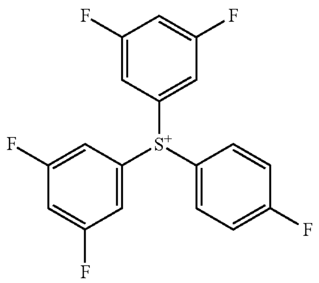
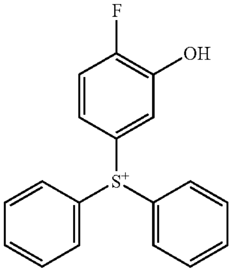
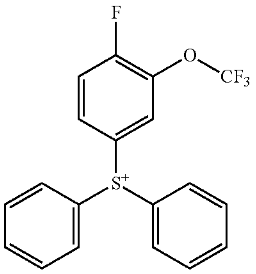
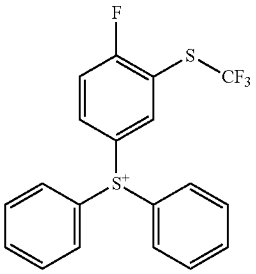
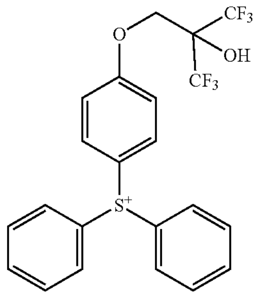
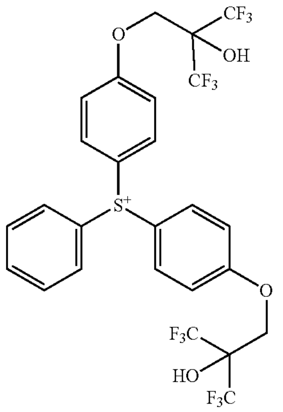
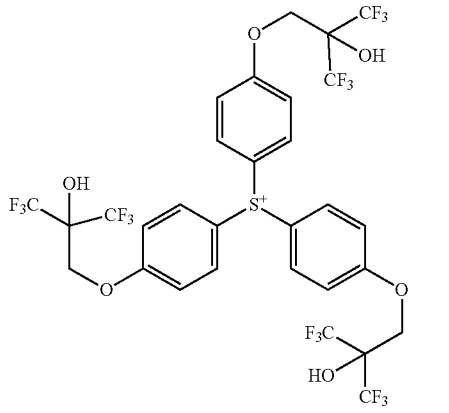

-continued
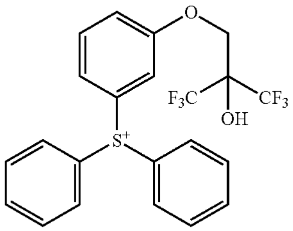
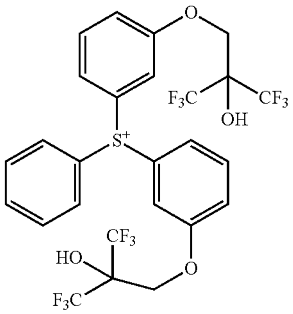
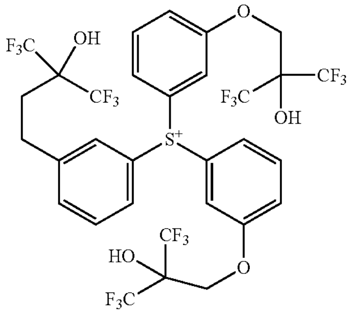
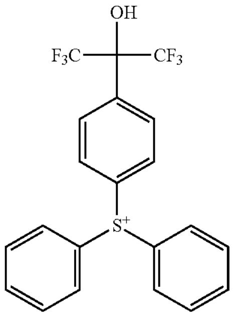
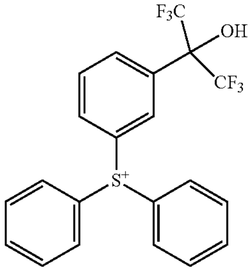
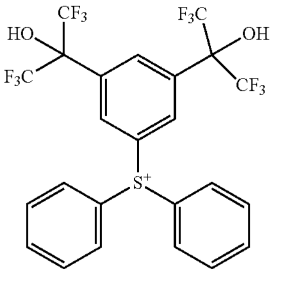
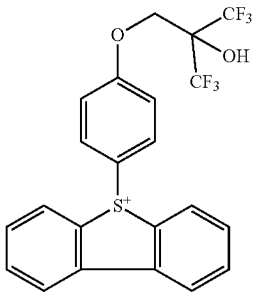
-continued
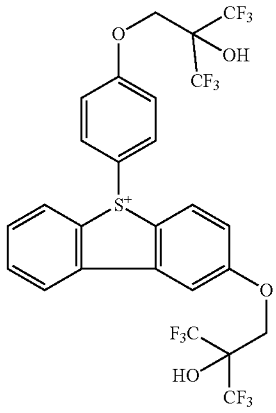
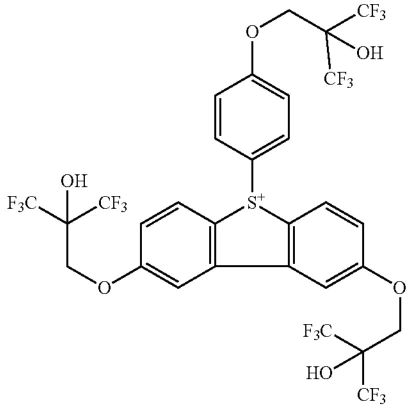
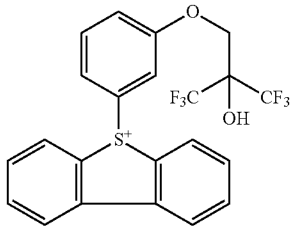
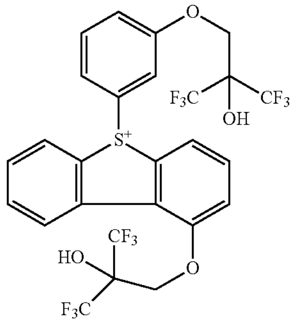
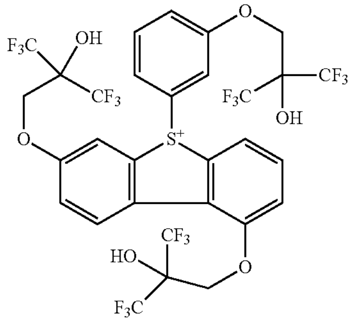

-continued
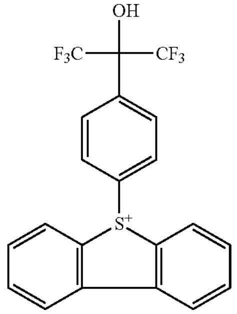
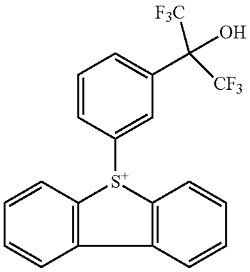
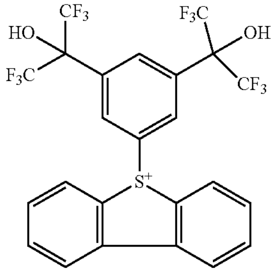
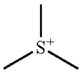
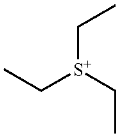
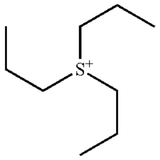
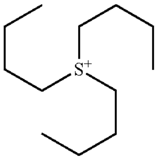
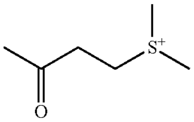
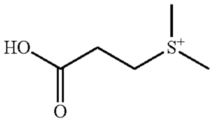
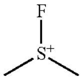
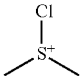
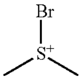
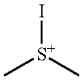
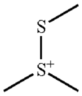
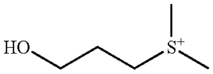
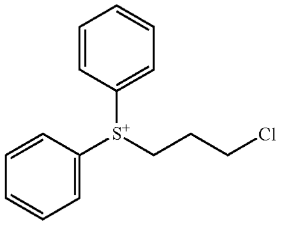
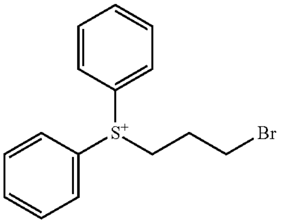
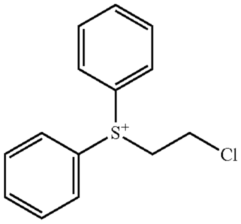
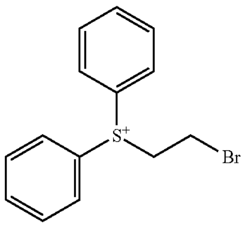
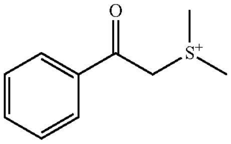
-continued
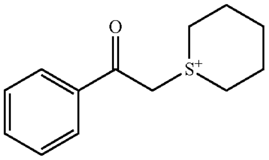
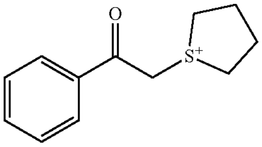
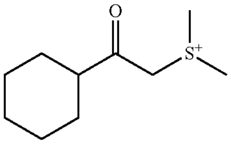
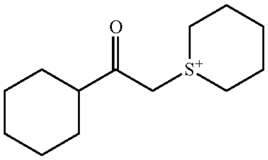
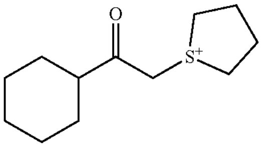
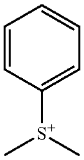
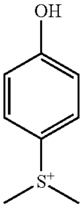
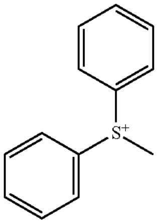
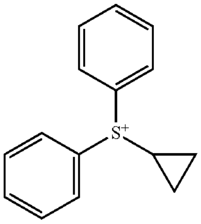
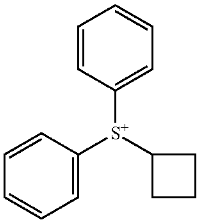
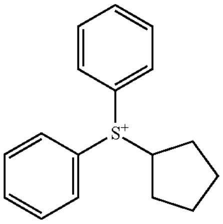
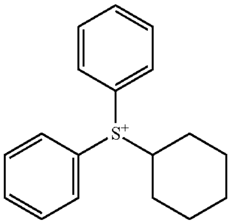
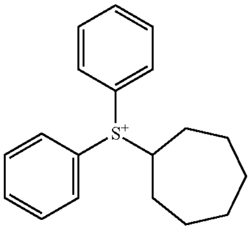
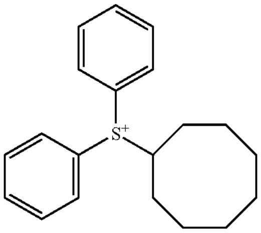
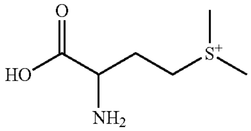
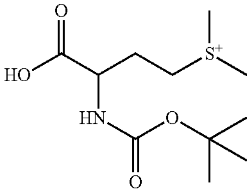
The compound represented by the general formula (1) can be synthesized, for example, by subjecting a hydrochloride or carbonate of triphenylsulfonium to ion exchange with a carboxylic acid bonded to a maleimide group.

In the inventive resist material, the sulfonium salt of the carboxylic acid bonded to the maleimide group is preferably contained in an amount of 0.001 to 50 parts by mass, more preferably 0.01 to 40 parts by mass, further preferably 1 to 10 parts by mass based on 100 parts by mass of the base polymer described below. One kind of the sulfonium salt of a carboxylic acid bonded to a maleimide group may be used, or two or more kinds thereof may be used in combination.

[Base Polymer]

In the case of a positive resist material, the base polymer contained in the inventive resist material preferably contains a repeating unit containing an acid-labile group. As the repeating unit containing an acid-labile group, a repeating unit represented by the following general formula (a1) (hereinafter, also referred to as a repeating unit-a1) or a repeating unit represented by the following general formula (a2) (hereinafter, also referred to as a repeating unit-a2) is preferable.

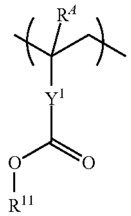

(a1)

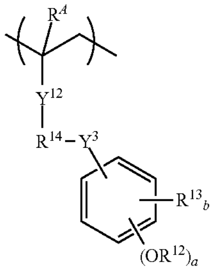

(a2)

In the general formulae (a1) and (a2), each $R^A$ independently represents a hydrogen atom or a methyl group. $R^{11}$ and $R^{12}$ each represent an acid-labile group. $Y^1$ represents a single bond or a linking group having 1 to 12 carbon atoms containing at least one selected from a phenylene group, a naphthylene group, an ester bond, and a lactone ring. $Y^2$ represents a single bond, an ester bond, or an amide bond. $Y^3$ represents a single bond, an ether bond, or an ester bond. $R^{13}$ represents a fluorine atom, a trifluoromethyl group, a cyano group, or a saturated hydrocarbyl group having 1 to 6 carbon atoms. $R^{14}$ represents a single bond or an alkanediyl group having 1 to 6 carbon atoms, and some of the carbon atoms are optionally substituted with an ether bond or an ester bond. "a" represents 1 or 2 and "b" represents an integer of 0 to 4, provided that $1 \leq a+b \leq 5$.

Note that when the base polymer contains both the repeating unit-a1 and the repeating unit-a2, $R^{11}$ and $R^{12}$ may be identical to or different from one another.

Examples of a monomer to give the repeating unit-a1 include those shown below, but are not limited thereto. Incidentally, in the following formulae, $R^A$ and $R^{11}$ are the same as above.

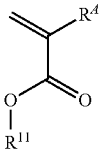

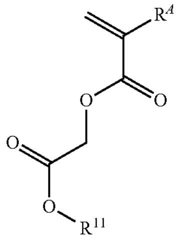

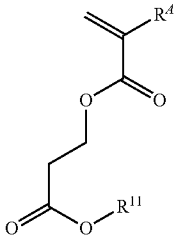

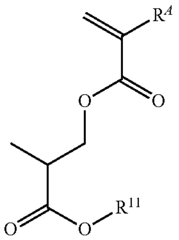

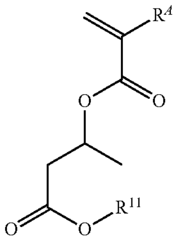

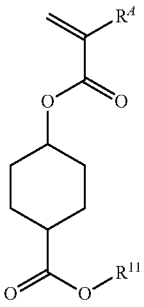

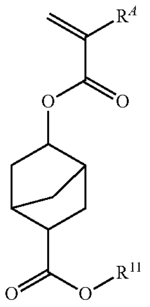

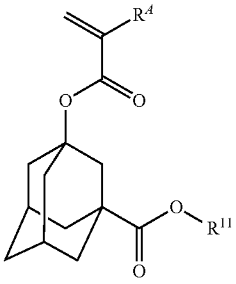

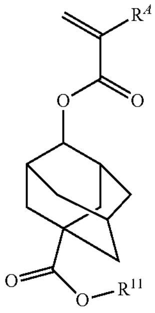

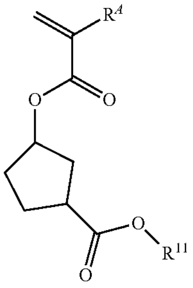

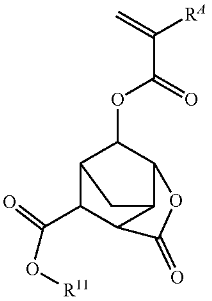

-continued

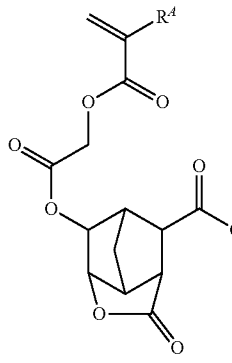

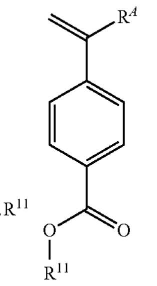

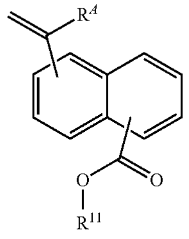

Examples of a monomer to give the repeating unit-a2 include those shown below, but are not limited thereto. Incidentally, in the following formulae, $R^A$ and $R^{12}$ are the same as above.

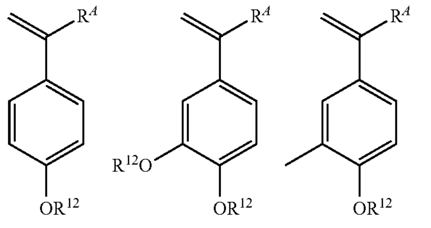

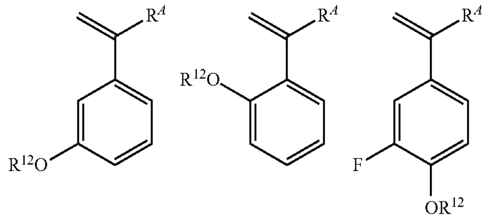

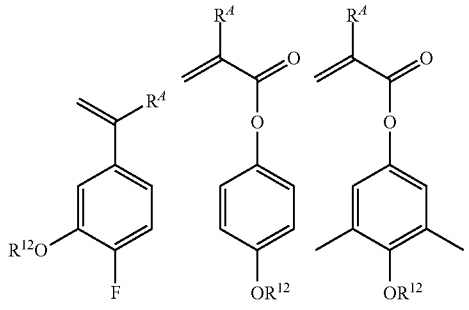

-continued

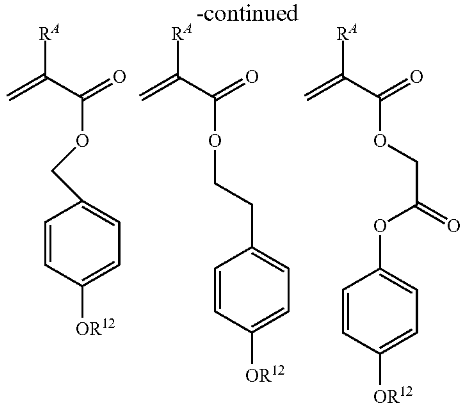

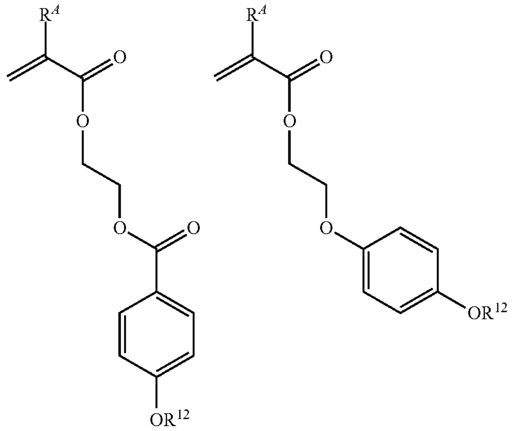

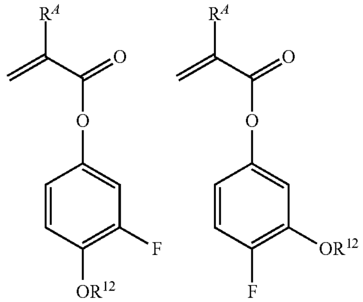

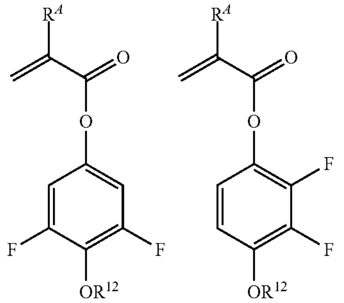

In the general formulae (a1) and (a2), examples of the acid-labile groups represented by $R^{11}$ and $R^{12}$ include those disclosed in JP 2013-80033 A and JP 2013-83821 A.

Typical examples of the acid-labile groups include those represented by the following formulae (AL-1) to (AL-3).

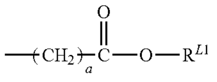

(AL-1)

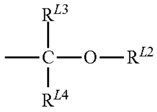

(AL-2)

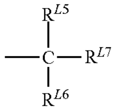

(AL-3)

In the general formulae (AL-1) and (AL-2), $R^{L1}$ and $R^{L2}$ each independently represent a monovalent hydrocarbon group having 1 to 40 carbon atoms, and optionally contain a heteroatom such as an oxygen atom, a sulfur atom, a nitrogen atom, or a fluorine atom. The monovalent hydrocarbon group may be linear, branched, or cyclic, and is preferably an alkyl group having 1 to 40 carbon atoms, more preferably an alkyl group having 1 to 20 carbon atoms. In the general formula (AL-1), "a" is preferably an integer of 0 to 10, preferably an integer of 1 to 5.

In the general formula (AL-2), $R^{L3}$ and $R^{L4}$ each independently represent a hydrogen atom or a monovalent hydrocarbon group having 1 to 20 carbon atoms, and optionally contain a heteroatom such as an oxygen atom, a sulfur atom, a nitrogen atom, or a fluorine atom. The monovalent hydrocarbon group may be linear, branched, or cyclic, and is preferably an alkyl group having 1 to 20 carbon atoms. Furthermore, any two of $R^{L2}$, $R^{L3}$, and $R^{L4}$ may bond with each other to form a ring having 3 to 20 carbon atoms together with a carbon atom bonded therewith, or together with the carbon atom and an oxygen atom. As the ring, a ring having 4 to 16 carbon atoms is preferable, and an aliphatic ring is particularly preferable.

In the general formula (AL-3), $R^{L5}$, $R^{L6}$, and $R^{L7}$ each independently represent a monovalent hydrocarbon group having 1 to 20 carbon atoms, and optionally contain a heteroatom such as an oxygen atom, a sulfur atom, a nitrogen atom, or a fluorine atom. The monovalent hydrocarbon group may be linear, branched, or cyclic, and is preferably an alkyl group having 1 to 20 carbon atoms. Furthermore, any two of $R^{L5}$, $R^{L6}$, and $R^{L7}$ may bond with each other to form a ring having 3 to 20 carbon atoms together with a carbon atom bonded therewith. As the ring, a ring having 4 to 16 carbon atoms is preferable, and an aliphatic ring is particularly preferable.

The base polymer may further contain, as an adhesive group, a repeating unit-b containing a phenolic hydroxy group. Examples of a monomer to give the repeating unit-b include those shown below, but are not limited thereto. Incidentally, in the following formulae, $R^A$ is as defined above.

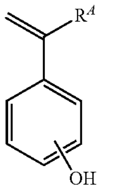
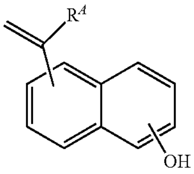
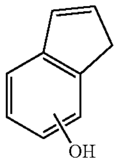

-continued

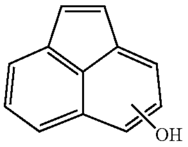
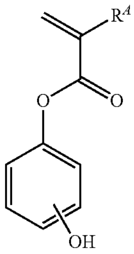
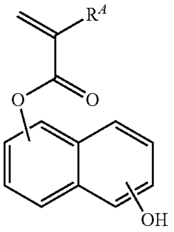

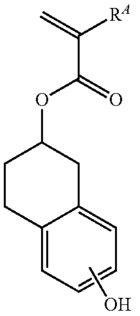
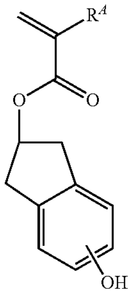
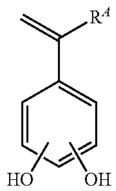

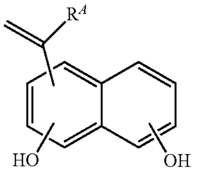
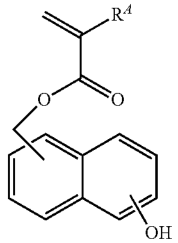

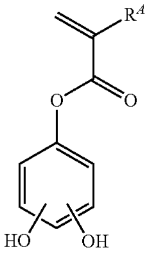
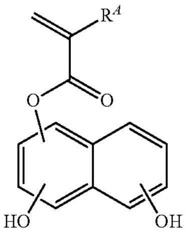

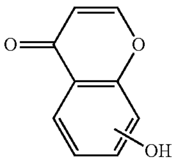
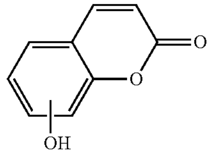

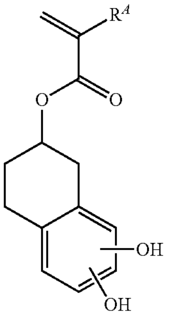
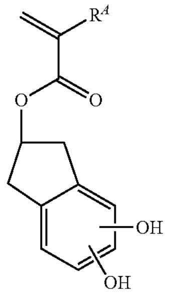
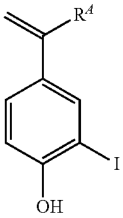

-continued

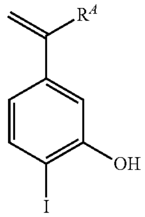
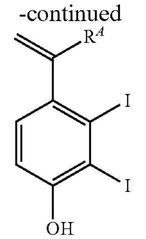
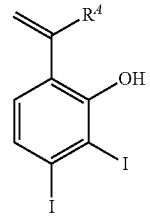
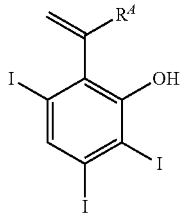
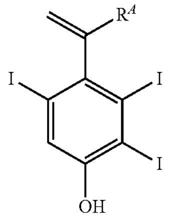
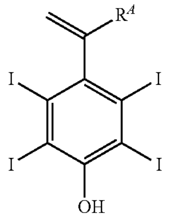
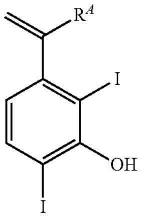
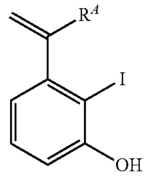
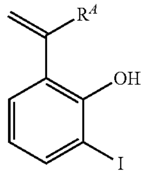
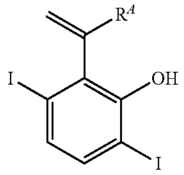
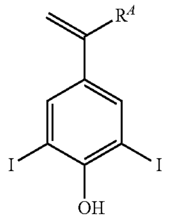
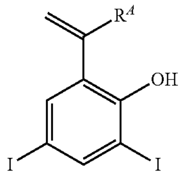
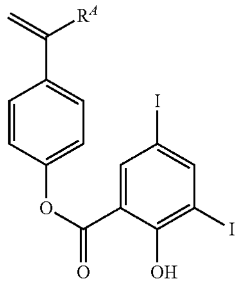
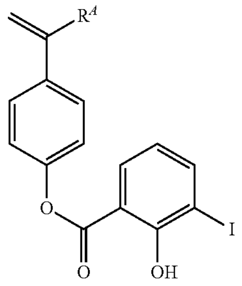
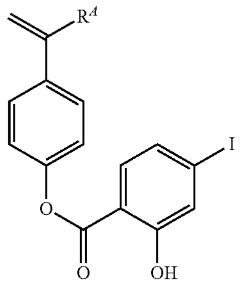
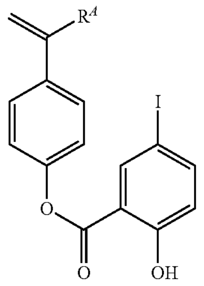

-continued

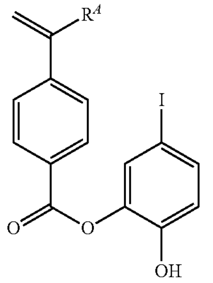
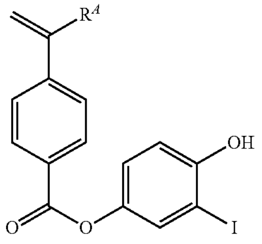
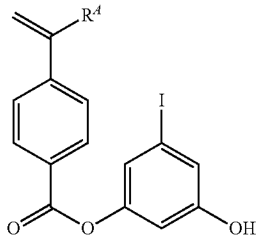

The base polymer may further contain, as a different adhesive group, a repeating unit-c containing a group other than a phenolic hydroxy group, that is, a hydroxy group, a lactone ring, an ether bond, an ester bond, a carbonyl group, a cyano group, or a carboxy group. Examples of a monomer to give the repeating unit-c include those shown below, but are not limited thereto. Incidentally, in the following formulae, $R^A$ is as defined above.

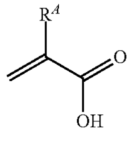
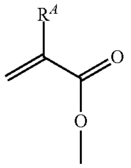
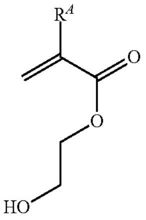
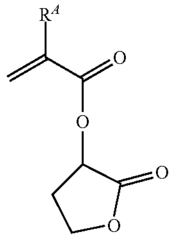
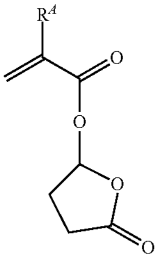
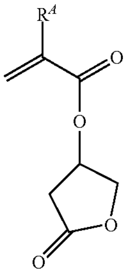
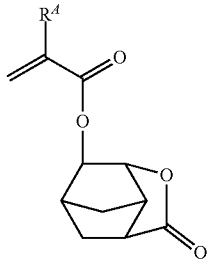
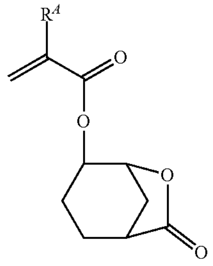

-continued
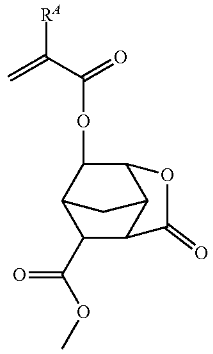
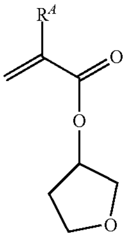
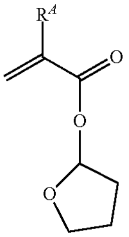
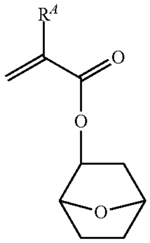
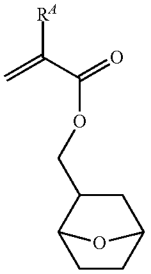
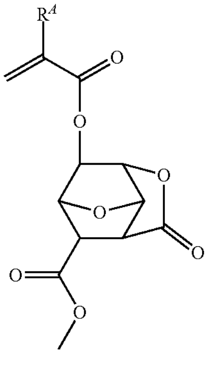
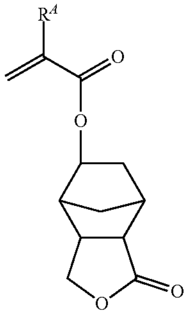
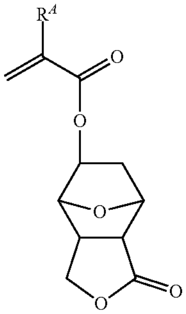
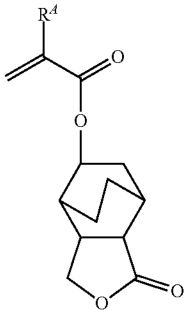
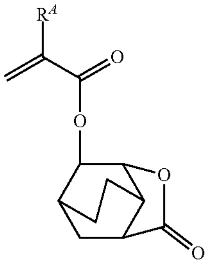
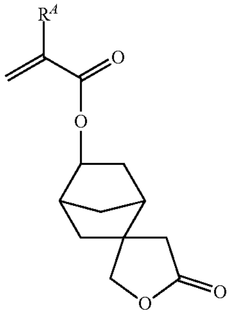
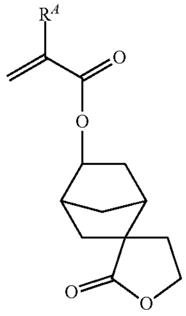
-continued
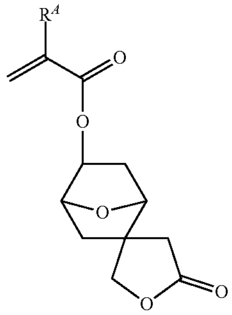
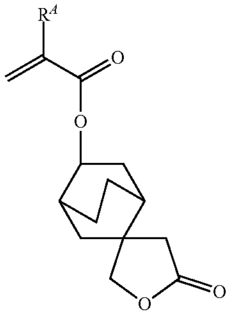
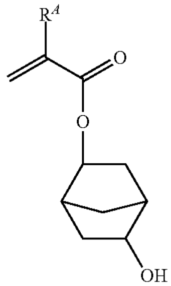
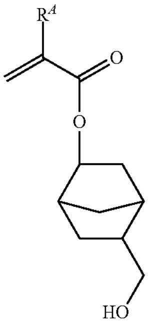
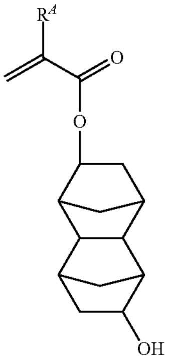
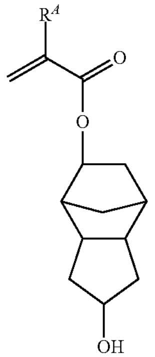
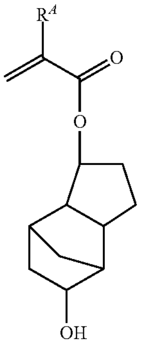
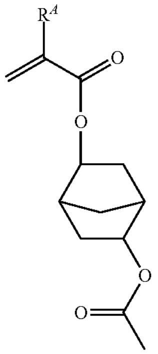
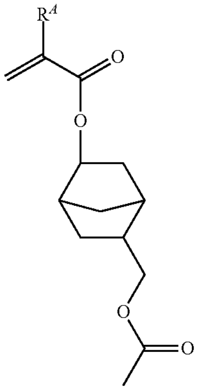
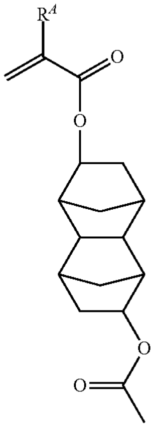
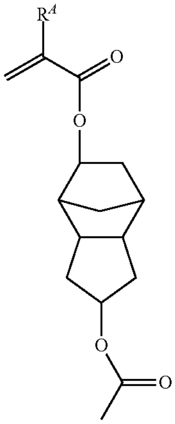

-continued
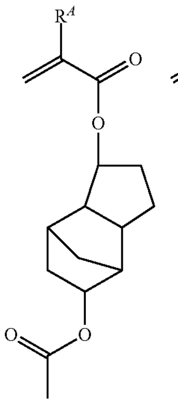
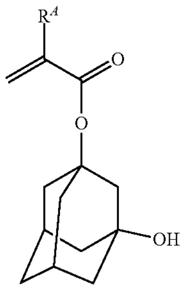
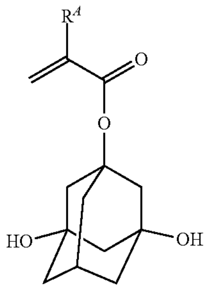
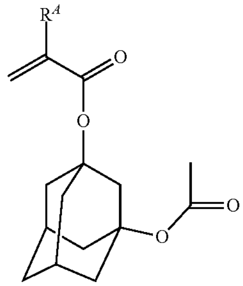
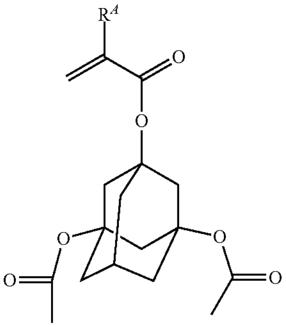
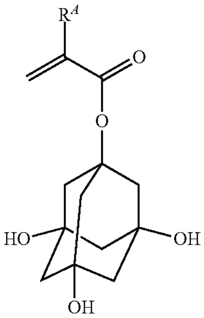
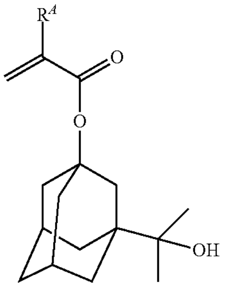
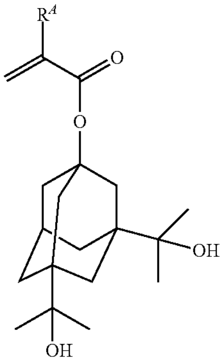
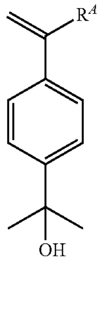
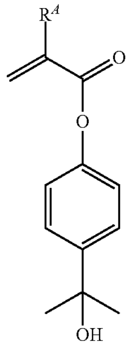
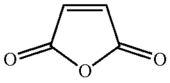
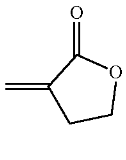
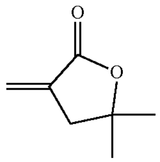
-continued
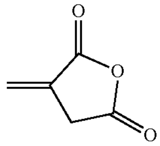
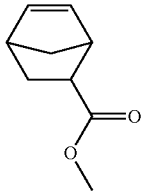
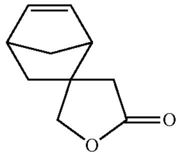
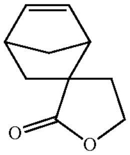
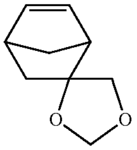
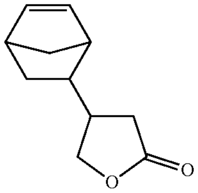
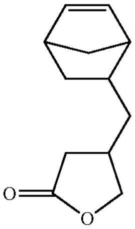
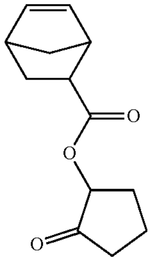
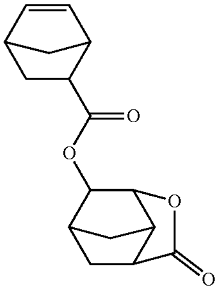
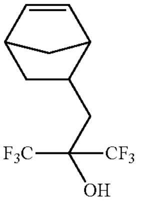
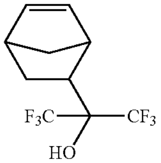
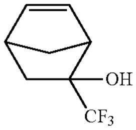
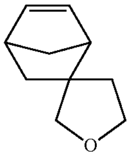
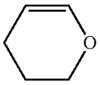
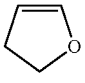
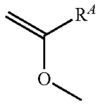
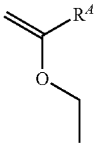
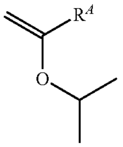
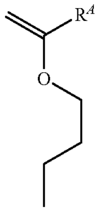
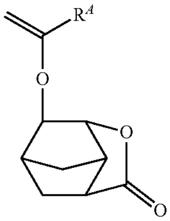
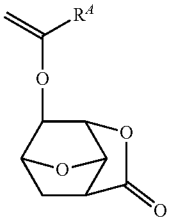
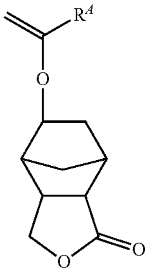
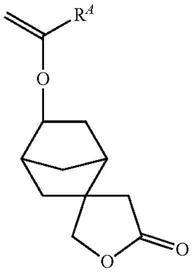

-continued
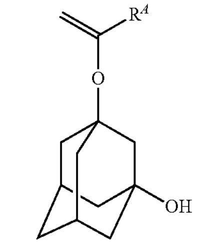
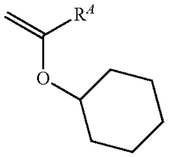
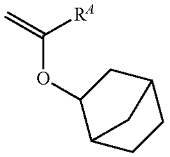
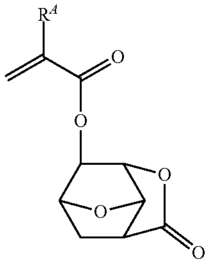
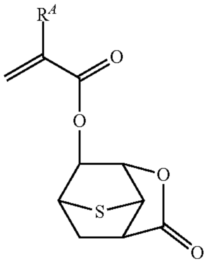
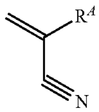
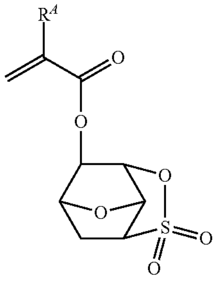
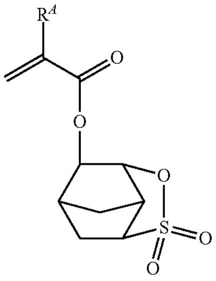
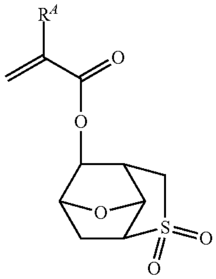
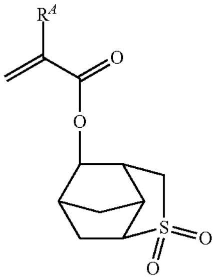
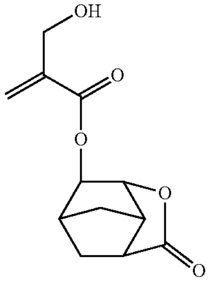
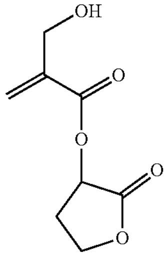
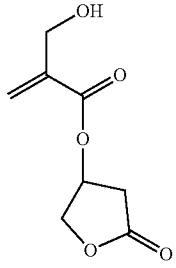
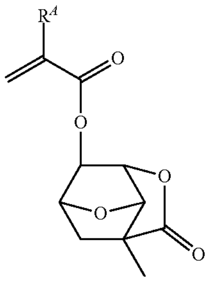
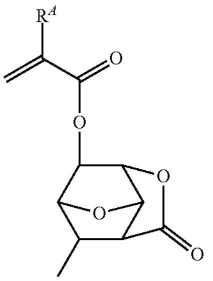
-continued
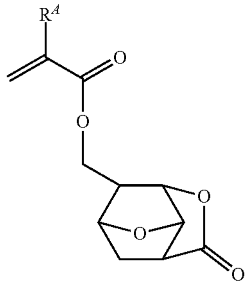
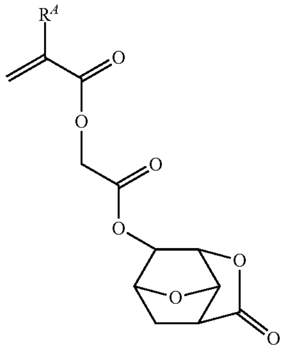
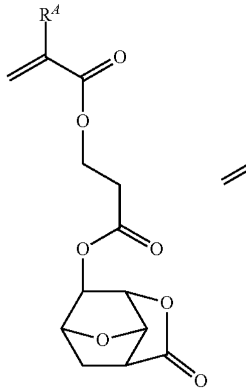
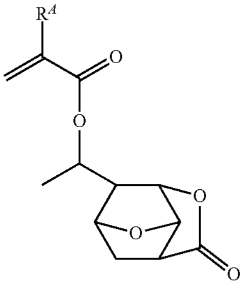
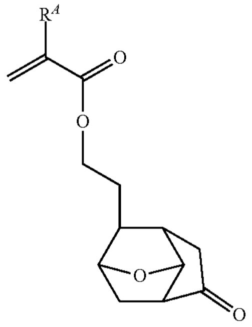
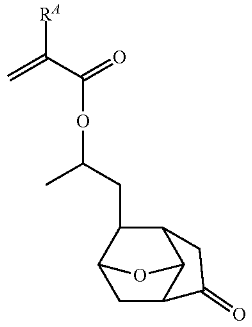
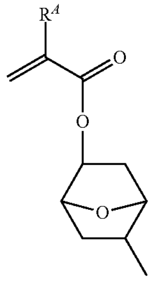
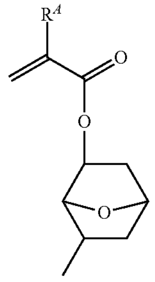
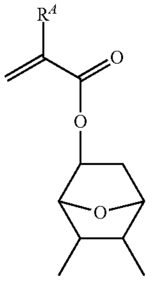
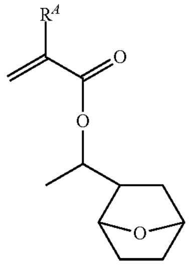
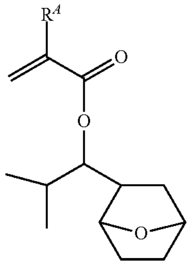
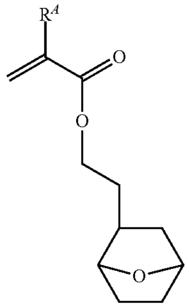

-continued
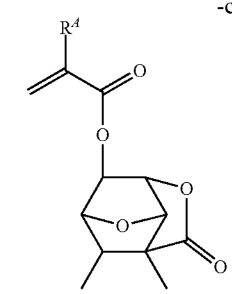
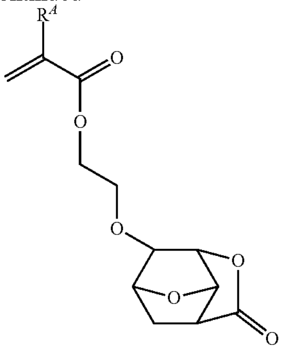
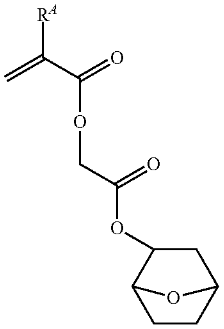
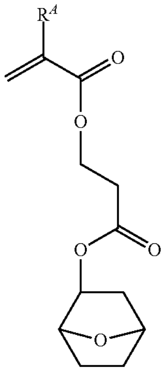
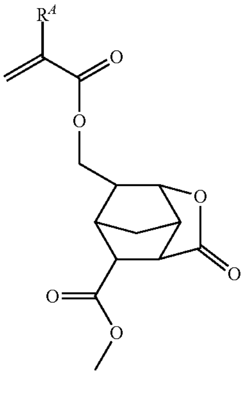
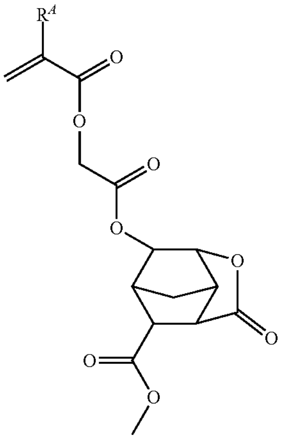
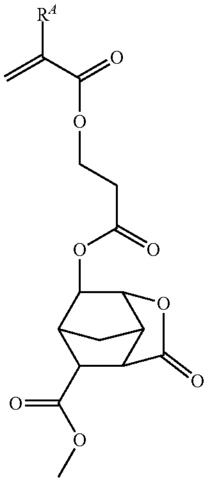
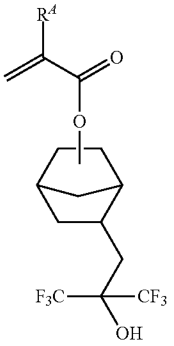
-continued
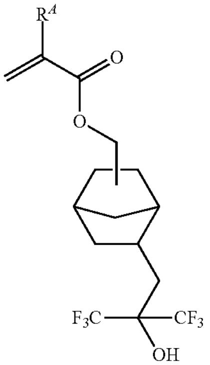
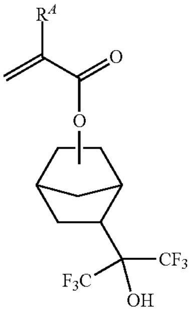
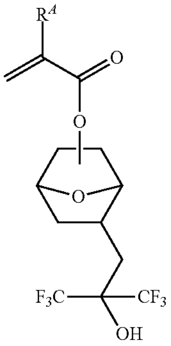
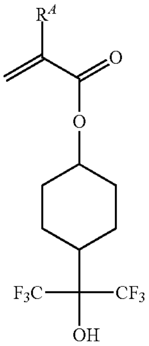
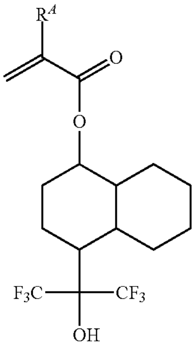
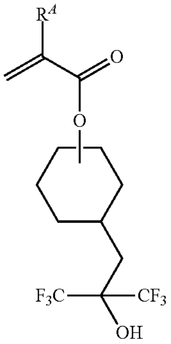
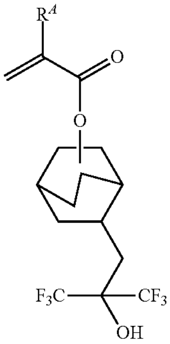
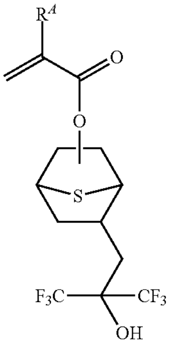
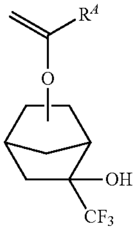
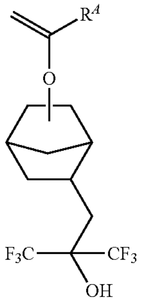
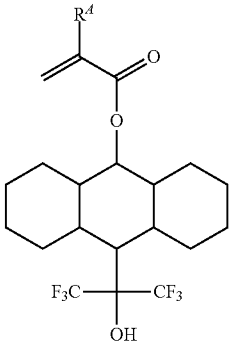

-continued
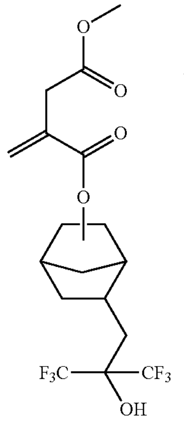
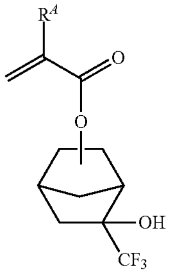
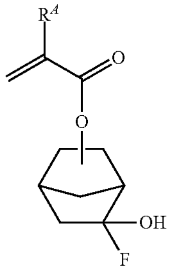
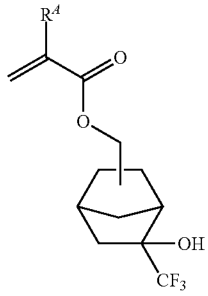
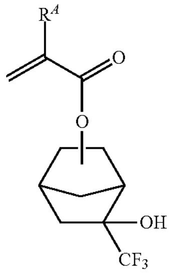
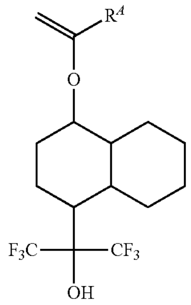
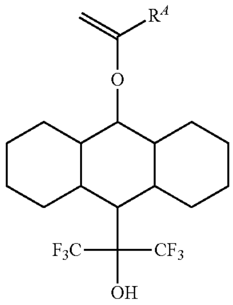
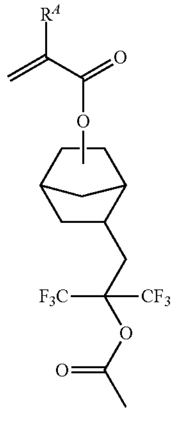
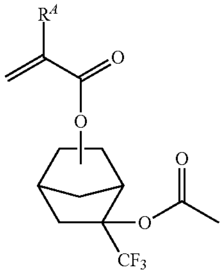
-continued
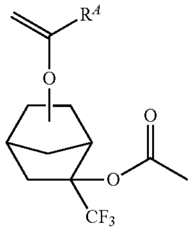
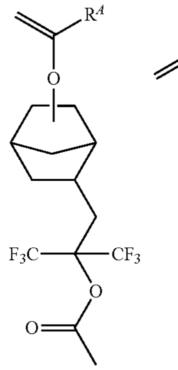
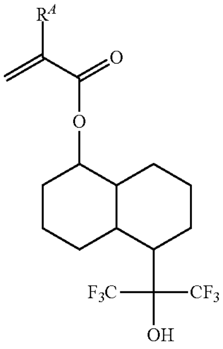
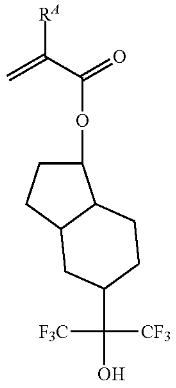
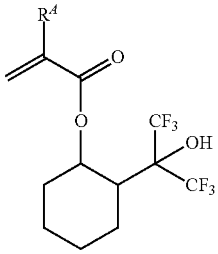
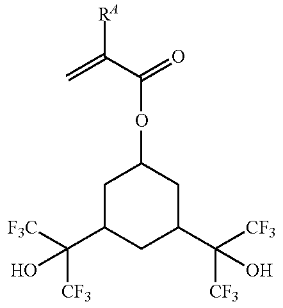
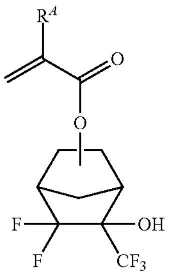
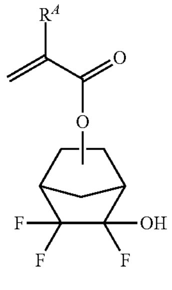
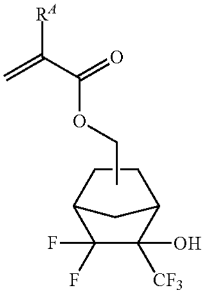
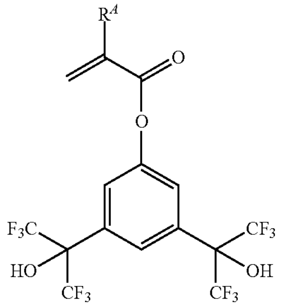
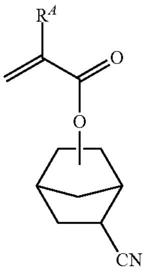

-continued
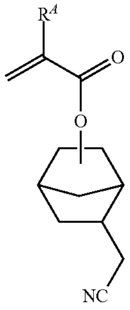
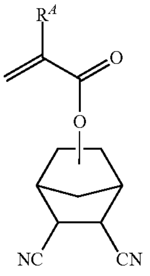
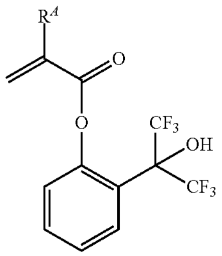
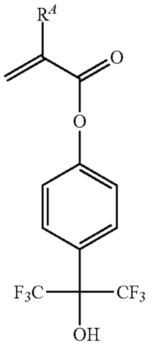
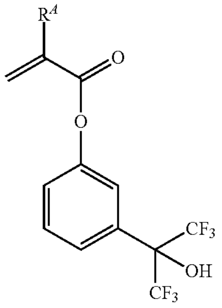
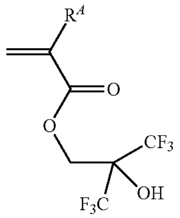
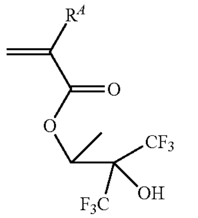
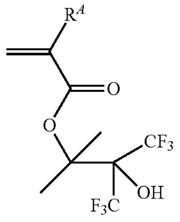
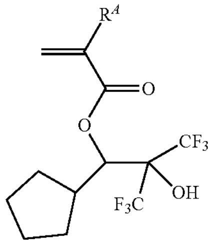
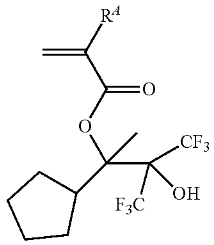
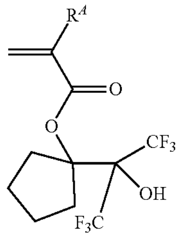
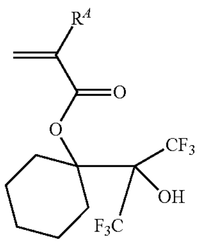
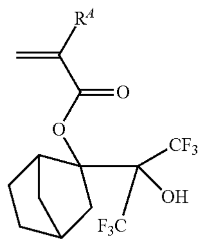
-continued
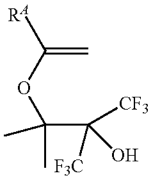
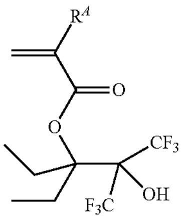
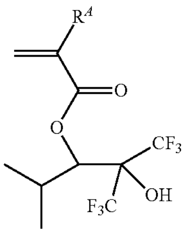
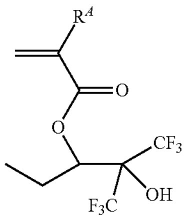
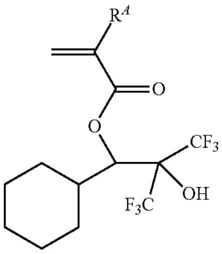
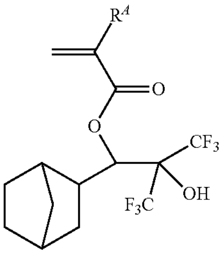
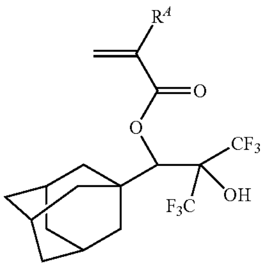
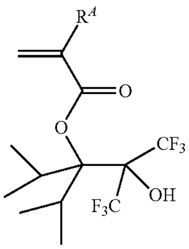
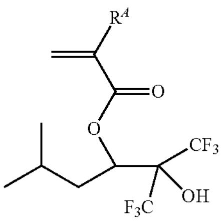
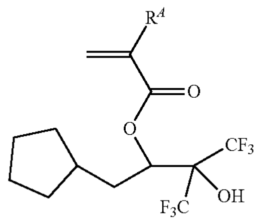
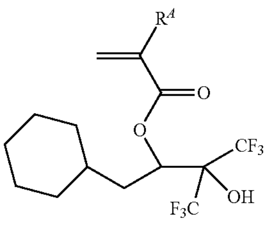
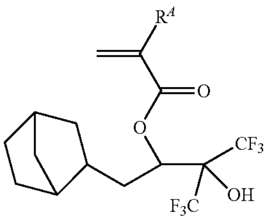

-continued
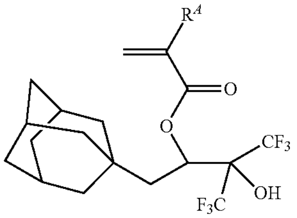
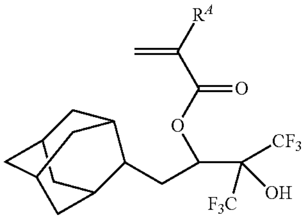
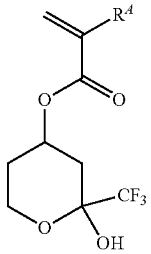
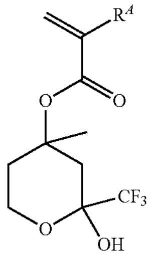
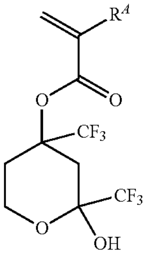
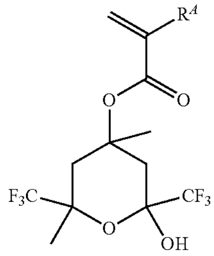
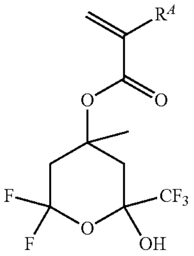
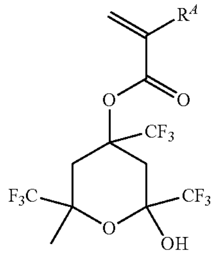
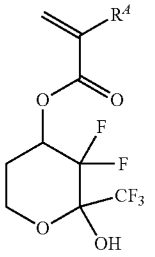
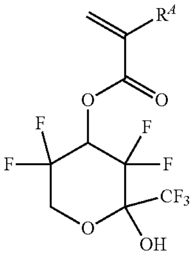
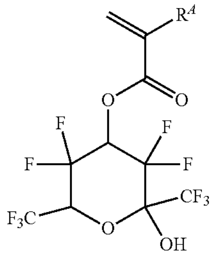
-continued
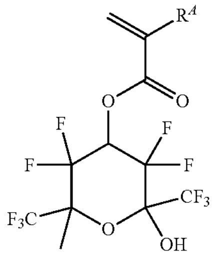
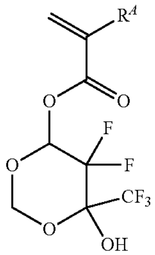
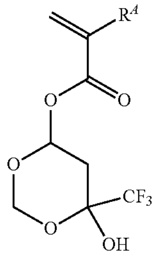
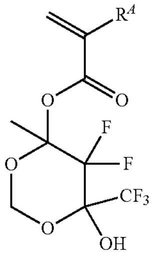
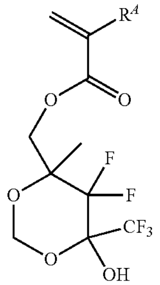
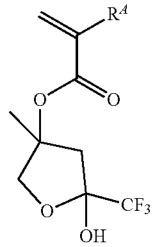
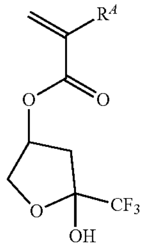
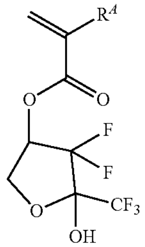
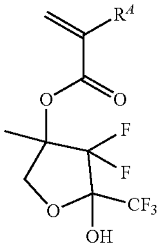
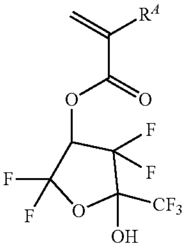
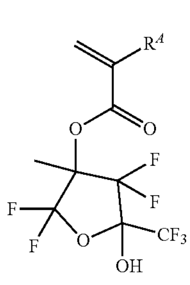
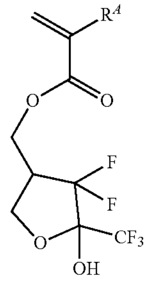
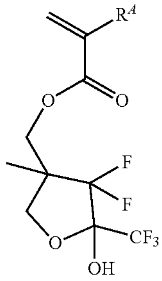
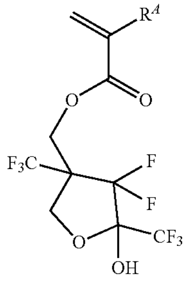
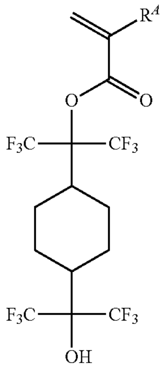

-continued
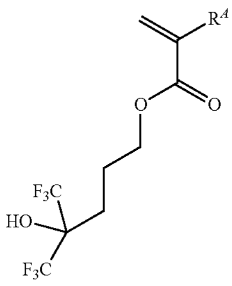
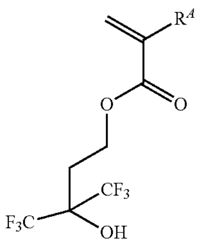
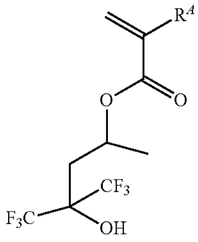
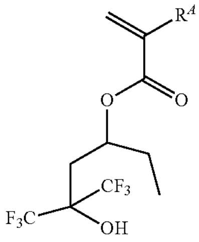
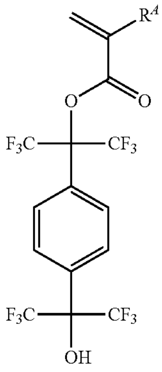
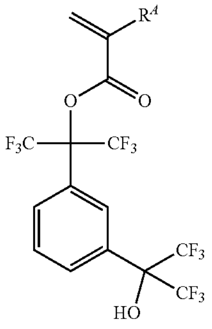
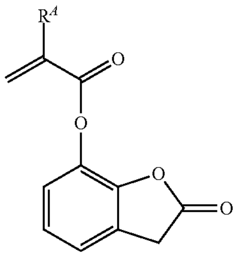
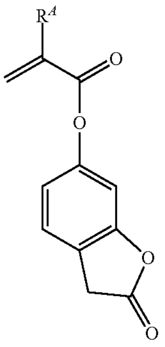
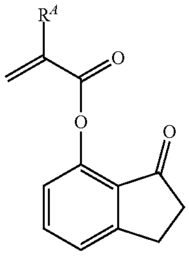
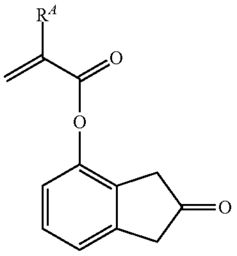
-continued
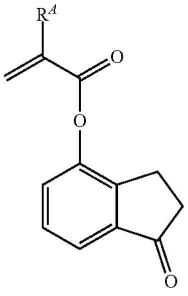
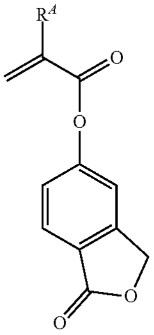
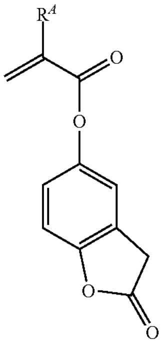
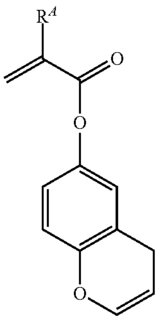
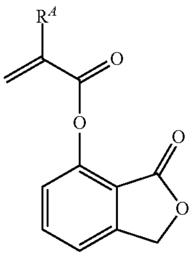
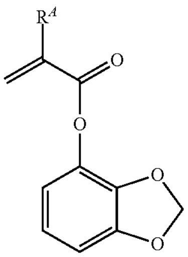
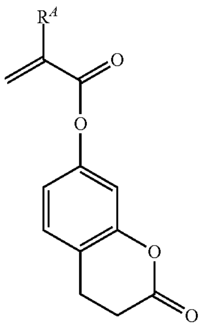
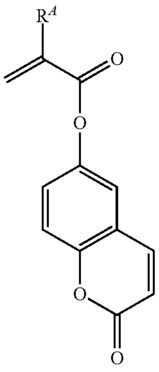
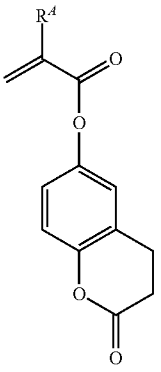
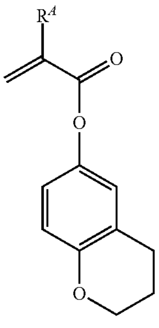

-continued
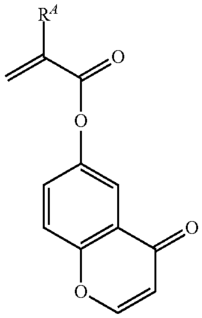
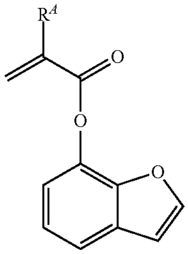
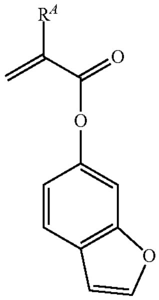
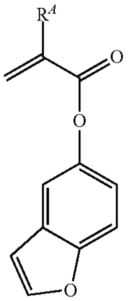
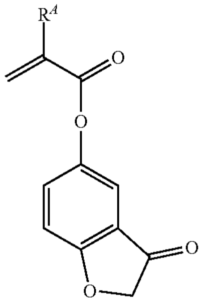
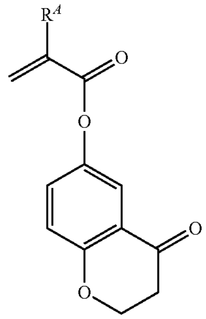
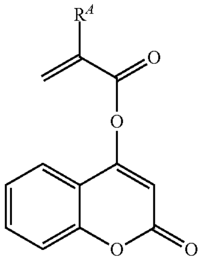
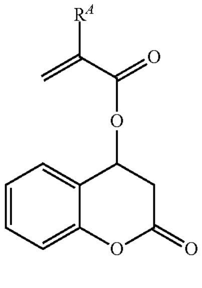
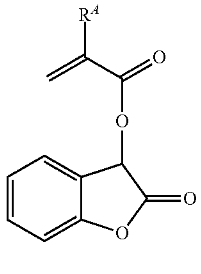
-continued
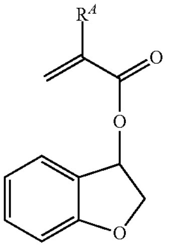
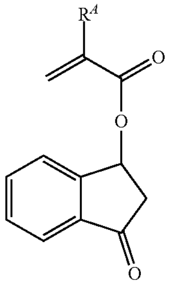
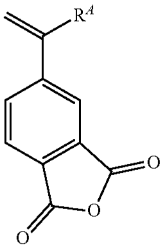
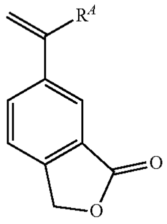
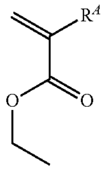
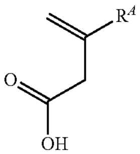
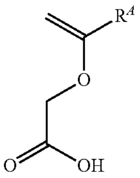
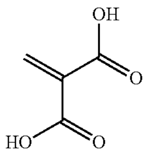
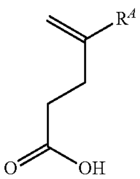
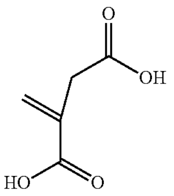
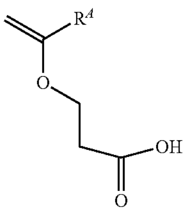
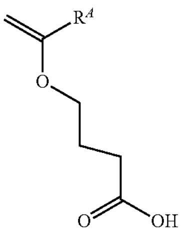
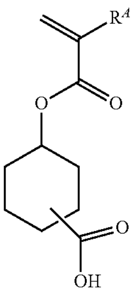
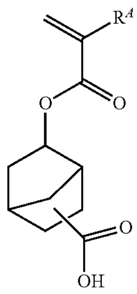
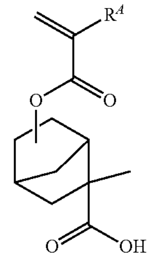
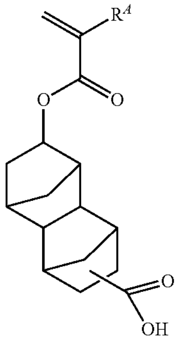

-continued

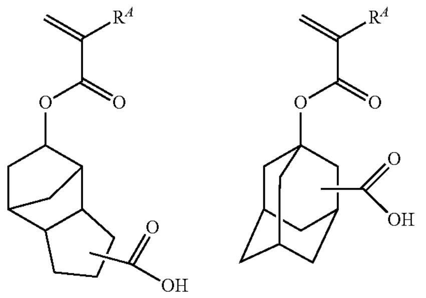

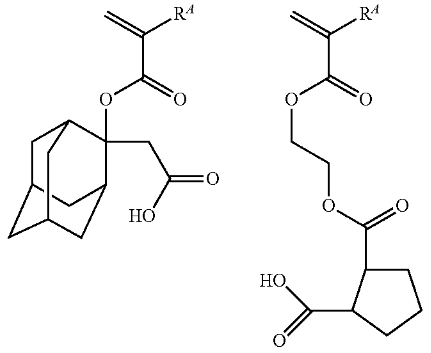

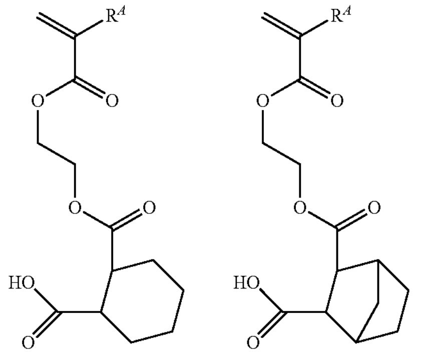

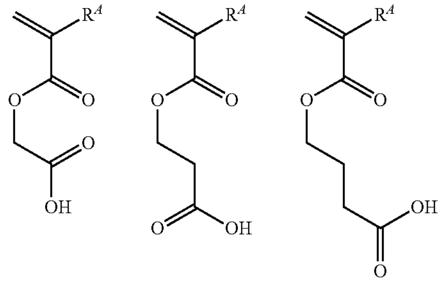

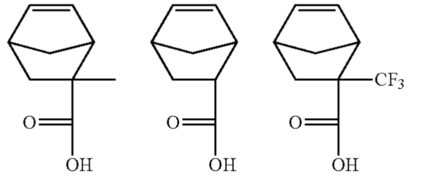

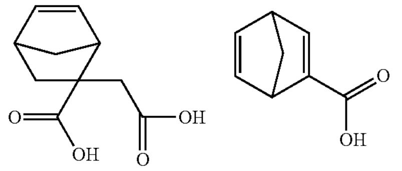

-continued

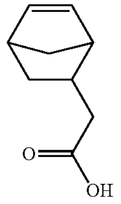

The base polymer may further contain a repeating unit-d derived from indene, benzofuran, benzothiophene, acenaphthylene, chromone, coumarin, norbornadiene, or a derivative thereof. Examples of a monomer to give the repeating unit-d include those shown below, but are not limited thereto.

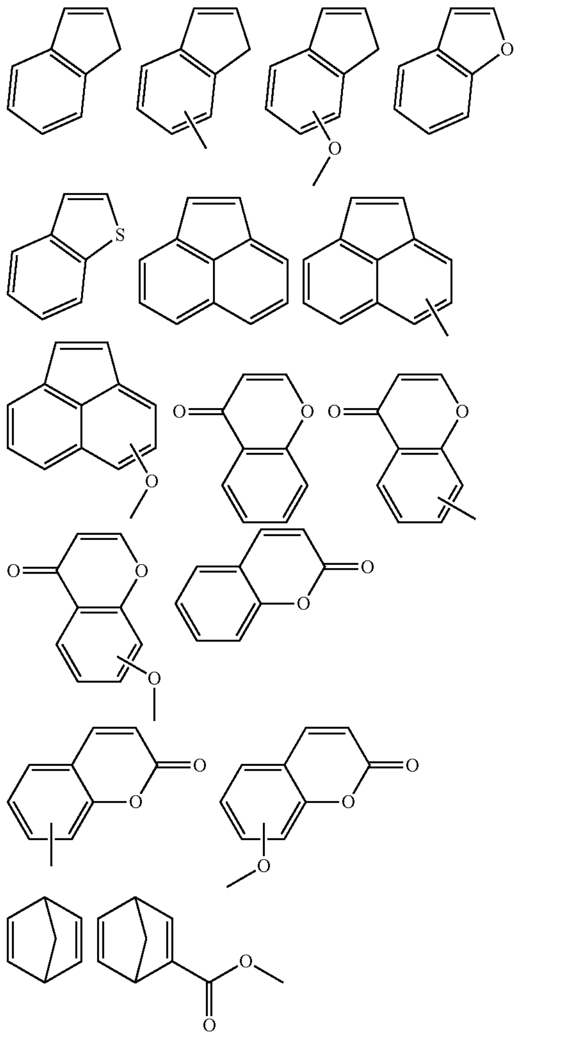

The base polymer may further contain a repeating unit-e derived from styrene, vinylnaphthalene, vinylanthracene, vinylpyrene, methyleneindane, vinylpyridine, or vinylcarbazole.

The base polymer may further contain a repeating unit-f derived from an onium salt including a polymerizable unsaturated bond. Preferable examples of the repeating unit-f include a repeating unit represented by the following general formula (f1) (hereinafter, also referred to as a repeating unit-f1), a repeating unit represented by the following general formula (f2) (hereinafter, also referred to as a repeating unit-f2), and a repeating unit represented by the following general formula (f3) (hereinafter, also referred to as a repeating unit-f3). Note that one of the repeating units-f1 to -f3 may be used, or a combination of two or more kinds thereof may be used.

(f1)

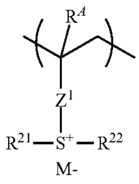

(f2)

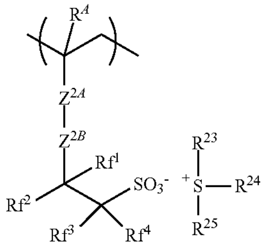

(f3)

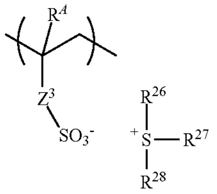

In the general formulae (f1) to (f3), each $R^A$ independently represents a hydrogen atom or a methyl group. $Z^1$ represents a single bond, a phenylene group, a naphthylene group, —$Z^{11}$—, —O—$Z^{11}$—, —C(═O)—O—$Z^{11}$—, or —C(═O)—NH—$Z^{11}$—. $Z^{11}$ represents an alkanediyl group having 1 to 6 carbon atoms, an alkenediyl group having 2 to 6 carbon atoms, or a hydrocarbon group having 1 to 20 carbon atoms and optionally containing a phenylene group and optionally contains a carbonyl group, an ester bond, an ether bond, or a hydroxy group. $Z^{2A}$ represents a single bond or an ester bond. $Z^{2B}$ represents a single bond or a divalent group having 1 to 18 carbon atoms and optionally contains an ester bond, an ether bond, a lactone ring, a bromine atom, or an iodine atom. $Z^3$ represents a single bond, a methylene group, an ethylene group, a phenylene group, a fluorinated phenylene group, a phenylene group substituted with a trifluoromethyl group, —$Z^{31}$—, —O—$Z^{31}$—, —C(═O)—O—$Z^{31}$—, or —C(═O)—NH—$Z^{31}$—. $Z^{31}$ represents an alkanediyl group having 1 to 15 carbon atoms, an alkenediyl group having 2 to 15 carbon atoms, or a group containing a phenylene group and optionally contains a carbonyl group, an ester bond, an ether bond, a halogen atom, or a hydroxy group. $Rf^1$ to $Rf^4$ each independently represent a hydrogen atom, a fluorine atom, an oxygen atom, or a trifluoromethyl group, provided that at least one is a fluorine atom, and that when $Rf^1$ and $Rf^2$ are respectively an oxygen atom, $Rf^1$ and $Rf^2$ are a single oxygen atom bonded to a single carbon atom to form a carbonyl group.

In the general formulae (f1) to (f3), $R^{21}$ to $R^{28}$ each independently represent a monovalent hydrocarbon group having 1 to 25 carbon atoms and optionally containing a heteroatom. The monovalent hydrocarbon group may be linear, branched, or cyclic, and specific examples thereof include an alkyl group having 1 to 12 carbon atoms, an aryl group having 6 to 12 carbon atoms, an aralkyl group having 7 to 20 carbon atoms, etc. Furthermore, some or all of the hydrogen atoms of these groups may be substituted with an alkyl group having 1 to 10 carbon atoms, a halogen atom, a trifluoromethyl group, a cyano group, a nitro group, a hydroxy group, a mercapto group, an alkoxy group having 1 to 10 carbon atoms, an alkoxycarbonyl group having 2 to 10 carbon atoms, or an acyloxy group having 2 to 10 carbon atoms, and some of the carbon atoms of these groups may be substituted with a carbonyl group, an ether bond, or an ester bond. In addition, any two of $R^{23}$, $R^{24}$, and $R^{25}$ or any two of $R^{26}$, $R^{27}$, and $R^{28}$ are optionally bonded with each other to form a ring with a sulfur atom that is bonded thereto.

In the general formula (f1), $M^-$ represents a non-nucleophilic counter ion. Examples of the non-nucleophilic counter ion include halide ions such as chloride ion and bromide ion; fluoroalkylsulfonate ions such as triflate ion, 1,1,1-trifluoroethanesulfonate ion, and nonafluorobutanesulfonate ion; arylsulfonate ions such as tosylate ion, benzenesulfonate ion, 4-fluorobenzenesulfonate ion, and 1,2,3,4,5-pentafluorobenzenesulfonate ion; alkylsulfonate ions such as mesylate ion and butanesulfonate ion; imide ions such as bis(trifluoromethylsulfonyl)imide ion, bis(perfluoroethylsulfonyl)imide ion, and bis(perfluorobutylsulfonyl)imide ion; and methide ions such as tris(trifluoromethylsulfonyl)methide ion and tris(perfluoroethylsulfonyl)methide ion.

Other examples of the non-nucleophilic counter ion include sulfonate ions having fluorine substituted at α position as shown by the following general formula (f1-1), sulfonate ions having fluorine substituted at α position and having a trifluoromethyl group substituted at β position as shown by the following general formula (f1-2), etc.

$$R^{31}—CF_2—SO_3^- \qquad (f1\text{-}1)$$

(f1-2)

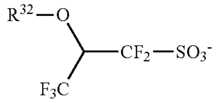

In the general formula (f1-1), $R^{31}$ represents a hydrogen atom, an alkyl group having 1 to 20 carbon atoms, an alkenyl group having 2 to 20 carbon atoms, or an aryl group having 6 to 20 carbon atoms, and optionally contains an ether bond, an ester bond, a carbonyl group, a lactone ring, or a fluorine atom. The alkyl group and alkenyl group may be linear, branched, or cyclic.

In the general formula (f1-2), $R^{32}$ represents a hydrogen atom, an alkyl group having 1 to 30 carbon atoms, an acyl group having 2 to 20 carbon atoms, an alkenyl group having 2 to 20 carbon atoms, an aryl group having 6 to 20 carbon atoms, or an aryloxy group having 6 to 20 carbon atoms, and optionally contains an ether bond, an ester bond, a carbonyl group, or a lactone ring. The alkyl group, acyl group, and alkenyl group may be linear, branched, or cyclic.

Examples of a cation of a monomer to give the repeating unit-f1 include those shown below, but are not limited thereto. Note that in the following formulae, $R^A$ is as defined above.

-continued
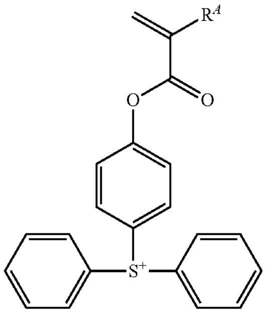
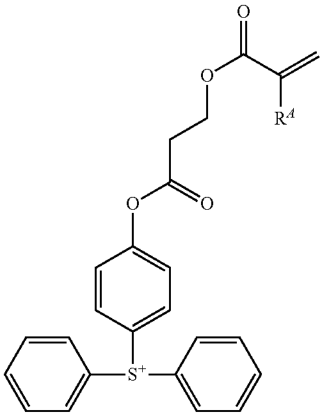
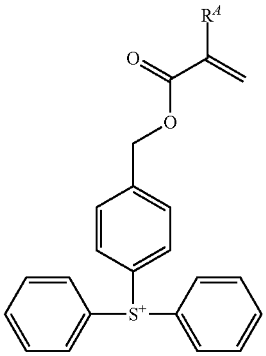
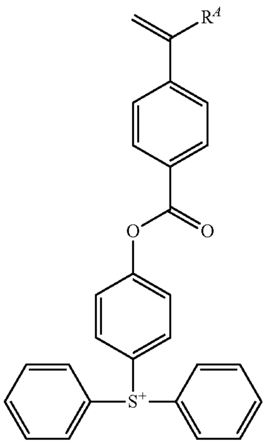
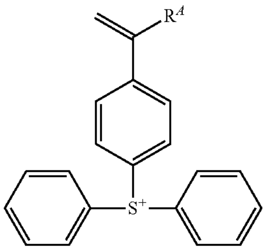
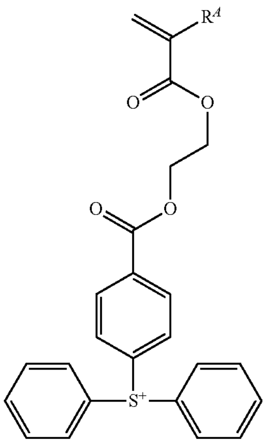
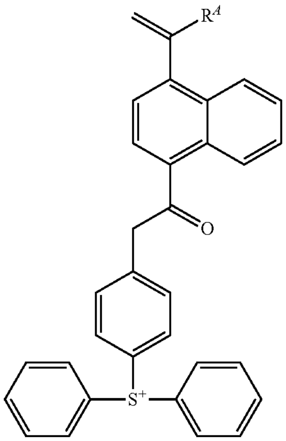
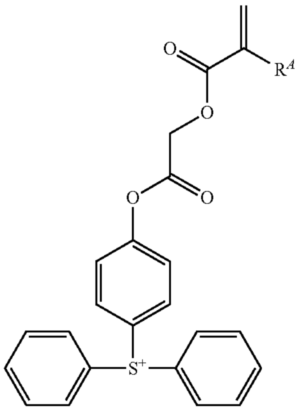

-continued
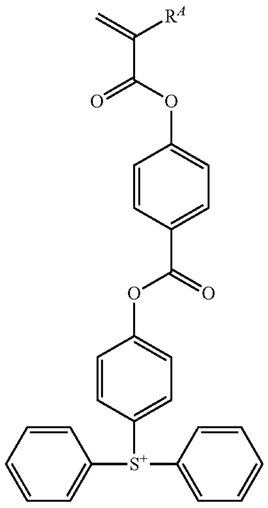
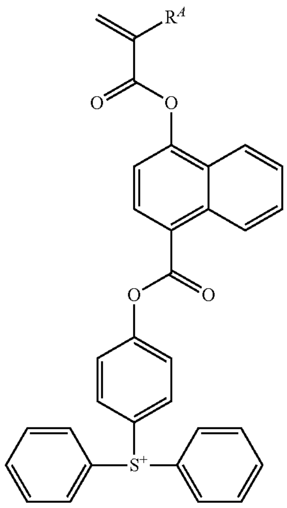
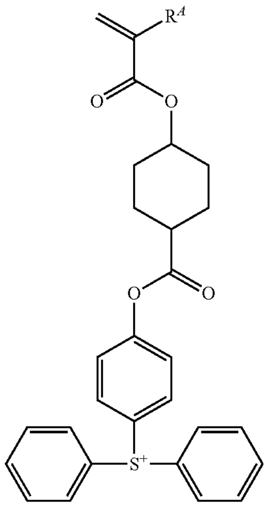
-continued
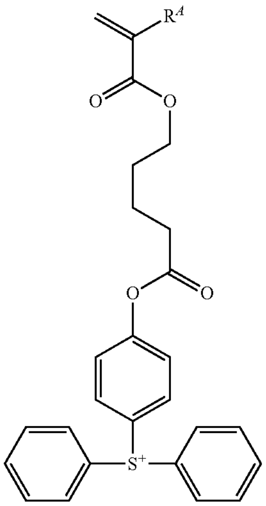
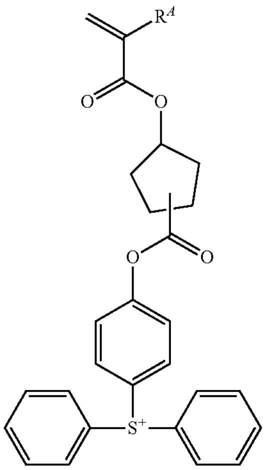
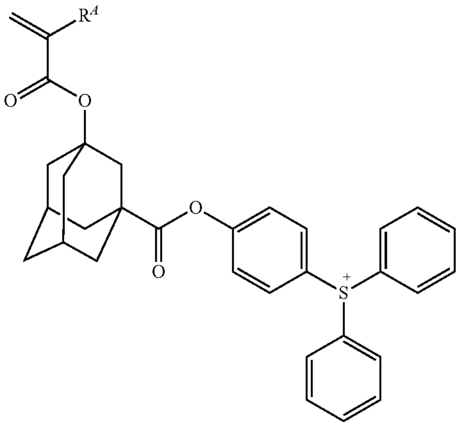

-continued
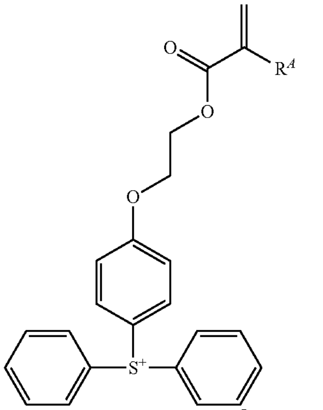
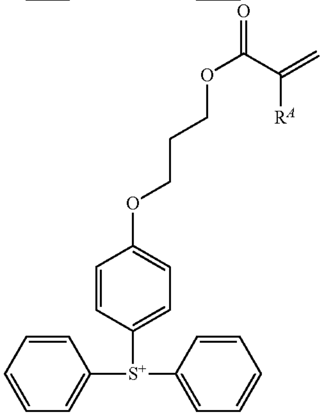
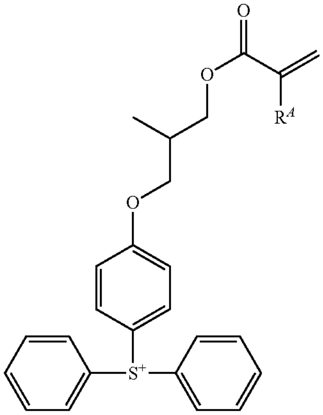
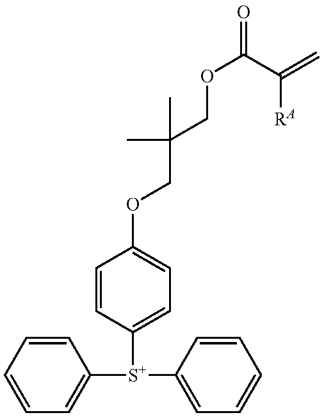
Examples of an anion of a monomer to give the repeating unit-f2 include those shown below, but are not limited thereto. Note that in the following formulae, $R^A$ is as defined above.
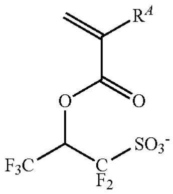
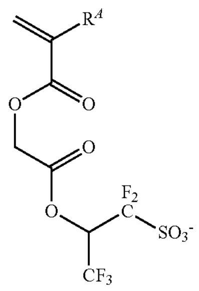
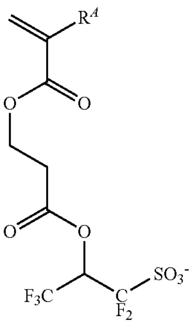
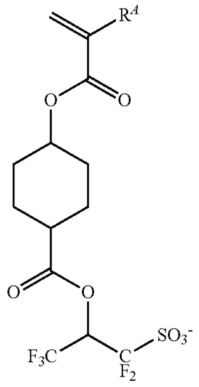
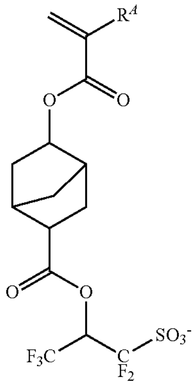
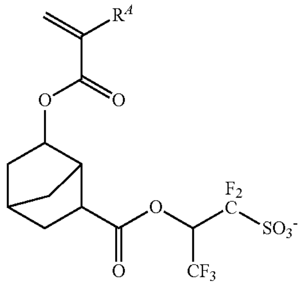
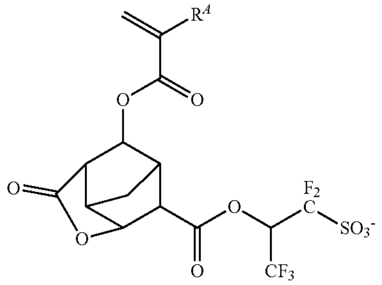
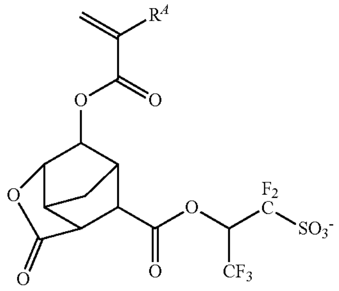

-continued
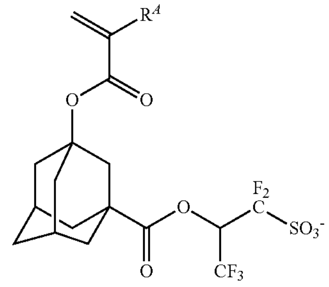
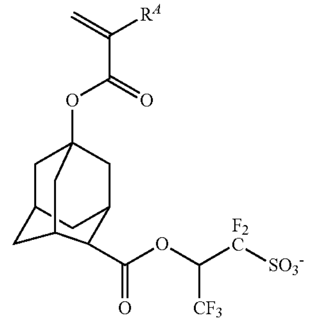
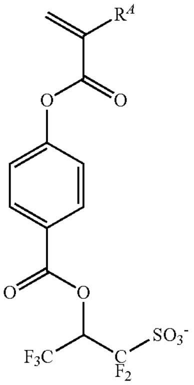
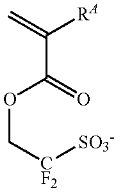
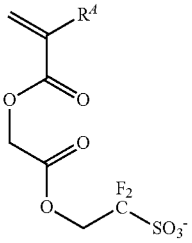
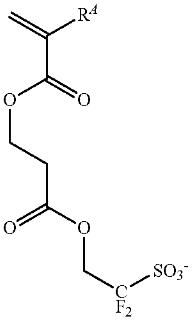
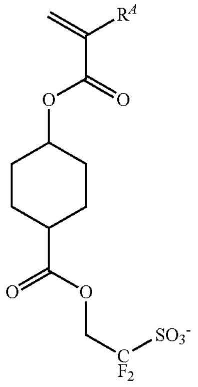
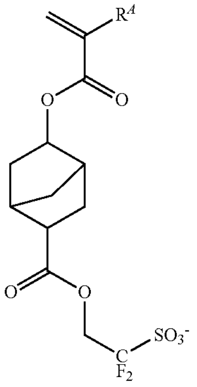
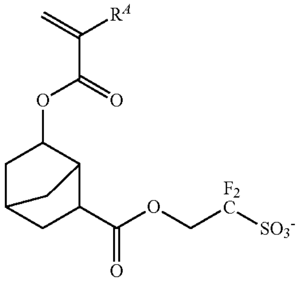
-continued
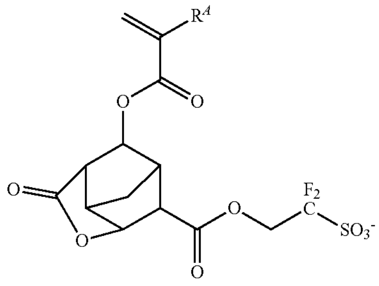
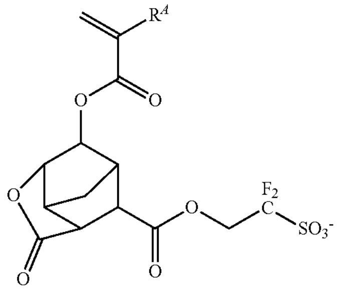
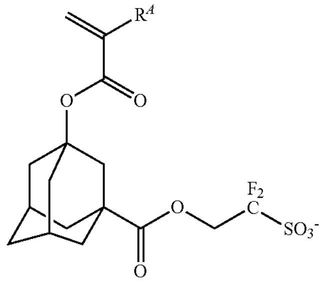
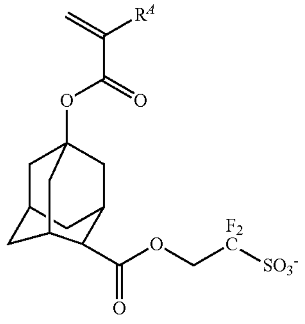
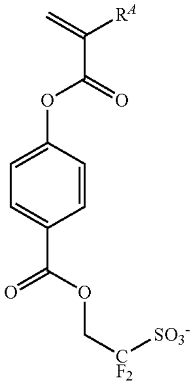
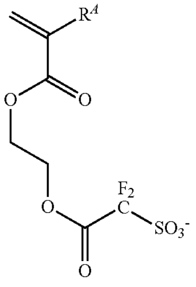
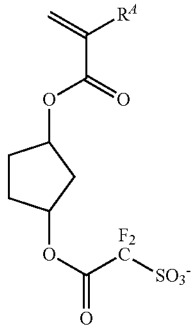

-continued
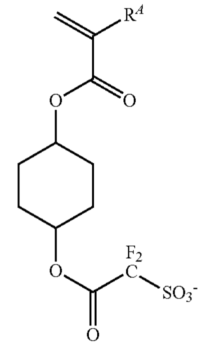
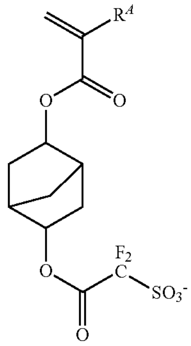
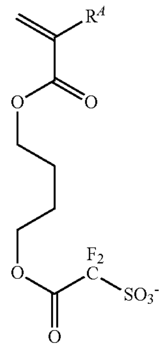
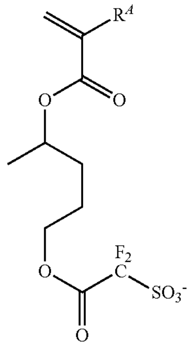
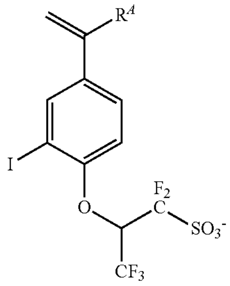
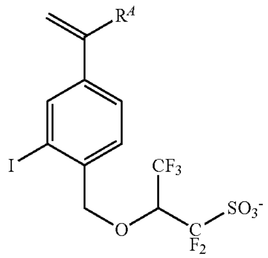
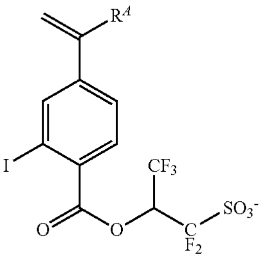
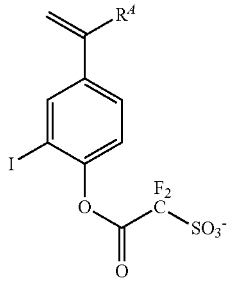
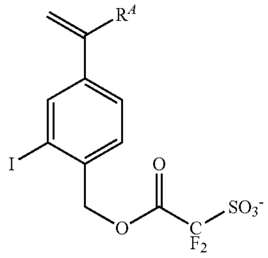
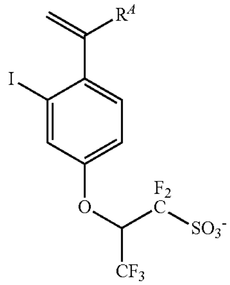
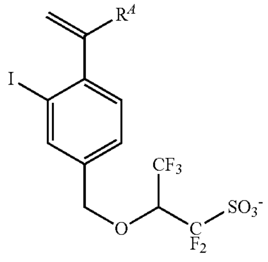
-continued
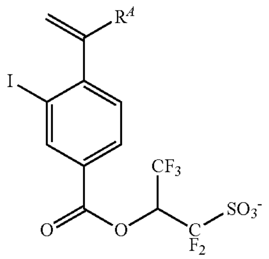
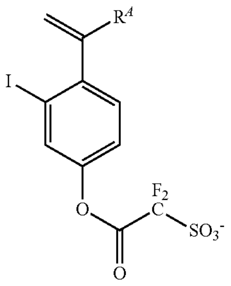
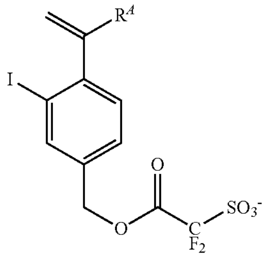
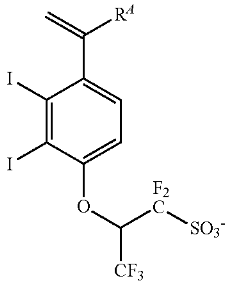
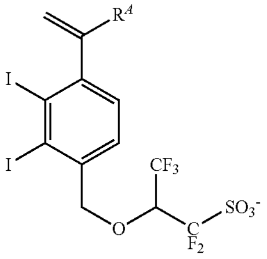
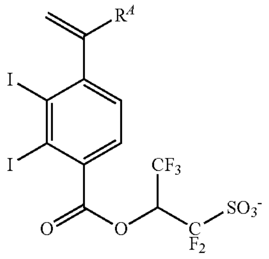
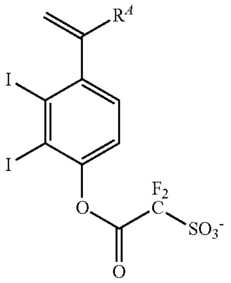
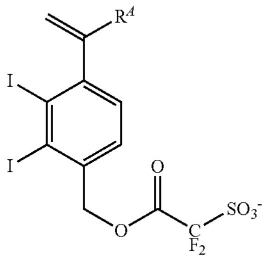
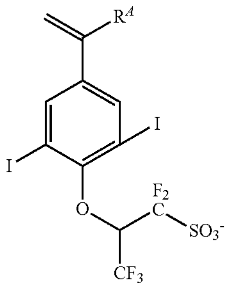
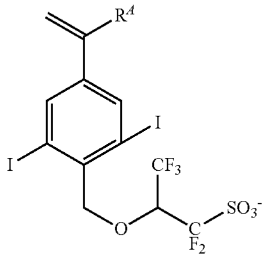
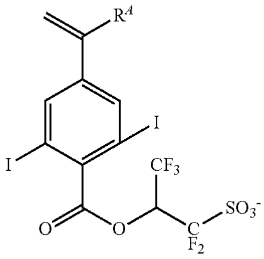

-continued
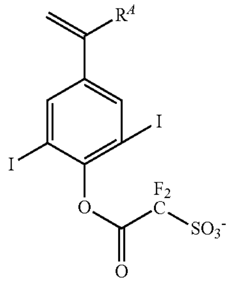
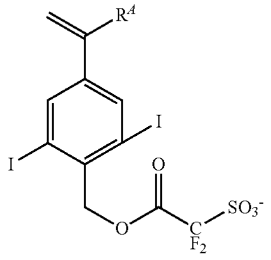
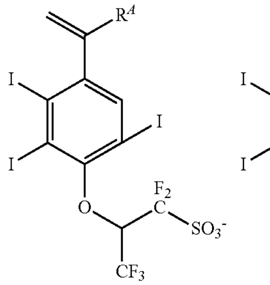
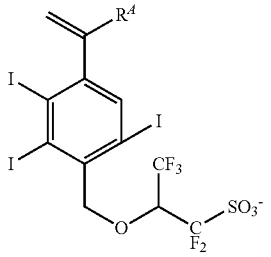
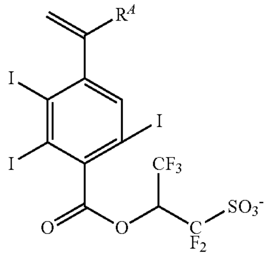
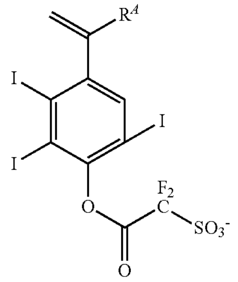
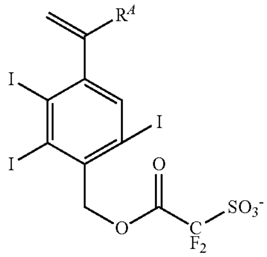
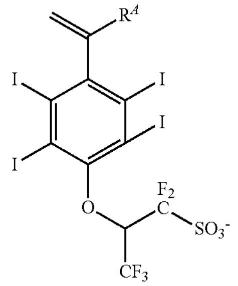
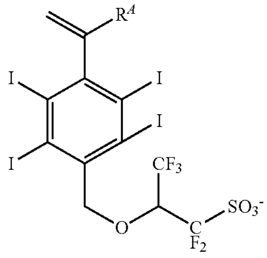
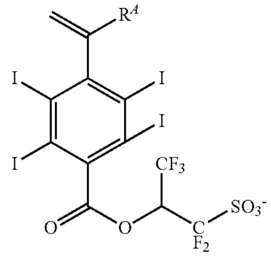
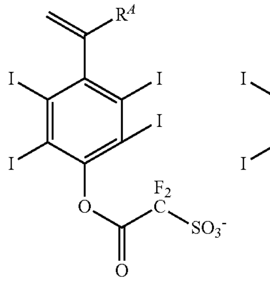
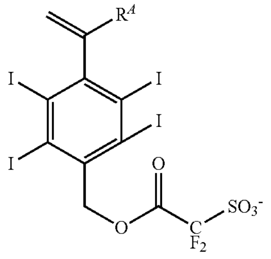
-continued
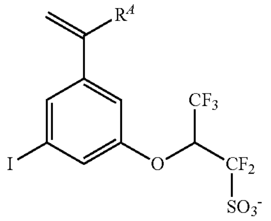
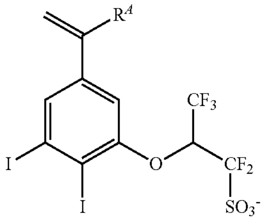
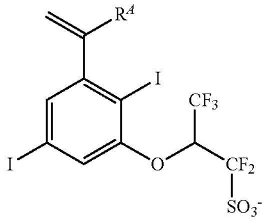
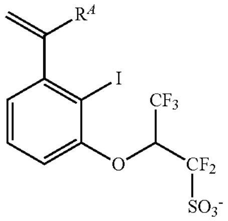
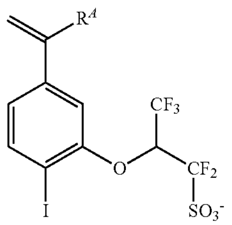
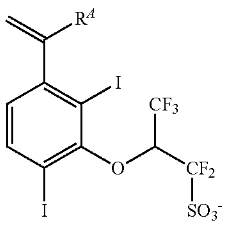
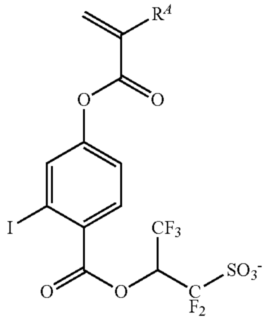
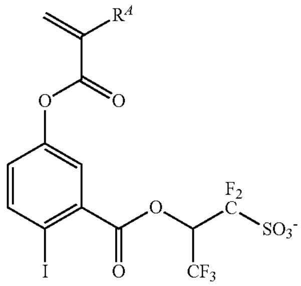
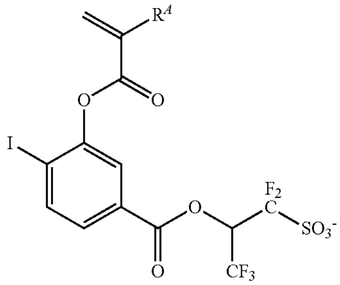

-continued
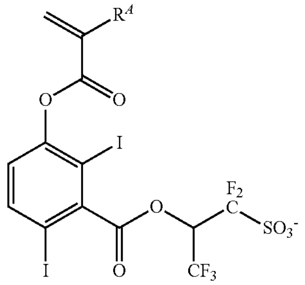
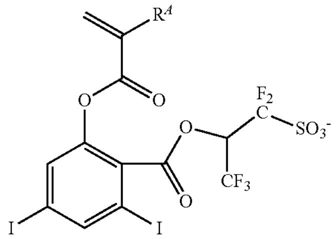
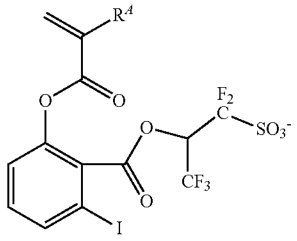
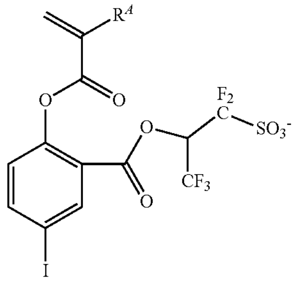
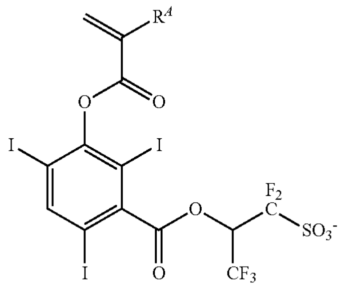
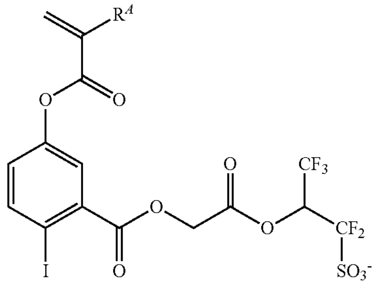
-continued
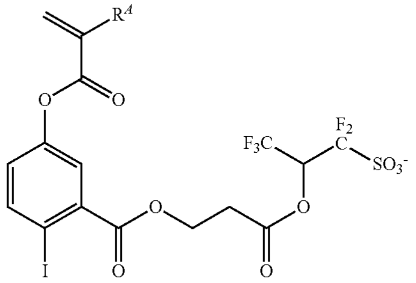
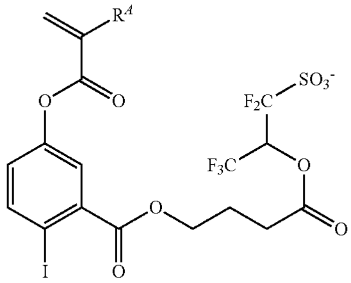
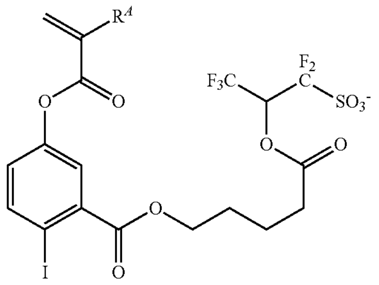
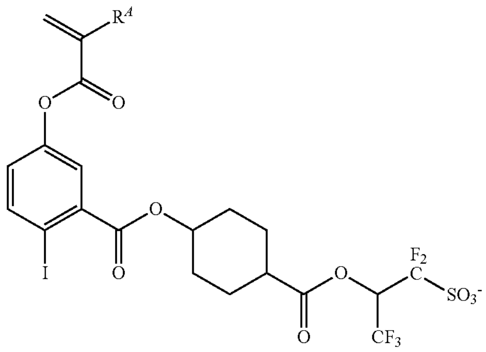
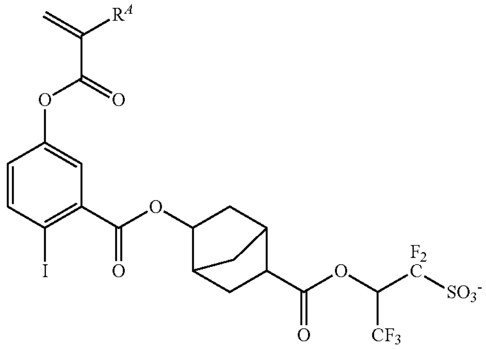

-continued
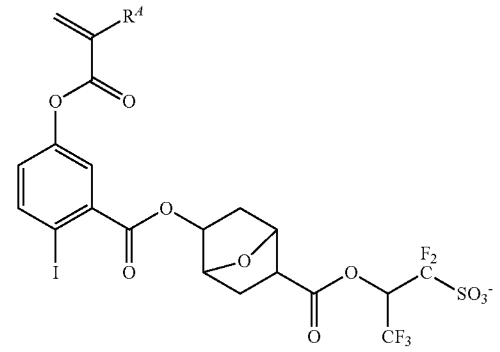
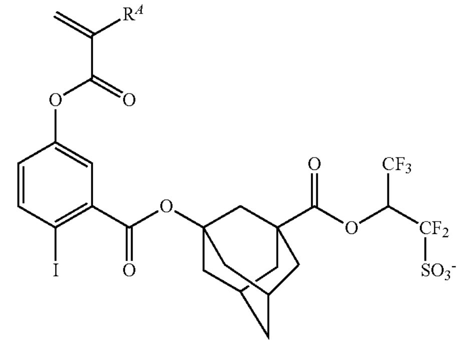
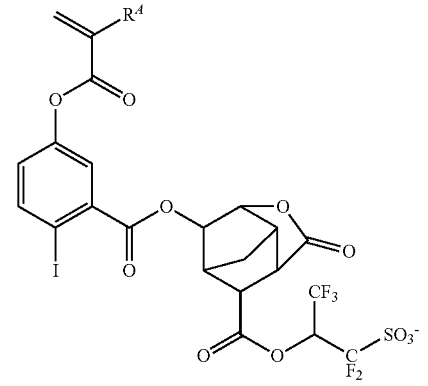
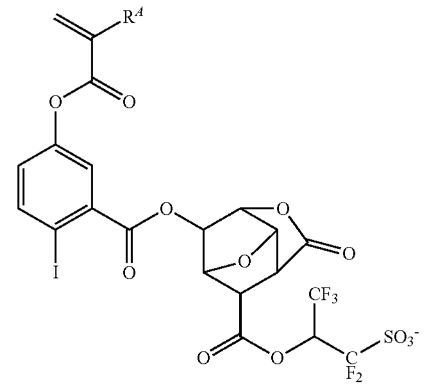
-continued
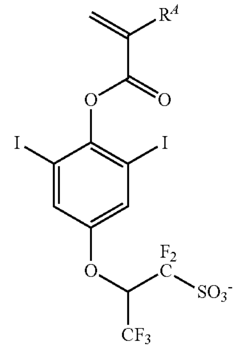
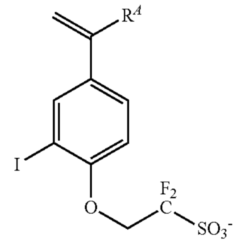
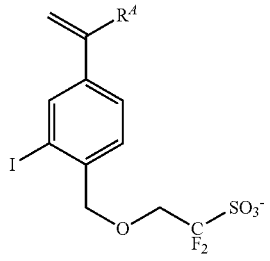
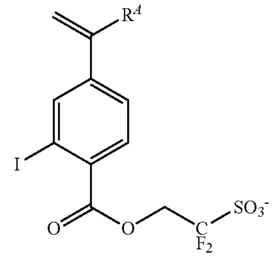
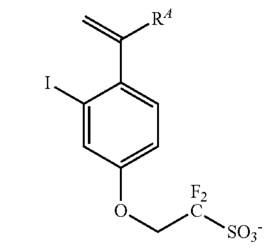
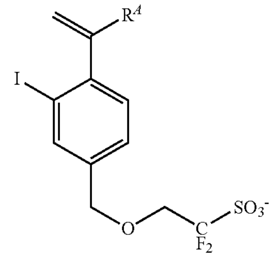
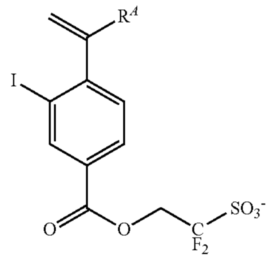
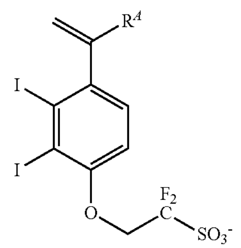
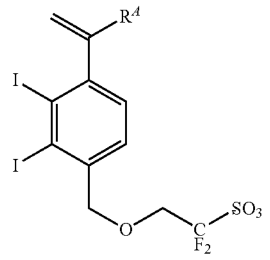
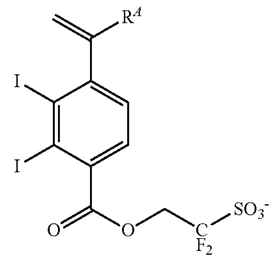

-continued
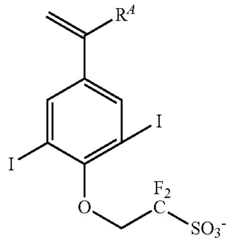
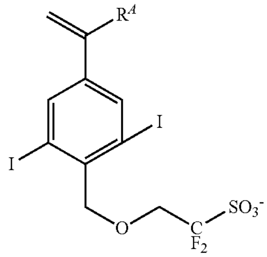
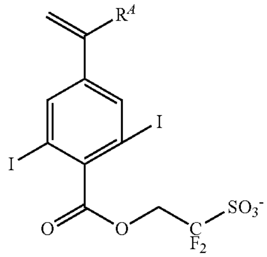
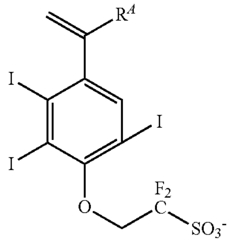
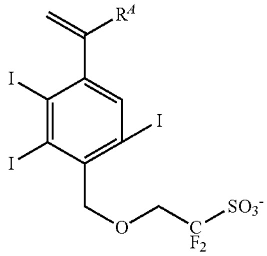
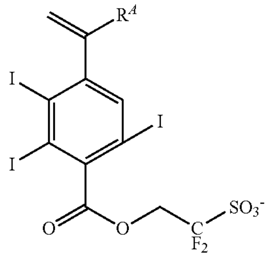
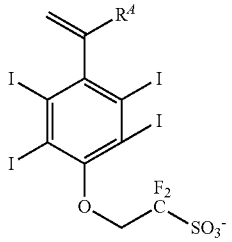
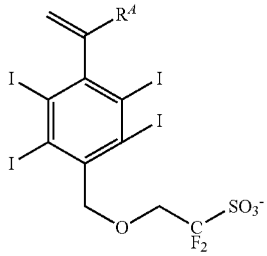
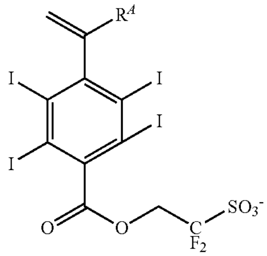
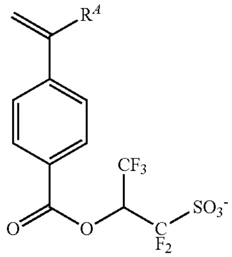
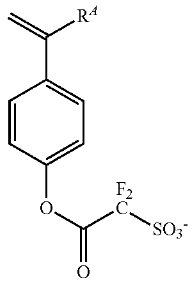
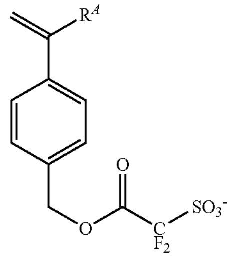
-continued
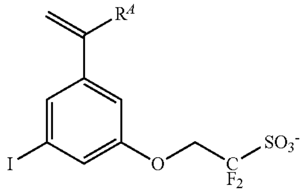
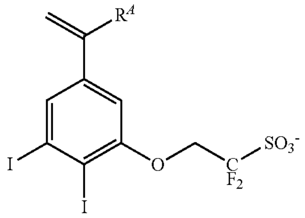
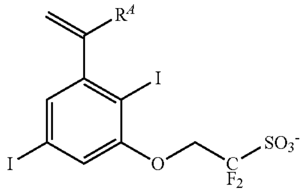
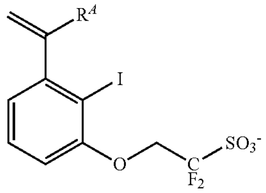
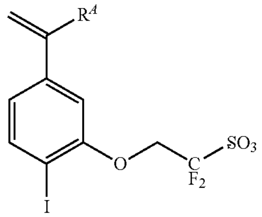
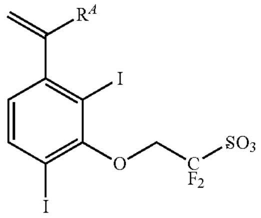
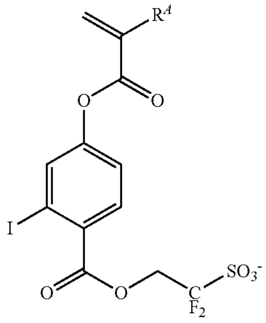
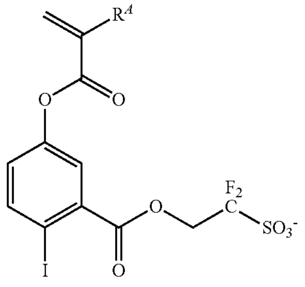

-continued
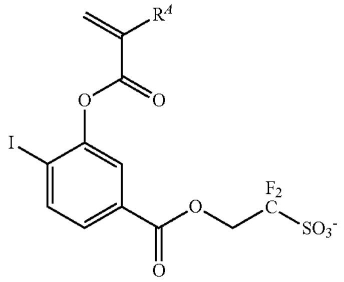
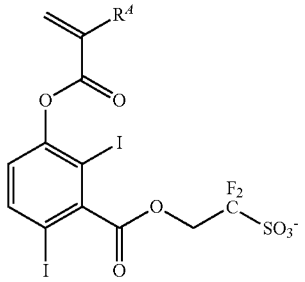
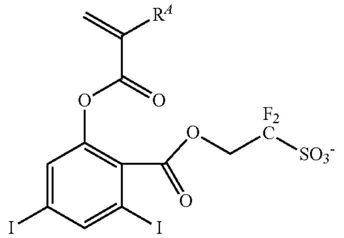
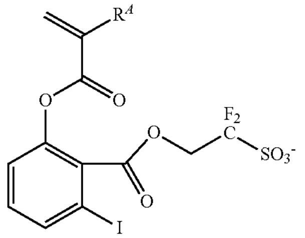
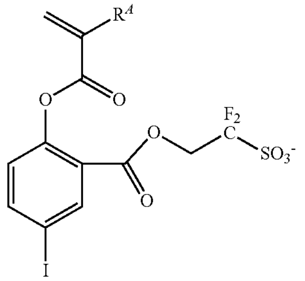
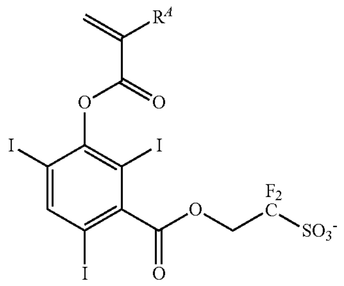
-continued
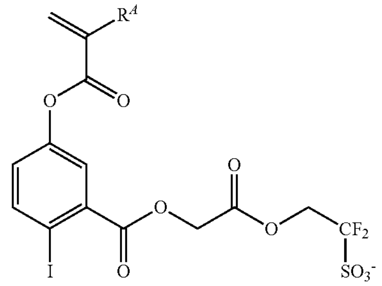
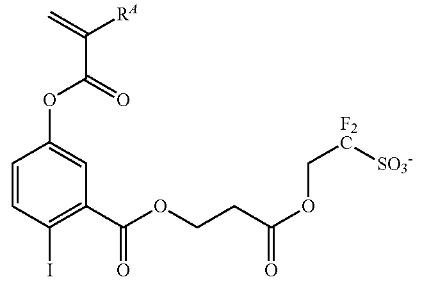
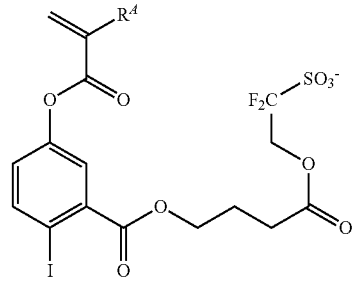
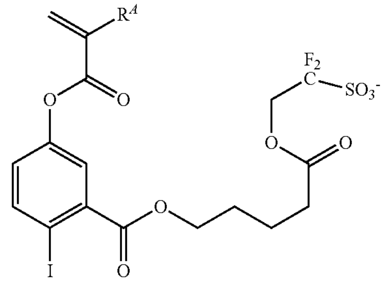
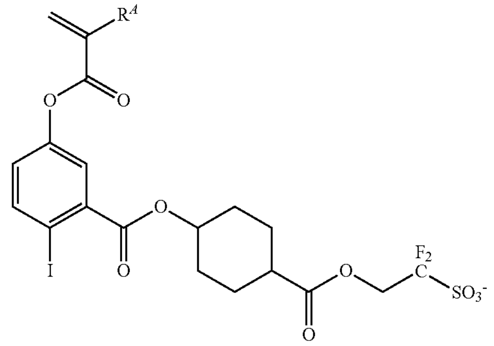

-continued
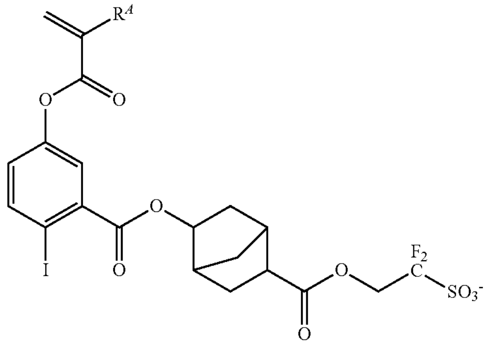
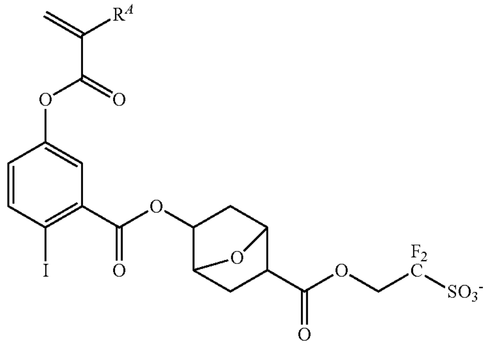
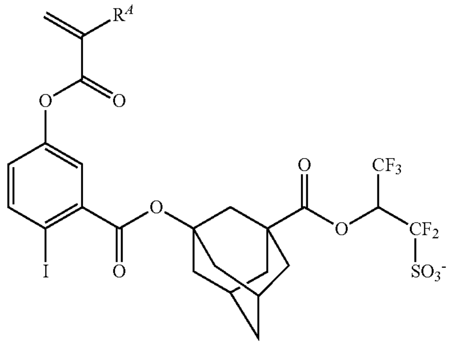
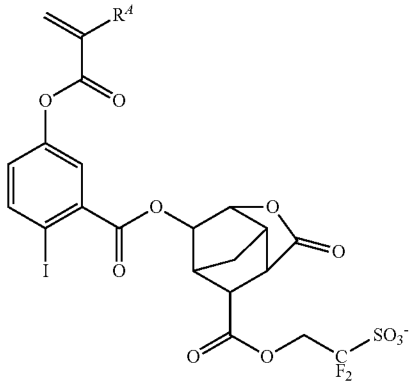
-continued
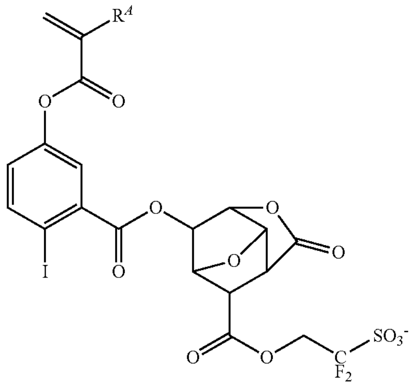
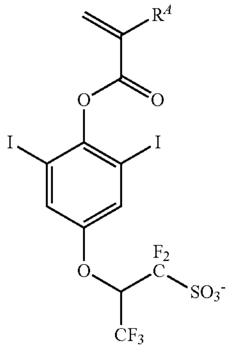
Examples of an anion of a monomer to give the repeating unit-f3 include those shown below, but are not limited thereto. Note that in the following formulae, $R^A$ is as defined above.
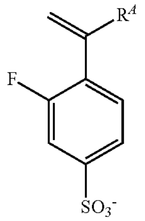
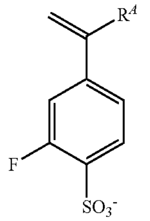
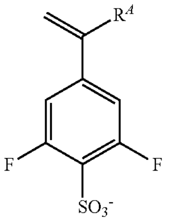
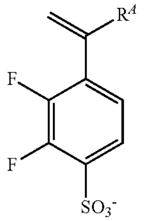
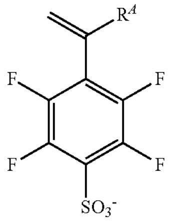
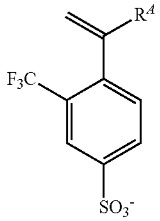
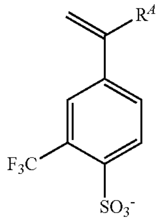
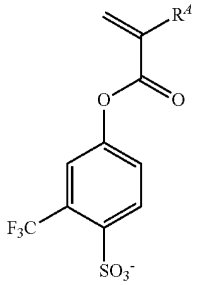

-continued
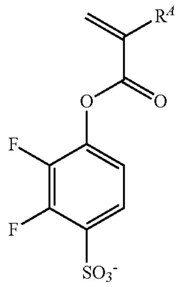
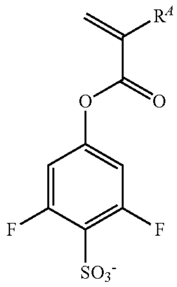
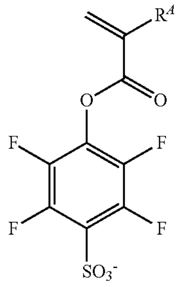
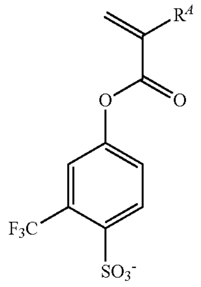
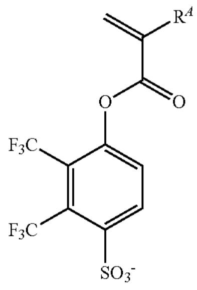
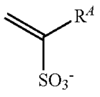
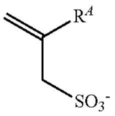
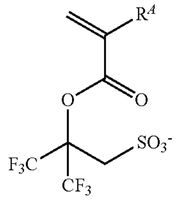
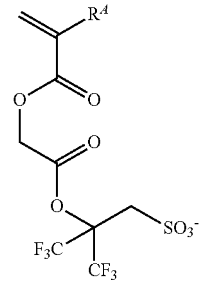
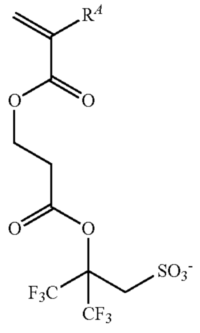
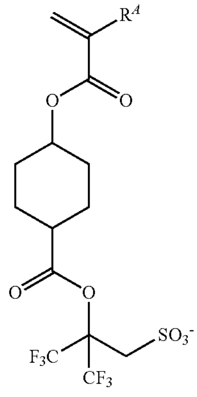
-continued
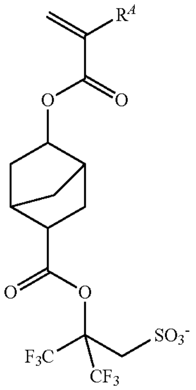
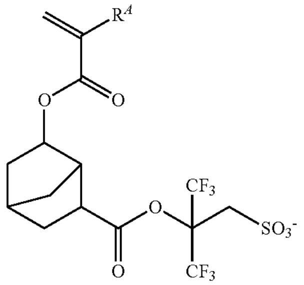
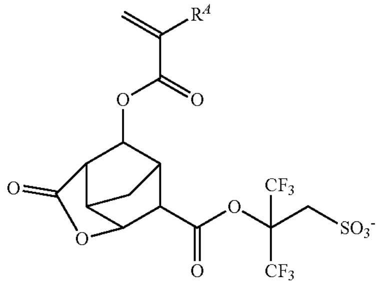
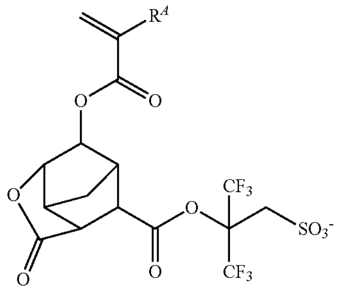
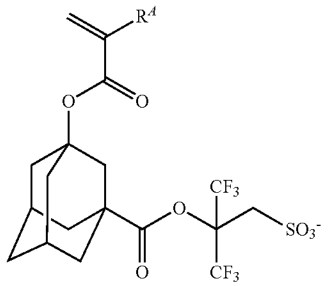
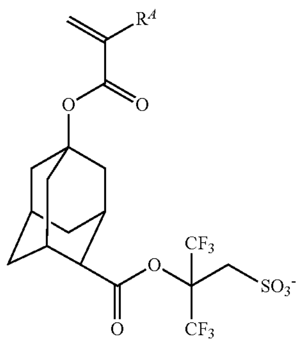
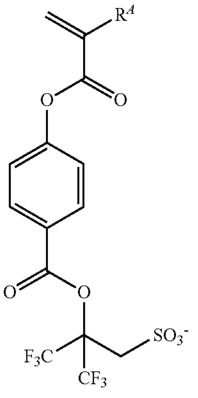

-continued

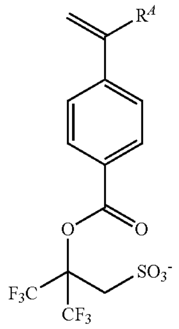

The repeating units-f1 to -f3 each function as an acid generator. By making an acid generator bond to a polymer main chain, acid diffusion can be reduced. Thus, degradation of resolution due to blurring by acid diffusion can be prevented. In addition, edge roughness and dimensional variation can be improved by the uniform dispersion of the acid generator. Note that when a base polymer containing the repeating units-f1 to -f3 is used, blending of the additive-type acid generator described below may be omitted.

As the cation in the sulfonium salt of the repeating units-f2 and -f3, it is possible to use those given above as the cation in the sulfonium salt shown in the general formula (1).

In the base polymer, the content ratios of the repeating units-a1, -a2, -b, -c, -d, -e, -f1, -f2, and -f3 are preferably $0 \leq a1 \leq 0.9$, $0 \leq a2 \leq 0.9$, $0 \leq a1+a2 \leq 0.9$, $0 \leq b \leq 0.9$, $0 \leq c \leq 0.9$, $0 \leq d \leq b$ 0.5, $0 \leq e \leq 0.5$, $0 \leq f1 \leq 0.5$, $0 \leq f2 \leq 0.5$, $0 \leq f3 \leq 0.5$, and $0 \leq f1+f2+f3 \leq 0.5$; more preferably $0 \leq a1 \leq 0.8$, $0 \leq a2 \leq 0.8$, $0 \leq a1+a2 \leq 0.8$, $0 \leq b \leq 0.8$, $0 \leq c \leq 0.8$, $0 \leq d \leq 0.4$, $0 \leq e \leq 0.4$, $0 \leq f1 \leq 0.4$, $0 \leq f2 \leq 0.4$, $0 \leq f3 \leq 0.4$, and $0 \leq f1+f2+f3 \leq 0.4$; further preferably $0 \leq a1 \leq 0.7$, $0 \leq a2 \leq 0.7$, $0 \leq a1+a2 \leq 0.7$, $0 \leq b \leq 0.7$, $0 \leq c \leq 0.7$, $0 \leq d \leq 0.3$, $0 \leq e \leq 0.3$, $0 \leq f1 \leq 0.3$, $0 \leq f2 \leq 0.3$, $0 \leq f3 \leq 0.3$, and $0 \leq f1+f2+f3 \leq 0.3$, provided that $a1+a2+b+c+d+e+f1+f2+f3=1.0$.

The base polymer may be synthesized, for example, by subjecting the monomers to give the repeating units described above to heat polymerization in an organic solvent to which a radical polymerization initiator has been added.

Examples of the organic solvent used in the polymerization include toluene, benzene, tetrahydrofuran, diethyl ether, dioxane, etc. Examples of the polymerization initiator include 2,2'-azobisisobutyronitrile (AIBN), 2,2'-azobis(2,4-dimethylvaleronitrile), dimethyl-2,2-azobis(2-methylpropionate), benzoyl peroxide, lauroyl peroxide, etc. The temperature during the polymerization is preferably 50 to 80° C. The reaction time is preferably 2 to 100 hours, more preferably 5 to 20 hours.

In the case where the monomer containing a hydroxy group is copolymerized, the process may include: substituting the hydroxy group with an acetal group susceptible to deprotection with acid, such as an ethoxyethoxy group, prior to the polymerization; and performing the deprotection with weak acid and water after the polymerization. Alternatively, the process may include: substituting the hydroxy group with an acetyl group, a formyl group, a pivaloyl group, or the like; and performing alkaline hydrolysis after the polymerization.

In a case where hydroxystyrene or hydroxyvinylnaphthalene is copolymerized, at first, acetoxystyrene or acetoxyvinylnaphthalene may be used in place of hydroxystyrene or hydroxyvinylnaphthalene; after the polymerization, the acetoxy group may be deprotected by the alkaline hydrolysis as described above to convert the acetoxystyrene or acetoxyvinylnaphthalene to hydroxystyrene or hydroxyvinylnaphthalene.

In the alkaline hydrolysis, a base such as ammonia water or triethylamine is usable. The reaction temperature is preferably −20 to 100° C., more preferably 0 to 60° C. The reaction time is preferably 0.2 to 100 hours, more preferably 0.5 to 20 hours.

The base polymer has a polystyrene-based weight-average molecular weight (Mw) of preferably 1,000 to 500,000, more preferably 2,000 to 30,000, further preferably 3,000 to 10,000, determined by gel permeation chromatography (GPC) using tetrahydrofuran (THF) as an eluent. When the Mw is 1,000 or more, the resist material has excellent heat resistance. When the Mw is 500,000 or less, alkali solubility is excellent, so that a footing phenomenon after pattern formation hardly occurs.

Further, when the base polymer has a narrow molecular weight distribution (Mw/Mn), there is no low-molecular-weight or high-molecular-weight polymer. Accordingly, foreign matters are not observed on the pattern after the exposure, and there is no risk of the pattern profile being degraded. The finer the pattern rule, the stronger the influences of Mw and Mw/Mn. Hence, in order to obtain a resist material suitably used for finer pattern dimension, the base polymer preferably has a narrow dispersity Mw/Mn of 1.0 to 2.0, particularly preferably 1.0 to 1.5.

The base polymer may contain two or more kinds of polymers that differ in composition ratio, Mw, and Mw/Mn.

[Acid Generator]

The inventive resist material may contain an acid generator that generates a strong acid (hereinafter, also referred to as additive-type acid generator). Here, the term strong acid means, in the case of a chemically amplified positive resist material, a compound that has sufficient acidity to cause a deprotection reaction of the acid-labile group of the base polymer; and in the case of a chemically amplified negative resist material, a compound that has sufficient acidity to cause a polarity change reaction or a crosslinking reaction by acid.

When such an acid generator is contained, the above-described sulfonium salt of a carboxylic acid bonded to a maleimide group functions as a quencher, so that the inventive resist material can function as a chemically amplified positive resist material or a chemically amplified negative resist material.

Examples of the acid generator include compounds that generate acids in response to actinic light or radiation (photo-acid generator). The photo-acid generator can be any photo-acid generator as long as the compound generates an acid upon high-energy beam irradiation. Preferably, the photo-acid generator generates a sulfonic acid, imide acid, or methide acid. Suitable photo-acid generators are sulfonium salt, iodonium salt, sulfonyldiazomethane, N-sulfonyloxyimide, oxime-O-sulfonate type acid generators, etc. Specific examples of the photo-acid generator include ones disclosed in paragraphs [0122] to [0142] of JP 2008-111103 A.

Moreover, a sulfonium salt shown by the following general formula (1-1) and an iodonium salt shown by the following general formula (1-2) can also be used suitably as photo-acid generators.

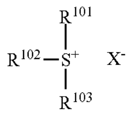

(1-1)

-continued (1-2)

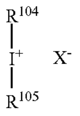

In the general formulae (1-1) and (1-2), $R^{101}$, $R^{102}$, $R^{103}$, $R^{104}$, and $R^{105}$ each independently represent a monovalent hydrocarbon group having 1 to 20 carbon atoms and optionally containing a heteroatom. Furthermore, any two of $R^{101}$, $R^{102}$, and $R^{103}$ may be bonded with each other to form a ring with a sulfur atom that is bonded thereto. The monovalent hydrocarbon group may be linear, branched, or cyclic, and specific examples thereof include the same examples as those given above in the description of $R^{21}$ to $R^{28}$ in the general formulae (f1) to (f3).

As the cation of the sulfonium salt represented by the general formula (1-1), it is possible to use a cation given above as a cation of the sulfonium salt shown in the general formula (1).

Examples of a cation of the iodonium salt represented by the general formula (1-2) include ones shown below, but are not limited thereto.

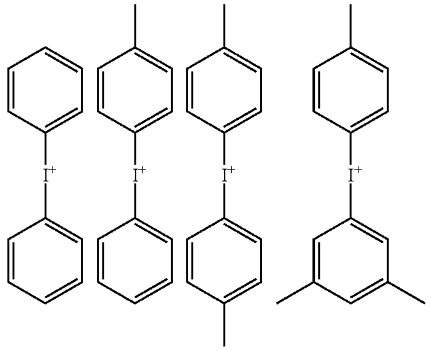

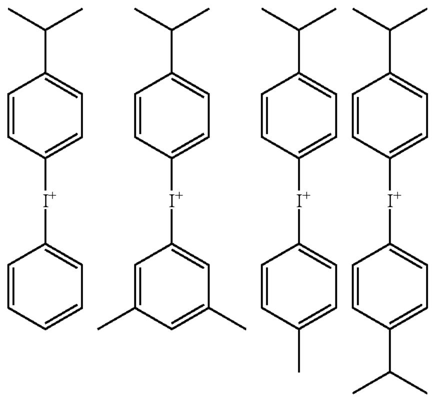

-continued

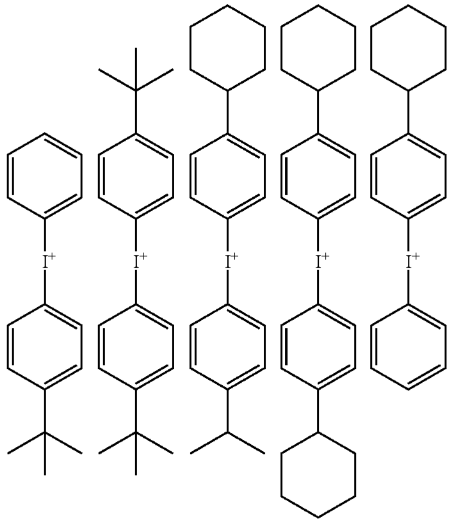

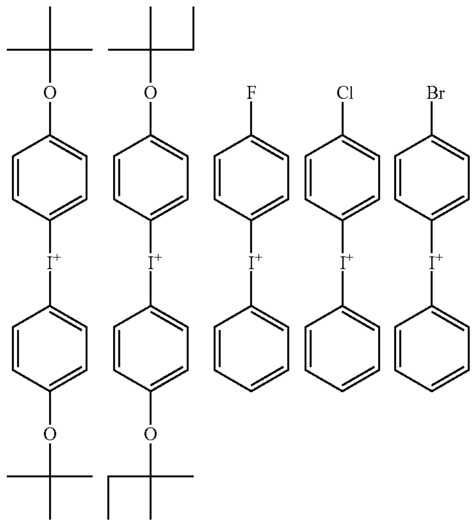

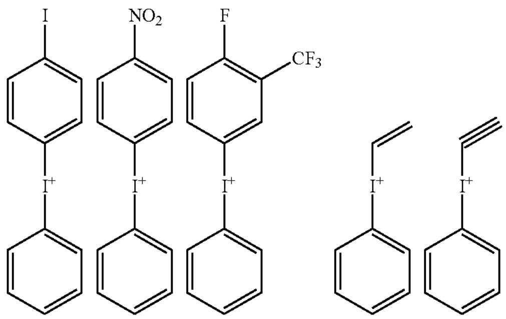

-continued

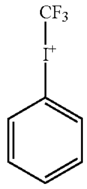

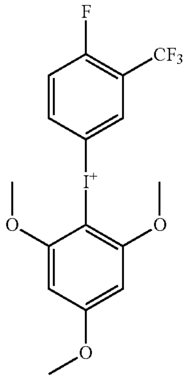

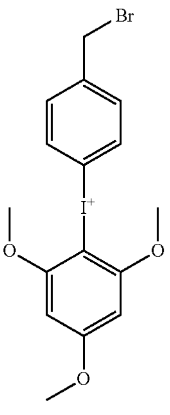

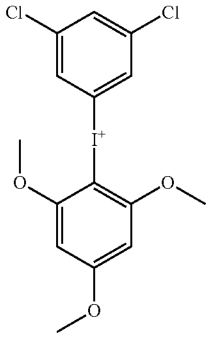

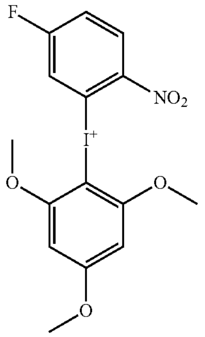

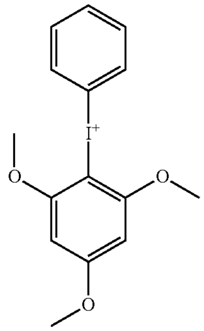

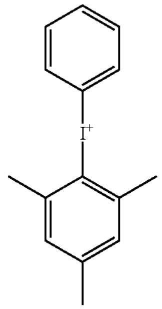

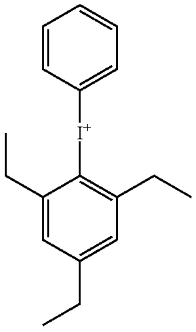

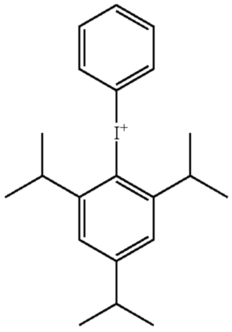

-continued

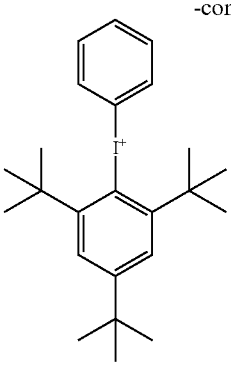

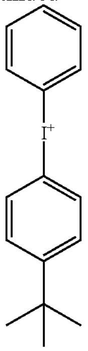

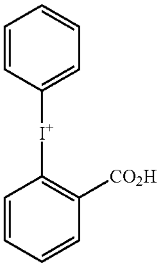

In the general formulae (1-1) and (1-2), $X^-$ represents an anion selected from the following general formulae (1A) to (1D).

$$R^{fa}—CF_2—SO_3^-$$ (1A)

(1B)

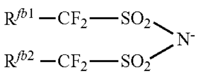

(1C)

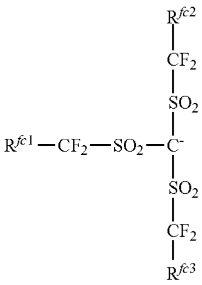

(1D)

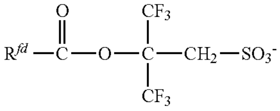

In the general formula (1A), $R^{fa}$ represents a fluorine atom or a monovalent hydrocarbon group having 1 to 40 carbon atoms and optionally containing a heteroatom. The monovalent hydrocarbon group may be linear, branched, or cyclic, and specific examples thereof include those to be described below in the description of $R^{107}$.

As the anion represented by the general formula (1A), an anion represented by the following general formula (1A') is preferable.

(1A')

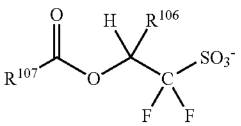

In the general formula (1A'), $R^{106}$ represents a hydrogen atom or a trifluoromethyl group, preferably a trifluoromethyl group. $R^{107}$ represents a monovalent hydrocarbon group having 1 to 38 carbon atoms and optionally containing a heteroatom. The heteroatom is preferably an oxygen atom, a nitrogen atom, a sulfur atom, a halogen atom, or the like, more preferably an oxygen atom. The monovalent hydrocarbon group particularly preferably has 6 to 30 carbon atoms from the viewpoint of achieving high resolution in fine pattern formation.

The monovalent hydrocarbon group may be linear, branched, or cyclic. Specific examples thereof include linear or branched alkyl groups such as a methyl group, an ethyl group, a propyl group, an isopropyl group, a butyl group, an isobutyl group, a sec-butyl group, a tert-butyl group, a pentyl group, a neopentyl group, a hexyl group, a heptyl group, a 2-ethylhexyl group, a nonyl group, an undecyl group, a tridecyl group, a pentadecyl group, a heptadecyl group, and an icosanyl group; monovalent saturated cyclic aliphatic hydrocarbon groups such as a cyclopentyl group, a cyclohexyl group, a 1-adamantyl group, a 2-adamantyl group, a 1-adamantylmethyl group, a norbornyl group, a norbornylmethyl group, a tricyclodecanyl group, a tetracyclododecanyl group, a tetracyclododecanylmethyl group, and a dicyclohexylmethyl group; monovalent unsaturated aliphatic hydrocarbon groups such as an allyl group and a 3-cyclohexenyl group; aryl groups such as a phenyl group, a 1-naphthyl group, and a 2-naphthyl group; aralkyl groups such as a benzyl group and a diphenylmethyl group; etc. In addition, examples of the monovalent hydrocarbon group containing a heteroatom include a tetrahydrofuryl group, a methoxymethyl group, an ethoxymethyl group, a methylthiomethyl group, an acetamidomethyl group, a trifluoroethyl group, a (2-methoxyethoxy)methyl group, an acetoxymethyl group, a 2-carboxy-1-cyclohexyl group, a 2-oxopropyl group, a 4-oxo-1-adamantyl group, a 3-oxocyclohexyl group, etc. Furthermore, some of the hydrogen atoms of these groups may be substituted with a group containing a heteroatom such as an oxygen atom, a sulfur atom, a nitrogen atom, or a halogen atom, or alternatively, some of the carbon atoms of these groups may be substituted with a group containing a heteroatom such as an oxygen atom, a sulfur atom, or a nitrogen atom. As a result, a hydroxy group, a cyano group, a carbonyl group, an ether bond, an ester bond, a sulfonic acid ester group, a carbonate group, a lactone ring, a sultone ring, carboxylic anhydride, a haloalkyl group, or the like may be contained.

The synthesis of the sulfonium salt containing the anion shown by the general formula (1A') is described in detail in JP 2007-145797 A, JP 2008-106045 A, JP 2009-7327 A, JP 2009-258695 A, etc. In addition, sulfonium salts disclosed in JP 2010-215608 A, JP 2012-41320 A, JP 2012-106986 A, JP 2012-153644 A, etc. are also suitably used.

Examples of the anion represented by the general formula (1A) include those shown below, but are not limited thereto. Note that in the following formulae, Ac represents an acetyl group.

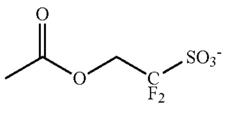
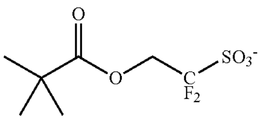
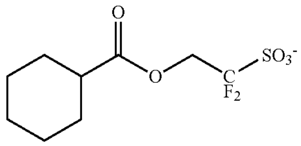

-continued

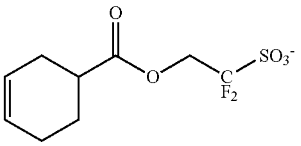
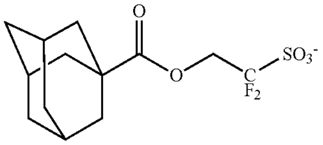
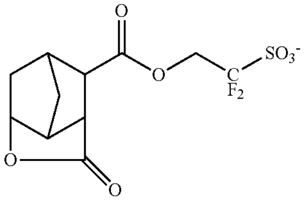
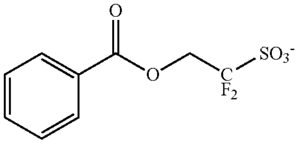
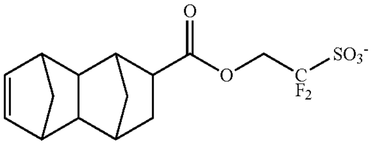
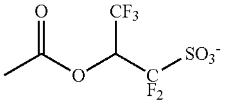
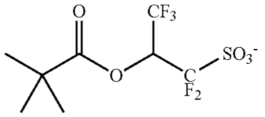
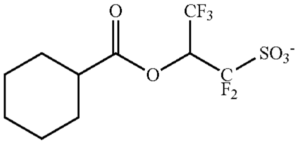
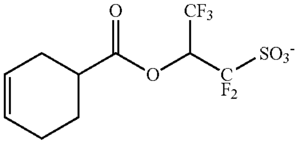
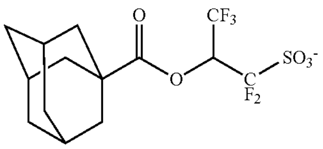
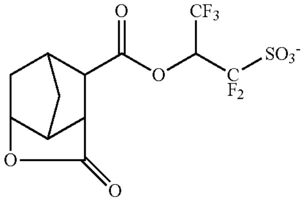
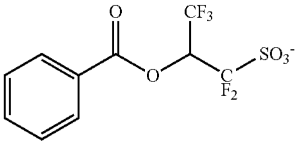

-continued
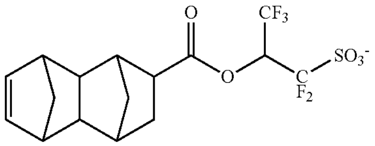
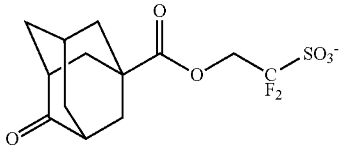
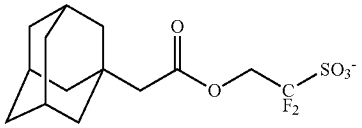
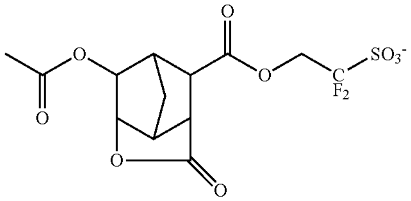
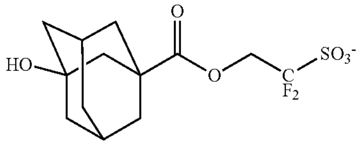
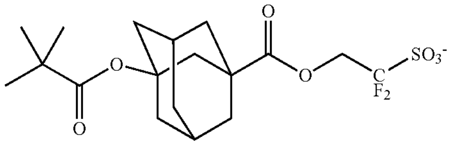
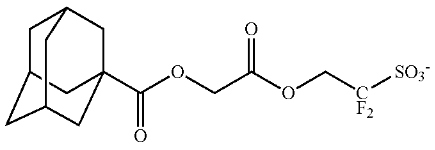
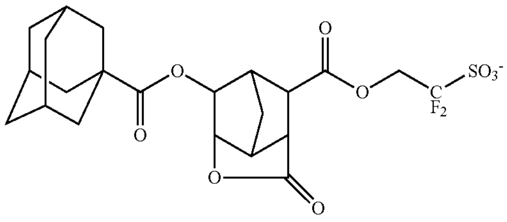
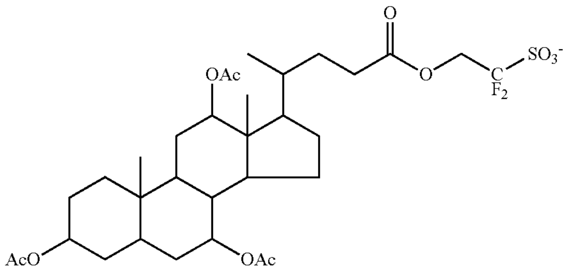
-continued
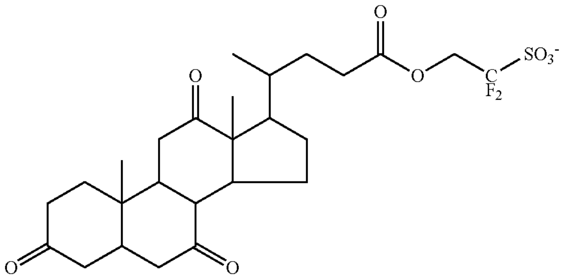
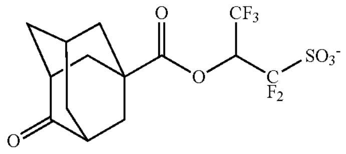
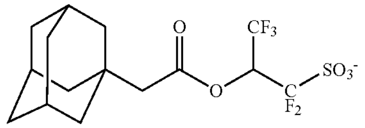
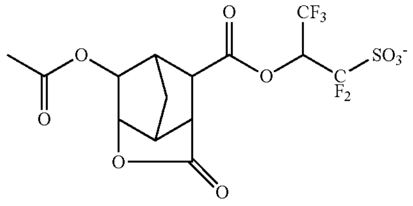
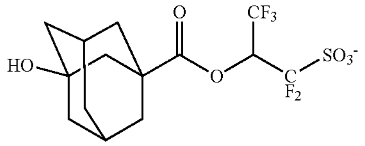
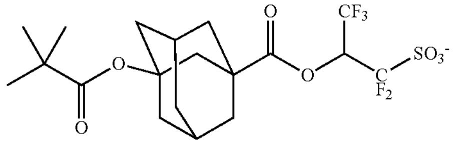
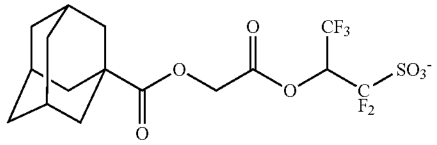
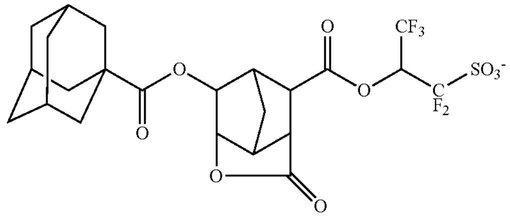
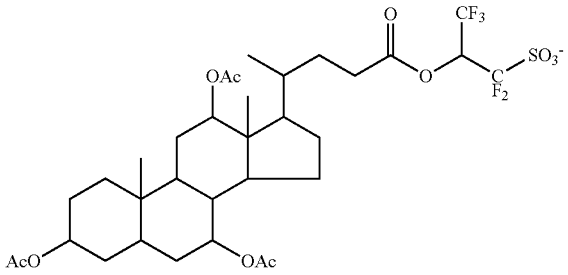

-continued

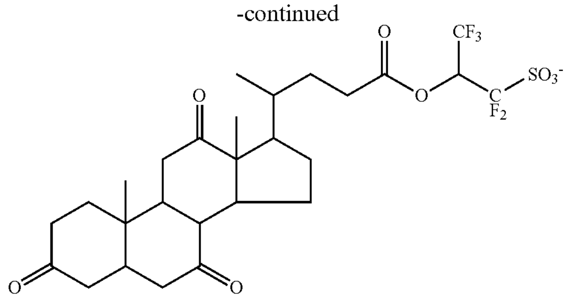

In the general formula (1B), $R^{fb1}$ and $R^{fb2}$ each independently represent a fluorine atom or a monovalent hydrocarbon group having 1 to 40 carbon atoms and optionally containing a heteroatom. The monovalent hydrocarbon group may be linear, branched, or cyclic. Specific examples thereof include those given in the description of $R^{107}$. $R^{fb1}$ and $R^{fb2}$ are preferably a fluorine atom or a linear fluorinated alkyl group having 1 to 4 carbon atoms. Alternatively, $Rf^{fb1}$ and $R^{fb2}$ may bond with each other to form a ring together with a group ($-CF_2-SO_2-N^--SO_2-CF_2-$) bonded therewith. In this event, the group obtained by bonding $R^{fb1}$ and $R^{fb2}$ with each other is preferably a fluorinated ethylene group or a fluorinated propylene group.

In the general formula (1C), $R^{fc1}$, $R^{fc2}$, and $R^{fc3}$ each independently represent a fluorine atom or a monovalent hydrocarbon group having 1 to 40 carbon atoms and optionally containing a heteroatom. The monovalent hydrocarbon group may be linear, branched, or cyclic. Specific examples thereof include those given in the description of $R^{107}$. $R^{fc1}$, $R^{fc2}$, and $R^{fc3}$ are preferably a fluorine atom or a linear fluorinated alkyl group having 1 to 4 carbon atoms. Alternatively, $R^{fc1}$ and $R^{fc2}$ may bond with each other to form a ring together with a group ($-CF_2-SO_2-C^--SO_2-CF_2-$) bonded therewith. In this event, the group obtained by bonding $R^{fc1}$ and $R^{fc2}$ with each other is preferably a fluorinated ethylene group or a fluorinated propylene group.

In the general formula (1D), $R^{fd}$ represents a monovalent hydrocarbon group having 1 to 40 carbon atoms and optionally containing a heteroatom. The monovalent hydrocarbon group may be linear, branched, or cyclic. Specific examples thereof include those given in the description of $R^{107}$.

The synthesis of the sulfonium salt containing the anion shown by the general formula (1D) is described in detail in JP 2010-215608 A and JP 2014-133723 A.

Examples of the anion shown by the general formula (1D) include those shown below, but are not limited thereto.

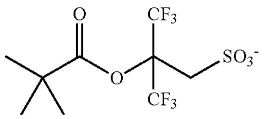

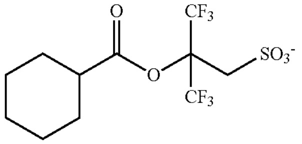

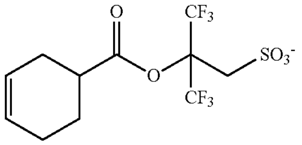

-continued

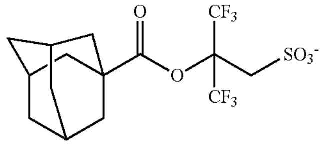

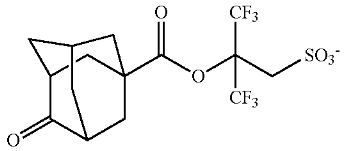

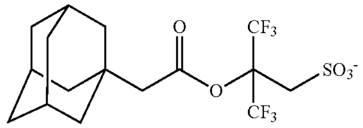

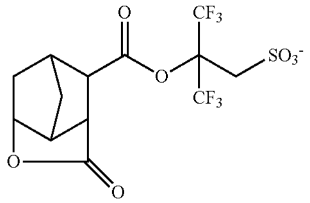

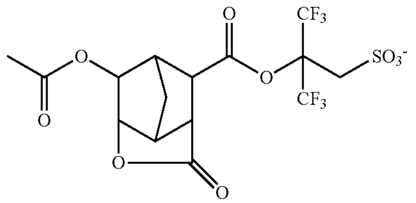

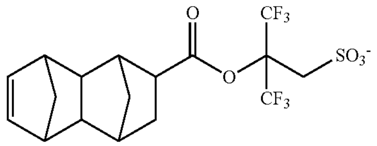

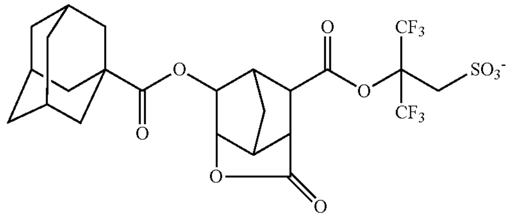

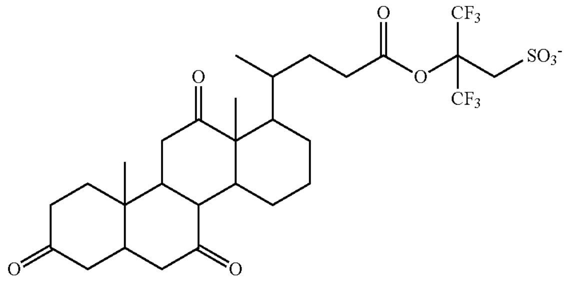

Note that the photo-acid generator containing the anion shown by the general formula (1D) does not have fluorine at α position of the sulfo group, but has two trifluoromethyl groups at β position, thereby providing sufficient acidity to cut the acid-labile group in the resist polymer. Thus, this photo-acid generator is utilizable.

One shown by the following general formula (2) can also be used suitably as a photo-acid generator.

(2)

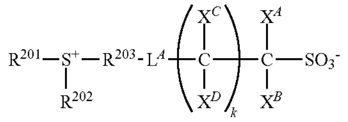

In the general formula (2), $R^{201}$ and $R^{202}$ each independently represent a monovalent hydrocarbon group having 1 to 30 carbon atoms and optionally containing a heteroatom. $R^{203}$ represents a divalent hydrocarbon group having 1 to 30 carbon atoms and optionally containing a heteroatom. In addition, any two of $R^{201}$, $R^{202}$, and $R^{203}$ may bond with each other to form a ring together with a sulfur atom bonded therewith. LA represents a single bond, an ether bond, or a divalent hydrocarbon group having 1 to 20 carbon atoms and optionally containing a heteroatom. $X^A$, $X^B$, $X^C$, and $X^D$ each independently represent a hydrogen atom, a fluorine atom, or a trifluoromethyl group. Nevertheless, at least one of $X^A$, $X^B$, $X^C$, and $X^D$ is a fluorine atom or a trifluoromethyl group. "k" represents an integer of 0 to 3.

The monovalent hydrocarbon group may be linear, branched, or cyclic. Specific examples thereof include: linear or branched alkyl groups such as a methyl group, an ethyl group, a propyl group, an isopropyl group, an n-butyl group, a sec-butyl group, a tert-butyl group, an n-pentyl group, a tert-pentyl group, an n-hexyl group, an n-octyl group, an n-nonyl group, an n-decyl group, and a 2-ethylhexyl group; monovalent saturated cyclic hydrocarbon groups such as a cyclopentyl group, a cyclohexyl group, a cyclopentylmethyl group, a cyclopentylethyl group, a cyclopentylbutyl group, a cyclohexylmethyl group, a cyclohexylethyl group, a cyclohexylbutyl group, a norbornyl group, an oxanorbornyl group, a tricyclo[5.2.1.0$^{2,6}$]decanyl group, and an adamantyl group; aryl groups such as a phenyl group, a naphthyl group, and an anthracenyl group; etc. Additionally, these groups may have some of the hydrogen atoms thereof substituted with a group containing a heteroatom such as an oxygen atom, a sulfur atom, a nitrogen atom, or a halogen atom, while these groups may have some of the carbon atoms thereof substituted with a group containing a heteroatom such as an oxygen atom, a sulfur atom, or a nitrogen atom. Thus, the resulting monovalent hydrocarbon group may contain a hydroxy group, a cyano group, a carbonyl group, an ether bond, an ester bond, a sulfonic acid ester group, a carbonate group, a lactone ring, a sultone ring, carboxylic anhydride, a haloalkyl group, etc.

The divalent hydrocarbon group may be linear, branched, or cyclic. Specific examples thereof include linear or branched alkanediyl groups such as a methylene group, an ethylene group, a propane-1,3-diyl group, a butane-1,4-diyl group, a pentane-1,5-diyl group, a hexane-1,6-diyl group, a heptane-1,7-diyl group, an octane-1,8-diyl group, a nonane-1,9-diyl group, a decane-1,10-diyl group, an undecane-1,11-diyl group, a dodecane-1,12-diyl group, a tridecane-1,13-diyl group, a tetradecane-1,14-diyl group, a pentadecane-1,15-diyl group, a hexadecane-1,16-diyl group, and a heptadecane-1,17-diyl group; divalent saturated cyclic hydrocarbon groups such as a cyclopentanediyl group, a cyclohexanediyl group, a norbornanediyl group, and an adamantanediyl group; divalent unsaturated cyclic hydrocarbon groups such as a phenylene group and a naphthylene group; etc. Additionally, some of the hydrogen atoms of these groups may be substituted with an alkyl group such as a methyl group, an ethyl group, a propyl group, an n-butyl group, or a tert-butyl group, and some of the hydrogen atoms of these groups may be substituted with a group containing a heteroatom such as an oxygen atom, a sulfur atom, a nitrogen atom, or a halogen atom, or some of the carbon atoms of these groups may be substituted with a group containing a heteroatom such as an oxygen atom, a sulfur atom, or a nitrogen atom. Thus, the resulting divalent hydrocarbon group may contain a hydroxy group, a cyano group, a carbonyl group, an ether bond, an ester bond, a sulfonic acid ester group, a carbonate group, a lactone ring, a sultone ring, carboxylic anhydride, a haloalkyl group, etc. The heteroatom is preferably an oxygen atom.

The photo-acid generator shown by the general formula (2) is preferably shown by the following general formula (2').

(2')

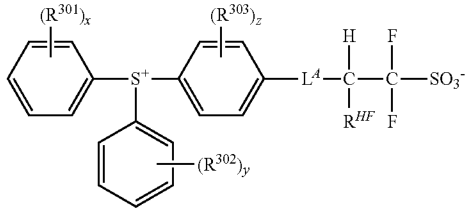

In the general formula (2'), LA is as defined above. $R^{HF}$ represents a hydrogen atom or a trifluoromethyl group, preferably a trifluoromethyl group. $R^{301}$, $R^{302}$, and $R^{303}$ each independently represent a hydrogen atom or a monovalent hydrocarbon group having 1 to 20 carbon atoms and optionally containing a heteroatom. The monovalent hydrocarbon group may be linear, branched, or cyclic, and specific examples thereof include those given in the description of $R^{107}$. "x" and "y" each independently represent an integer of 0 to 5, and "z" represents an integer of 0 to 4.

Examples of the photo-acid generator represented by the general formula (2) include those shown below, but are not limited thereto. Note that in the following formulae, $R^{HF}$ is as defined above, and Me represents a methyl group.

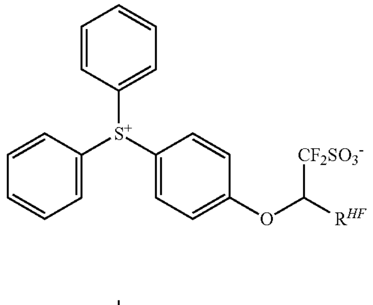

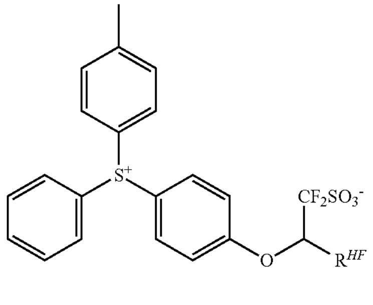

-continued
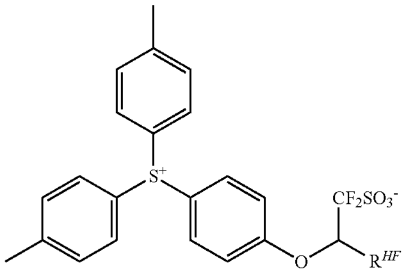
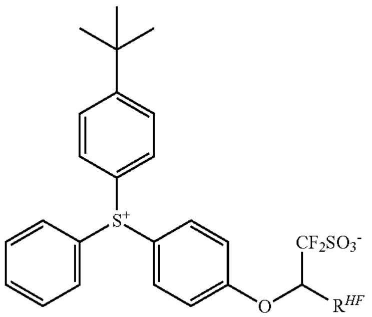
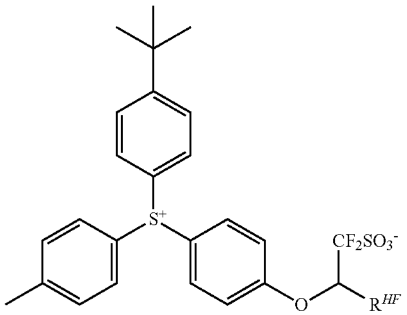
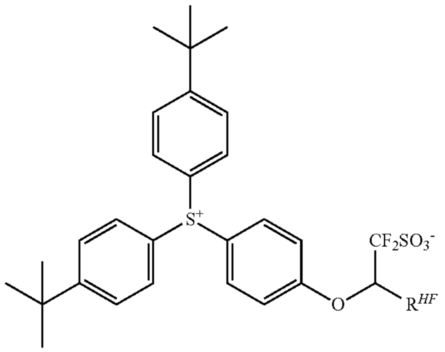
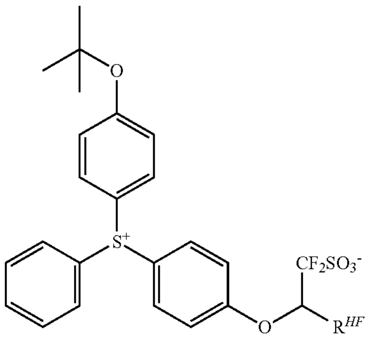
-continued
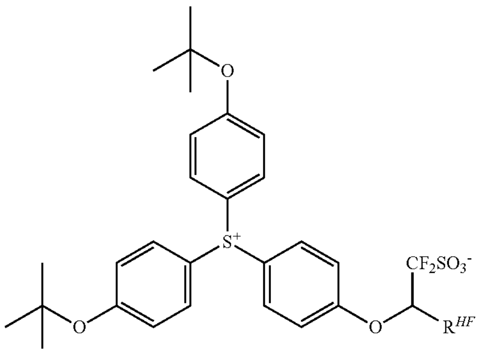
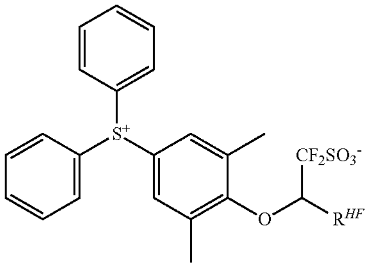
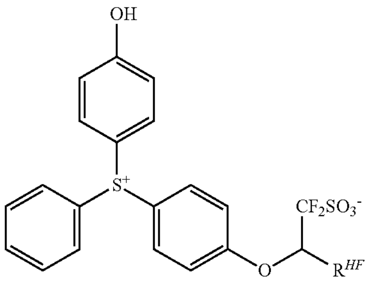
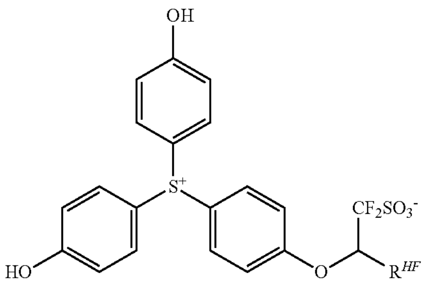
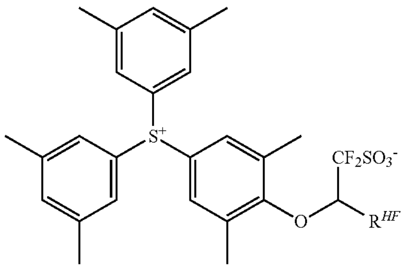
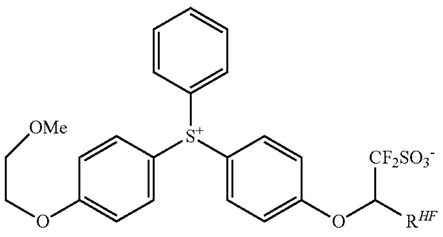

-continued
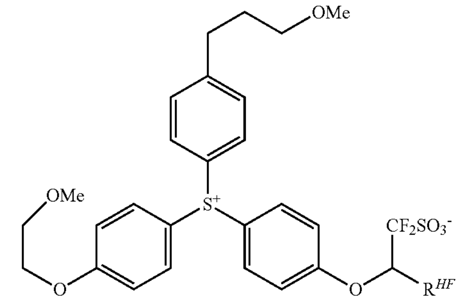
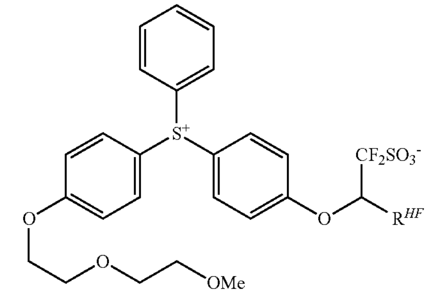
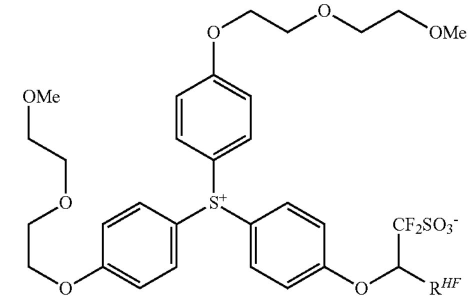
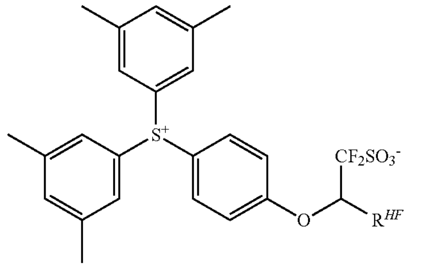
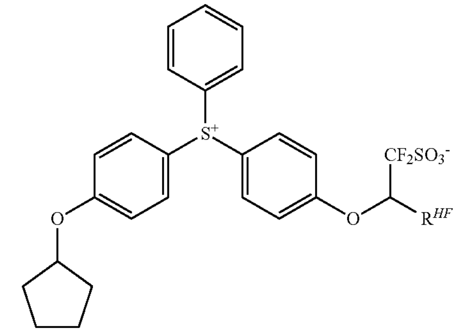
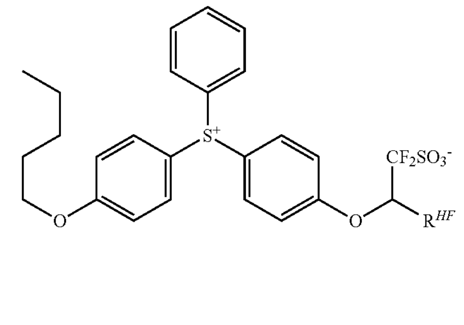
-continued
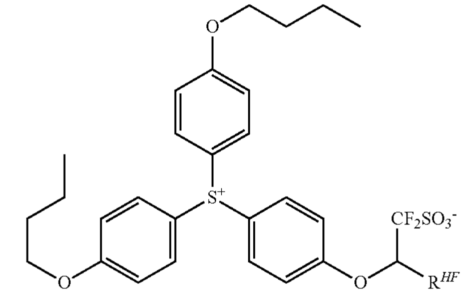
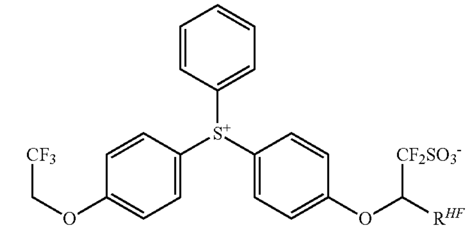
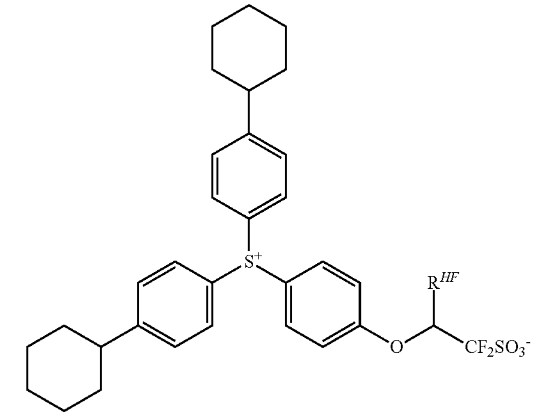
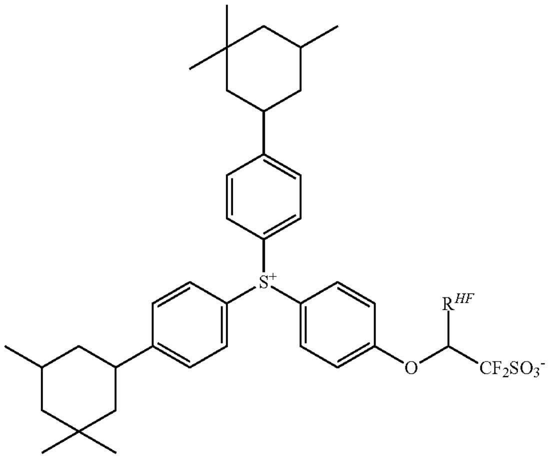
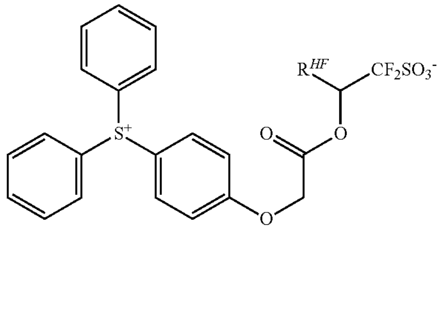

-continued

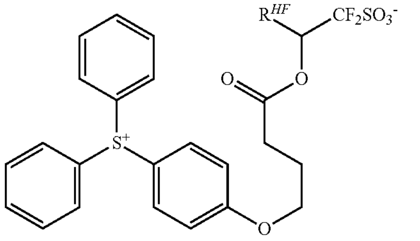

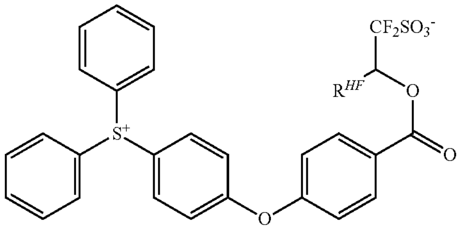

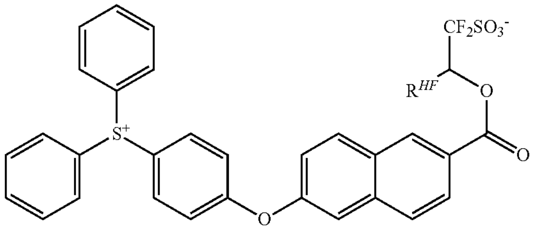

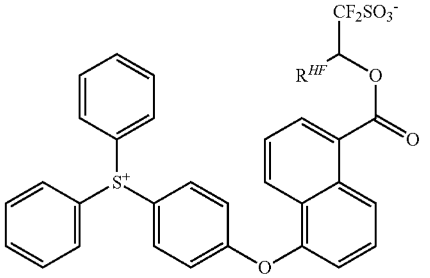

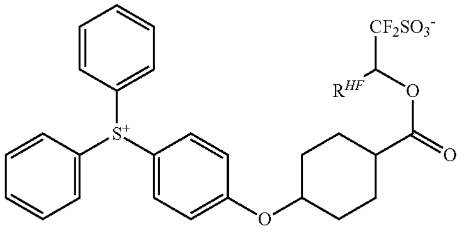

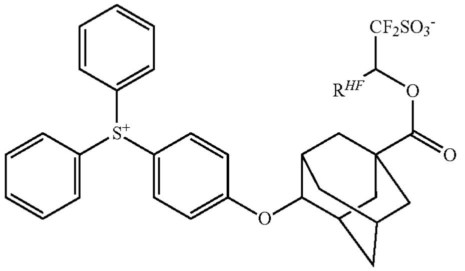

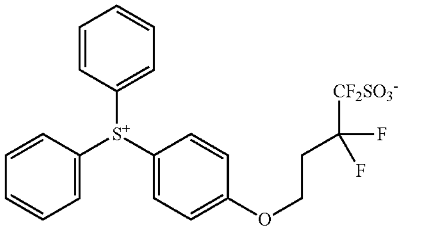

-continued

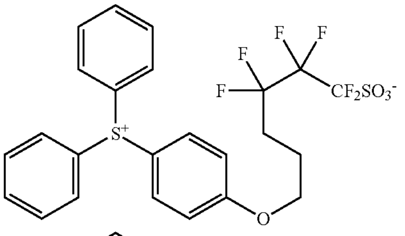

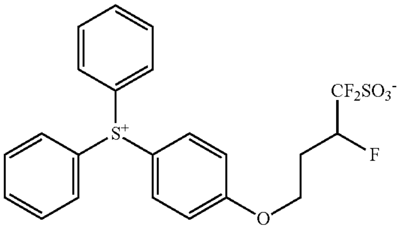

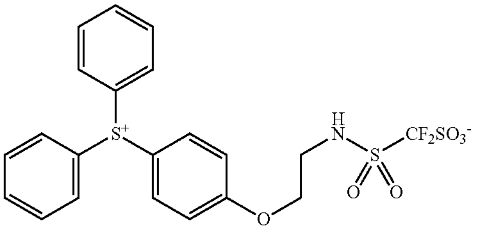

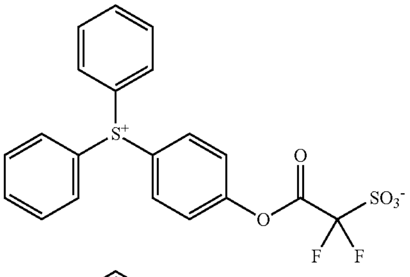

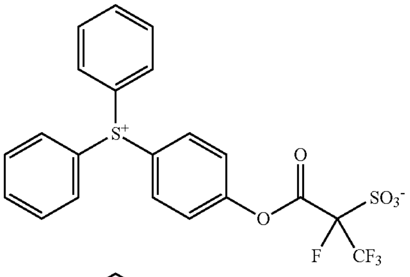

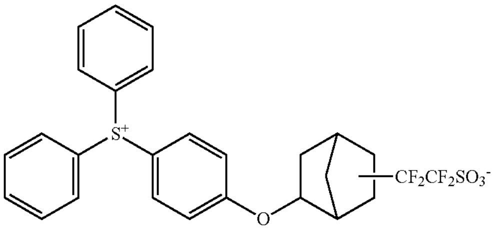

The photo-acid generators containing the anion shown by the formula (1A') or (1D) are particularly preferable because of small acid diffusion and excellent solubility to a resist solvent. One containing the anion shown by the formula (2') is also particularly preferable because the acid diffusion is quite small.

When the inventive resist material contains an additive-type acid generator, the additive-type acid generator is preferably contained in an amount of 0.1 to 50 parts by mass, more preferably 1 to 40 parts by mass based on 100 parts by mass of the base polymer. Incorporating the repeating unit-f into the base polymer and/or incorporating the additive-type acid generator enables the inventive resist material to function as a chemically amplified resist material.

[Organic Solvent]

The inventive resist material may be blended with an organic solvent. The organic solvent is not particularly limited as long as it is capable of dissolving the above-described quencher, which is a sulfonium salt of a carboxylic acid bonded to a maleimide group, as well as other components if contained. Examples of such an organic solvent include ones disclosed in paragraphs [0144] and [0145] of JP 2008-111103 A: ketones such as cyclohexanone, cyclopentanone, and methyl-2-n-pentyl ketone; alcohols such as 3-methoxybutanol, 3-methyl-3-methoxybutanol, 1-methoxy-2-propanol, 1-ethoxy-2-propanol, and diacetone alcohol; ethers such as propylene glycol monomethyl ether, ethylene glycol monomethyl ether, propylene glycol monoethyl ether, ethylene glycol monoethyl ether, propylene glycol dimethyl ether, and diethylene glycol dimethyl ether; esters such as propylene glycol monomethyl ether acetate, propylene glycol monoethyl ether acetate, ethyl lactate, ethyl pyruvate, butyl acetate, methyl 3-methoxypropionate, ethyl 3-ethoxypropionate, tert-butyl acetate, tert-butyl propionate, and propylene glycol mono-tert-butyl ether acetate; lactones such as γ-butyrolactone; mixed solvents thereof; etc.

The inventive resist material preferably contains the organic solvent in an amount of 100 to 10,000 parts by mass, more preferably 200 to 8,000 parts by mass based on 100 parts by mass of the base polymer.

[Other Components]

In addition to the above-described components, a surfactant, a dissolution inhibitor, a crosslinking agent, and so forth can be blended in appropriate combination depending on the purpose to formulate a positive resist material and a negative resist material. Thereby, in an exposed area of the base polymer, the dissolution rate to a developer is accelerated by the catalytic reaction, so that the positive resist material and negative resist material have extremely high sensitivity. In this case, the resist film has high dissolution contrast and resolution, exposure latitude, excellent process adaptability, and favorable pattern profile after exposure. Particularly, the positive resist material and negative resist material are capable of suppressing acid diffusion, resulting in a small difference in profile between isolated and nested. Because of these advantages, the inventive resist material is highly practical and is a very effective resist material for VLSI.

Examples of the surfactant include ones disclosed in paragraphs [0165] and [0166] of JP 2008-111103 A. Adding a surfactant can further enhance or control the coatability of the resist material. One kind of the surfactant can be used, or two or more kinds thereof can be used in combination. The surfactant content in the inventive resist material is preferably 0.0001 to 10 parts by mass based on 100 parts by mass of the base polymer.

In the case of a positive resist material, blending a dissolution inhibitor can further increase the difference in dissolution rate between exposed and unexposed areas, and further enhance the resolution. Examples of the dissolution inhibitor include compounds: the compounds each have a molecular weight of preferably 100 to 1,000, more preferably 150 to 800; and which contains two or more phenolic hydroxy groups per molecule, and in which 0 to 100 mol % of all the hydrogen atoms of the phenolic hydroxy groups are substituted with acid-labile groups; or a compound which contains a carboxy group in a molecule, and in which 50 to 100 mol % of all the hydrogen atoms of such carboxy groups are substituted with acid-labile groups on average. Specific examples include compounds obtained by substituting acid-labile groups for hydrogen atoms of hydroxy groups or carboxy groups of bisphenol A, trisphenol, phenolphthalein, cresol novolak, naphthalenecarboxylic acid, adamantanecarboxylic acid, cholic acid; etc. Examples of such compounds are disclosed in paragraphs [0155] to [0178] of JP 2008-122932 A.

When the inventive resist material is a positive resist material, the dissolution inhibitor is contained in an amount of preferably 0 to 50 parts by mass, more preferably 5 to 40 parts by mass based on 100 parts by mass of the base polymer. One kind of the dissolution inhibitor can be used, or two or more kinds thereof can be used in combination.

Meanwhile, in the case of a negative resist material, the dissolution rate of exposed areas can be decreased by adding a crosslinking agent, and thus, a negative pattern can be obtained. Examples of the crosslinking agent include epoxy compounds, melamine compounds, guanamine compounds, glycoluril compounds, or urea compounds substituted with at least one group selected from a methylol group, an alkoxymethyl group, and an acyloxymethyl group, isocyanate compounds, azide compounds, compounds having a double bond such as an alkenyl ether group, etc. These compounds may be used as an additive, or introduced into a polymer side chain as a pendant group. In addition, compounds containing a hydroxy group can also be used as a crosslinking agent. One kind of crosslinking agent may be used, or two or more kinds thereof may be used in combination.

Examples of the epoxy compounds include tris(2,3-epoxypropyl)isocyanurate, trimethylolmethane triglycidyl ether, trimethylolpropane triglycidyl ether, triethylolethane triglycidyl ether, and the like.

Examples of the melamine compounds include hexamethylolmelamine, hexamethoxymethylmelamine, such compounds as hexamethylolmelamine having 1 to 6 methylol groups methoxymethylated, and mixtures thereof; and hexamethoxyethylmelamine, hexaacyloxymethylmelamine, such compounds as hexamethylolmelamine having 1 to 6 methylol groups acyloxymethylated, and mixtures thereof.

Examples of the guanamine compounds include tetramethylolguanamine, tetramethoxymethylguanamine, such compounds as tetramethylolguanamine having 1 to 4 methylol groups methoxymethylated, and mixtures thereof; and tetramethoxyethylguanamine, tetraacyloxyguanamine, such compounds as tetramethylolguanamine having 1 to 4 methylol groups acyloxymethylated, and mixtures thereof.

Examples of the glycoluril compounds include tetramethylolglycoluril, tetramethoxyglycoluril, tetramethoxymethylglycoluril, such compounds as tetramethylolglycoluril having 1 to 4 methylol groups methoxymethylated, and mixtures thereof; and such compounds as tetramethylolglycoluril having 1 to 4 methylol groups acyloxymethylated, and mixtures thereof.

Examples of the urea compounds include tetramethylol urea, tetramethoxymethyl urea, tetramethoxyethyl urea, such compounds as tetramethylol urea having 1 to 4 methylol groups methoxymethylated, mixtures thereof, and the like.

Examples of the isocyanate compounds include tolylene diisocyanate, diphenylmethane diisocyanate, hexamethylene diisocyanate, cyclohexane diisocyanate, and the like.

Examples of the azide compounds include 1,1'-biphenyl-4,4'-bisazide, 4,4'-methylidene bisazide, 4,4'-oxybisazide, and the like.

Examples of the compounds containing an alkenyl ether group include ethylene glycol divinyl ether, triethylene glycol divinyl ether, 1,2-propanediol divinyl ether, 1,4-butanediol divinyl ether, tetramethylene glycol divinyl ether, neopentyl glycol divinyl ether, trimethylolpropane trivinyl ether, hexanediol divinyl ether, 1,4-cyclohexanediol divinyl ether, pentaerythritol trivinyl ether, pentaerythritol tetravinyl ether, sorbitol tetravinyl ether, sorbitol pentavinyl ether, and the like.

When the inventive resist material is a negative resist material, the crosslinking agent is preferably contained in an amount of 0.1 to 50 parts by mass, more preferably 1 to 40 parts by mass based on 100 parts by mass of the base polymer.

The inventive resist material may be blended with a quencher other than the above-described sulfonium salt of a carboxylic acid bonded to a maleimide group (hereinafter, referred to as other quenchers). Examples of such quenchers include conventional basic compounds. Examples of the conventional basic compounds include primary, secondary, and tertiary aliphatic amines, mixed amines, aromatic amines, heterocyclic amines, nitrogen-containing compounds having a carboxy group, nitrogen-containing compounds having a sulfonyl group, nitrogen-containing compounds having a hydroxy group, nitrogen-containing compounds having a hydroxyphenyl group, alcoholic nitrogen-containing compounds, amides, imides, carbamates, etc. Particularly preferable are primary, secondary, and tertiary amine compounds disclosed in paragraphs [0146] to [0164] of JP 2008-111103 A; especially, amine compounds having a hydroxy group, an ether bond, an ester bond, a lactone ring, a cyano group, or a sulfonic acid ester group; compounds having a carbamate group disclosed in JP 3790649 B; etc. Adding such a basic compound can, for example, further suppress the acid diffusion rate in the resist film and correct the shape.

Other examples of the other quenchers include onium salts such as sulfonium salts, iodonium salts, and ammonium salts of carboxylic acids and sulfonic acids which are not fluorinated at α position as disclosed in JP 2008-158339 A. While α-fluorinated sulfonic acid, imide acid, or methide acid is necessary to deprotect the acid-labile group of carboxylic acid ester, a carboxylic acid or sulfonic acid not fluorinated at a position is released by salt exchange with the onium salt not fluorinated at α position. Such carboxylic acid and sulfonic acid not fluorinated at α position hardly induce deprotection reaction, and thus function as quenchers.

Other examples of the other quenchers further include a polymeric quencher disclosed in JP 2008-239918 A. This quencher is oriented on the resist surface after coating, and enhances the rectangularity of the resist after patterning. The polymeric quencher also has effects of preventing rounding of pattern top and film thickness loss of pattern when a top coat for immersion exposure is applied.

In the inventive resist material, the other quenchers are preferably contained in an amount of 0 to 5 parts by mass, more preferably 0 to 4 parts by mass based on 100 parts by mass of the base polymer. One kind of such quenchers may be used or two or more kinds thereof may be used in combination.

The inventive resist material may be blended with a water-repellency enhancer for enhancing the water repellency on the resist surface after spin coating. The water-repellency enhancer can be employed in immersion lithography with no top coat.

The water-repellency enhancer is preferably a polymer compound containing a fluorinated alkyl group, a polymer compound containing a 1,1,1,3,3,3-hexafluoro-2-propanol residue with a particular structure, etc., more preferably ones exemplified in JP 2007-297590 A, JP 2008-111103 A, etc. The water-repellency enhancer needs to be dissolved in an alkali developer or an organic solvent developer. The water-repellency enhancer having a particular 1,1,1,3,3,3-hexafluoro-2-propanol residue mentioned above has favorable solubility to developers. A polymer compound containing a repeating unit with an amino group or amine salt as a water-repellency enhancer exhibits high effects of preventing acid evaporation during post-exposure baking (PEB) and opening failure of a hole pattern after development. One kind of the water-repellency enhancer may be used, or two or more kinds thereof may be used in combination.

In the inventive resist material, the water-repellency enhancer is preferably contained in an amount of 0 to 20 parts by mass, more preferably 0.5 to 10 parts by mass based on 100 parts by mass of the base polymer.

The inventive resist material can also be blended with an acetylene alcohol. Examples of the acetylene alcohol include ones disclosed in paragraphs [0179] to [0182] of JP 2008-122932 A. The inventive resist material contains the acetylene alcohol in an amount of preferably 0 to 5 parts by mass based on 100 parts by mass of the base polymer.

[Positive Resist Material and Negative Resist Material]

The inventive resist material is a chemically amplified positive resist material when an acid-labile group is contained, and is a chemically amplified negative resist material when an acid-labile group is not contained.

[Patterning Process]

When the inventive resist material is used for manufacturing various integrated circuits, known lithography techniques are applicable.

Specifically, it is possible to employ a patterning process including the steps of:

(1) forming a resist film on a substrate by using the above-described resist material;

(2) exposing the resist film to a high-energy beam; and (3) developing the exposed resist film by using a developer.

For example, the inventive resist material is applied onto a substrate (such as Si, $SiO_2$, SiN, SiON, TiN, WSi, BPSG, SOG, organic antireflective film) for manufacturing an integrated circuit or a substrate (such as Cr, CrO, CrON, $MoSi_2$, $SiO_2$) for manufacturing a mask circuit by an appropriate coating process such as spin coating, roll coating, flow coating, dip coating, spray coating, or doctor coating so that the coating film can have a thickness of 0.01 to 2 μm. The resultant is prebaked on a hot plate preferably at 60 to 150° C. for 10 seconds to 30 minutes, more preferably at 80 to 120° C. for 30 seconds to 20 minutes. In this manner, a resist film is formed.

After the step (1) and before the step (2), (1') an entire surface of the resist film can also be exposed to light having a wavelength at which the sulfonium salt of a carboxylic acid bonded to a maleimide group does not decompose. In this way, the maleimide group undergoes coupling or polymerization, so that the molecular weight of the quencher increases. Thus, the resist material exhibits properties of lower acid diffusion. In this event, the cation moiety of the sulfonium salt shown in the general formula (1) preferably does not decompose. Wavelengths at which the sulfonium salt cation does not decompose are of light having a wavelength longer than 300 nm, more preferably an i-line (365 nm), h-line (405 nm), or g-line (436 nm) of a mercury lamp having a wavelength longer than 350 nm or light irradiated from xenon lamps or LEDs in which wavelengths of 300 nm or shorter have been eliminated. The irradiation energy is within the range of 1 mJ/$cm^2$ to 1 J/$cm^2$.

Then, the resist film is exposed using a high-energy beam. Examples of the high-energy beam include ultraviolet ray, deep ultraviolet ray, EB, extreme ultraviolet ray (EUV) at a wavelength of 3 to 15 nm, X-ray, soft X-ray, excimer laser beam, γ-ray, synchrotron radiation, etc. When ultraviolet ray, deep ultraviolet ray, EUV, X-ray, soft X-ray, excimer laser beam, γ-ray, synchrotron radiation, or the like is employed as the high-energy beam, the irradiation is performed using a mask for forming a target pattern at an exposure dose of preferably about 1 to 200 mJ/$cm^2$, more preferably about 10 to 100 mJ/$cm^2$. When EB is employed as the high-energy beam, the exposure dose is preferably about 0.1 to 300 μC/$cm^2$, more preferably about 0.5 to 200 μC/$cm^2$, and the writing is performed directly or using a mask for forming a target pattern. Note that the inventive resist material is particularly suitable for fine patterning with a KrF excimer laser beam, an ArF excimer laser beam, an EB, an EUV, X-ray, soft X-ray, γ-ray, or synchrotron radiation among the high-energy beams, and is especially suitable for fine patterning with a KrF excimer laser beam, an ArF excimer laser beam, an EB, or an EUV having a wavelength of 3 to 15 nm.

The exposure may or may not be followed by PEB on a hot plate or in an oven preferably at 30 to 150° C. for 10 seconds to 30 minutes, more preferably at 50 to 120° C. for 30 seconds to 20 minutes.

In the case of a positive resist material, after the exposure or PEB, development is performed using a developer of 0.1 to 10 mass %, preferably 2 to 5 mass % alkaline aqueous solution such as tetramethylammonium hydroxide (TMAH), tetraethylammonium hydroxide (TEAH), tetrapropylammonium hydroxide (TPAH), or tetrabutylammonium hydroxide (TBAH) for 3 seconds to 3 minutes, preferably 5 seconds to 2 minutes by a conventional technique, such as dip, puddle, or spray method. Thereby, the portion irradiated with the light is dissolved by the developer, while the unexposed portion remains undissolved. In this way, the target positive pattern is formed on the substrate. A negative resist material is the reverse of the positive resist material. That is, the portion irradiated with the light is made insoluble to the developer, while the unexposed portion dissolves.

The positive resist material containing a base polymer that contains an acid-labile group can also be used to obtain a negative pattern by organic solvent development. Examples of the developer used in this event include 2-octanone, 2-nonanone, 2-heptanone, 3-heptanone, 4-heptanone, 2-hexanone, 3-hexanone, diisobutyl ketone, methylcyclohexanone, acetophenone, methylacetophenone, propyl acetate, butyl acetate, isobutyl acetate, pentyl acetate, butenyl acetate, isopentyl acetate, propyl formate, butyl formate, isobutyl formate, pentyl formate, isopentyl formate, methyl valerate, methyl pentenoate, methyl crotonate, ethyl crotonate, methyl propionate, ethyl propionate, ethyl 3-ethoxypropionate, methyl lactate, ethyl lactate, propyl lactate, butyl lactate, isobutyl lactate, pentyl lactate, isopentyl lactate, methyl 2-hydroxyisobutyrate, ethyl 2-hydroxyisobutyrate, methyl benzoate, ethyl benzoate, phenyl acetate, benzyl acetate, phenylmethyl acetate, benzyl formate, phenylethyl formate, methyl 3-phenylpropionate, benzyl propionate, phenylethyl acetate, 2-phenylethyl acetate, etc. One of these organic solvents can be used, or two or more thereof can be used in mixture.

When the development is completed, rinsing can be performed. The rinsing liquid is preferably a solvent that is miscible with the developer but does not dissolve the resist film. As such a solvent, it is preferable to use an alcohol having 3 to 10 carbon atoms, an ether compound having 8 to 12 carbon atoms, and an alkane, alkene, alkyne and aromatic solvent, each having 6 to 12 carbon atoms.

Specific examples of the alcohol having 3 to 10 carbon atoms include n-propyl alcohol, isopropyl alcohol, 1-butyl alcohol, 2-butyl alcohol, isobutyl alcohol, tert-butyl alcohol, 1-pentanol, 2-pentanol, 3-pentanol, tert-pentyl alcohol, neopentyl alcohol, 2-methyl-1-butanol, 3-methyl-1-butanol, 3-methyl-3-pentanol, cyclopentanol, 1-hexanol, 2-hexanol, 3-hexanol, 2,3-dimethyl-2-butanol, 3,3-dimethyl-1-butanol, 3,3-dimethyl-2-butanol, 2-ethyl-1-butanol, 2-methyl-1-pentanol, 2-methyl-2-pentanol, 2-methyl-3-pentanol, 3-methyl-1-pentanol, 3-methyl-2-pentanol, 3-methyl-3-pentanol, 4-methyl-1-pentanol, 4-methyl-2-pentanol, 4 methyl-3-pentanol, cyclohexanol, 1-octanol, etc.

Examples of the ether compound having 8 to 12 carbon atoms include di-n-butyl ether, diisobutyl ether, di-sec-butyl ether, di-n-pentyl ether, diisopentyl ether, di-sec-pentyl ether, di-tert-pentyl ether, di-n-hexyl ether, etc.

Examples of the alkane having 6 to 12 carbon atoms include hexane, heptane, octane, nonane, decane, undecane, dodecane, methylcyclopentane, dimethylcyclopentane, cyclohexane, methylcyclohexane, dimethylcyclohexane, cycloheptane, cyclooctane, cyclononane, etc. Examples of the alkene having 6 to 12 carbon atoms include hexene, heptene, octene, cyclohexene, methylcyclohexene, dimethylcyclohexene, cycloheptene, cyclooctene, etc. Examples of the alkyne having 6 to 12 carbon atoms include hexyne, heptyne, octyne, etc.

Examples of the aromatic solvent include toluene, xylene, ethylbenzene, isopropylbenzene, tert-butylbenzene, mesitylene, etc.

The rinsing can reduce resist pattern collapse and defect formation. Meanwhile, the rinsing is not necessarily essential, and the amount of the solvent used can be reduced by not performing the rinsing.

After the development, a hole pattern or trench pattern can be shrunk by thermal flow, RELACS process, or DSA process. A shrink agent is applied onto the hole pattern, and the shrink agent undergoes crosslinking on the resist surface by diffusion of the acid catalyst from the resist layer during baking, so that the shrink agent is attached to sidewalls of the hole pattern. The baking temperature is preferably 70 to 180° C., more preferably 80 to 170° C. The baking time is preferably 10 to 300 seconds. The extra shrink agent is removed, and thus the hole pattern is shrunk.

EXAMPLE

Hereinafter, the present invention will be described specifically with reference to Synthesis Examples, Examples, and Comparative Examples. However, the present invention is not limited to the following Examples.

The structures of the quenchers 1 to 21 and comparative quencher 1 used in resist materials are shown below.

Quencher 1
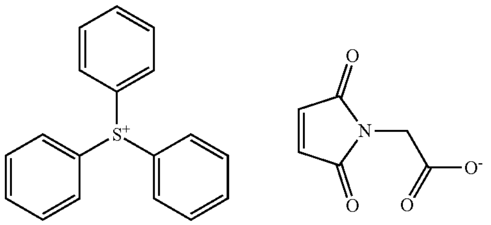
Quencher 2
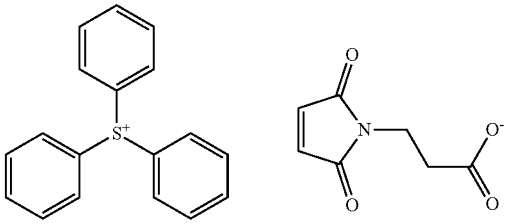
Quencher 3
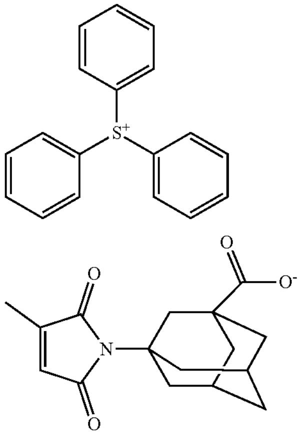
Quencher 4
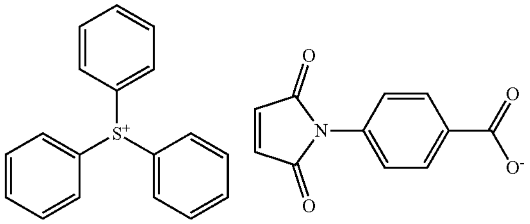
Quencher 5
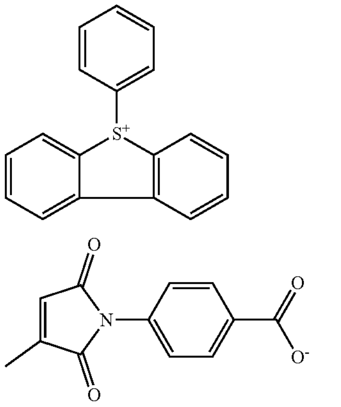
-continued
Quencher 6
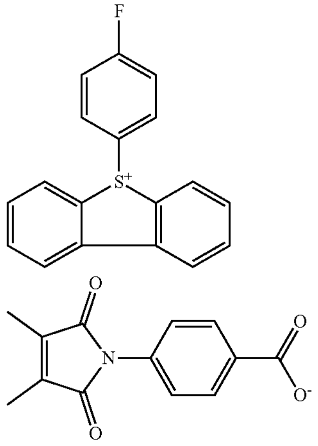
Quencher 7
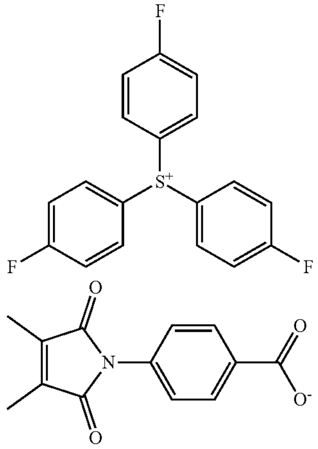
Quencher 8
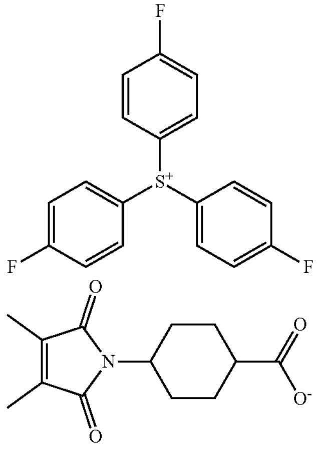
Quencher 9
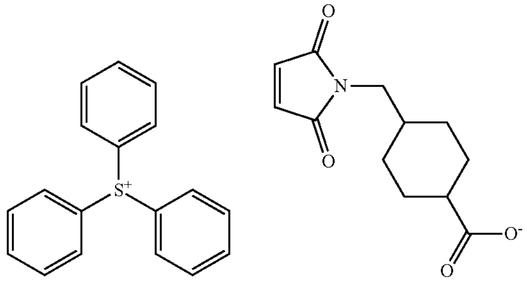

-continued
Quencher 10
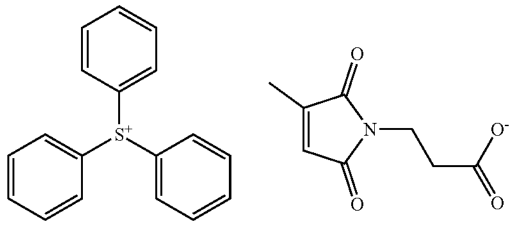
Quencher 11
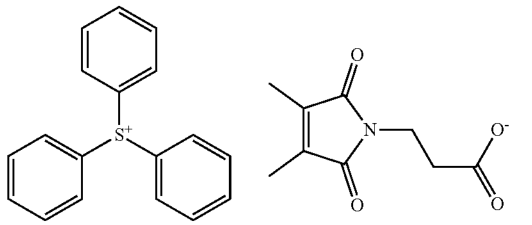
Quencher 12
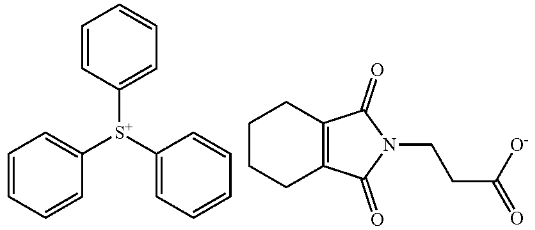
Quencher 13
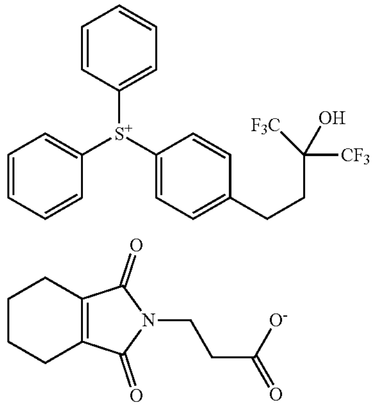
Quencher 14
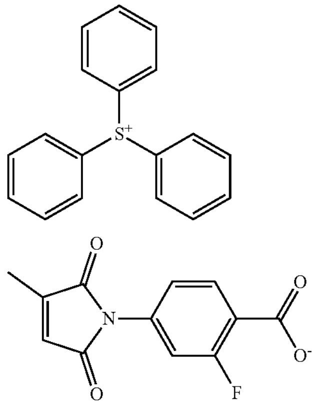
-continued
Quencher 15
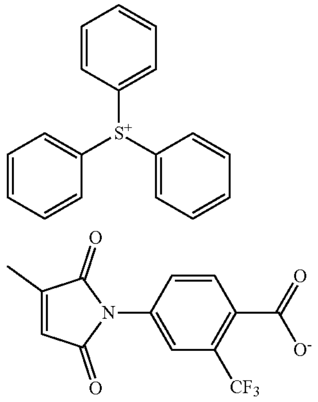
Quencher 16
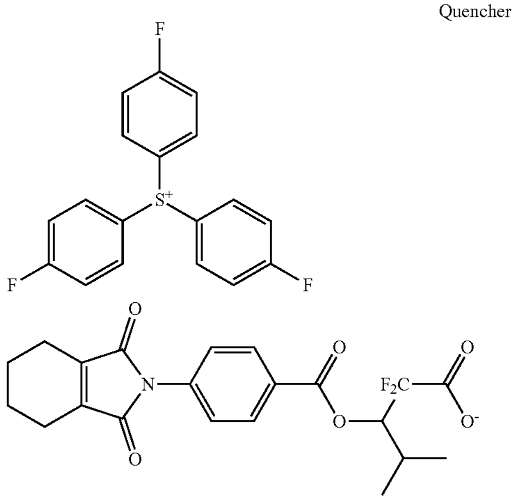
Quencher 17
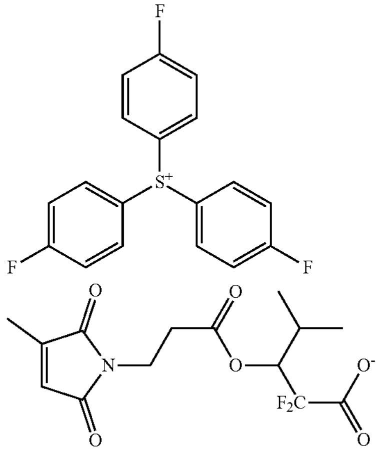
Quencher 18
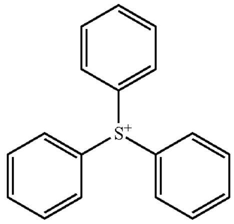

-continued

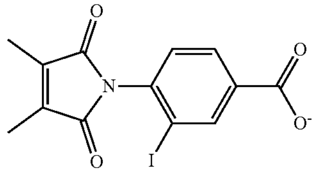

Quencher 19

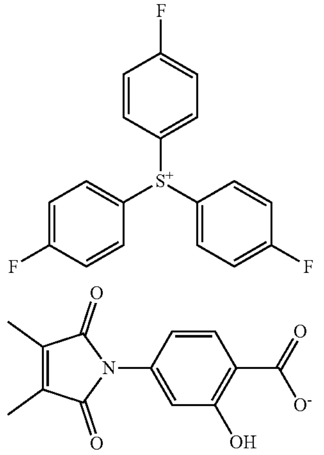

Quencher 20

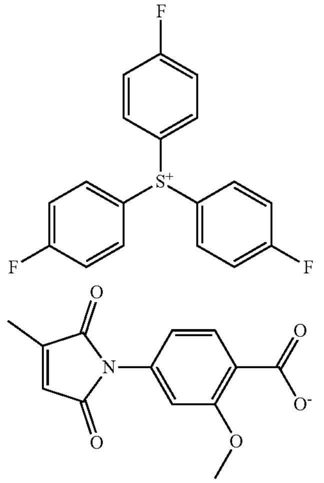

Quencher 21

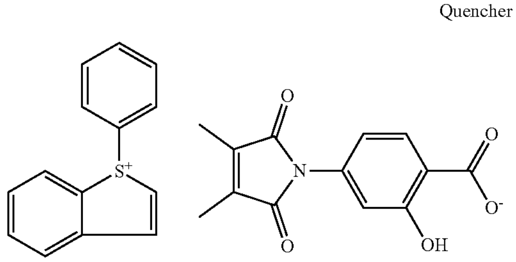

Comparative quencher 1

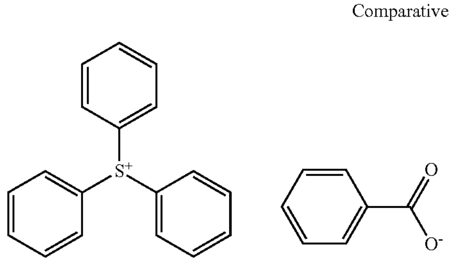

[Synthesis Example] Synthesis of Base Polymers (Polymers 1 to 5)

The monomers were combined to perform a copolymerization reaction in a solvent THF. A crystal was precipitated in methanol, furthermore, repeatedly washed with hexane, then isolated and dried to obtain a base polymer (Polymers 1 to 5) of the composition shown below. The composition of the obtained base polymer was identified by $^1$H-NMR, and the Mw and Mw/Mn were identified by GPC (solvent: THF, standard: polystyrene).

Polymer 1

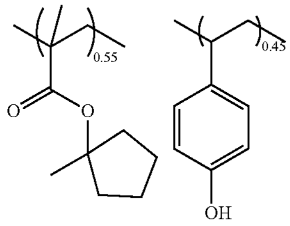

Mw = 4,700
Mw/Mn = 1.44

Polymer 2

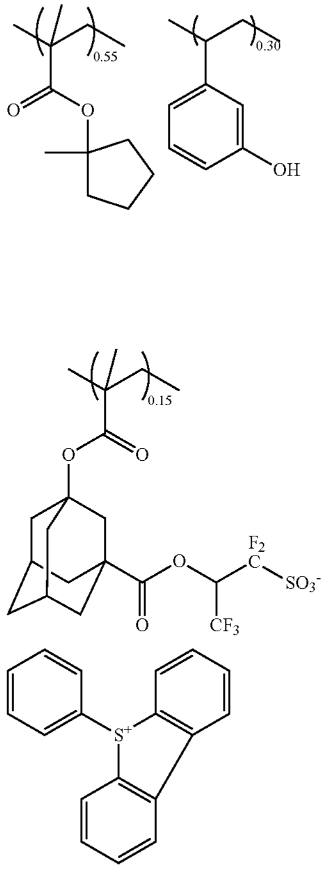

Mw = 8,900
Mw/Mn = 1.89

-continued

Polymer 3

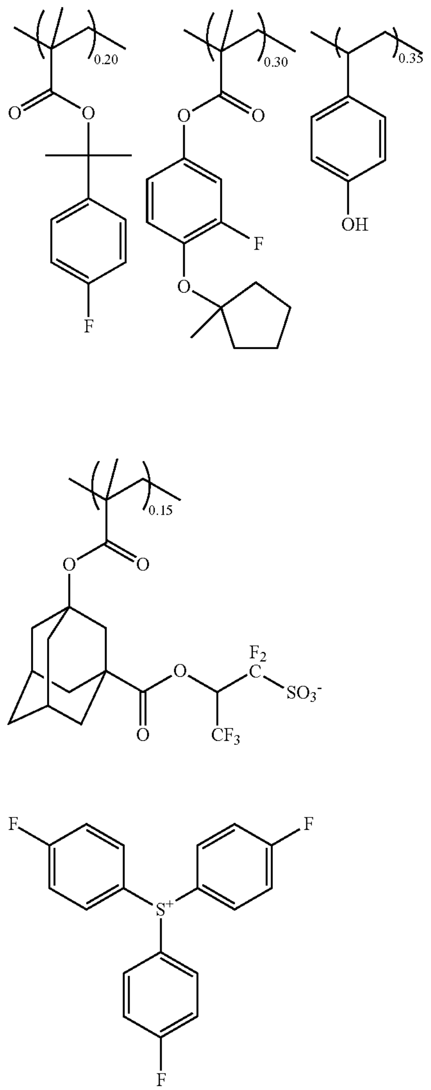

Mw = 7,800
Mw/Mn = 1.75

Polymer 4

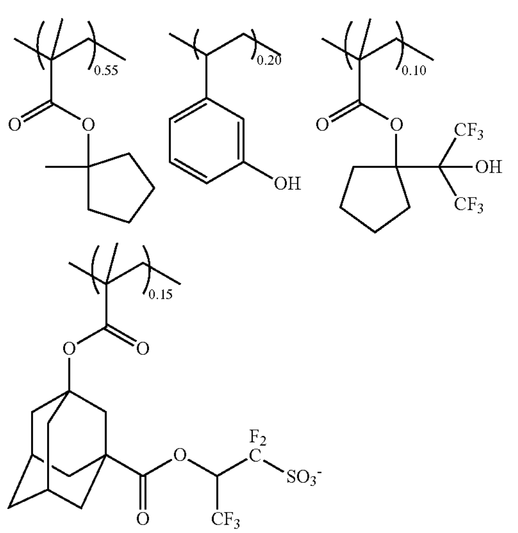

-continued

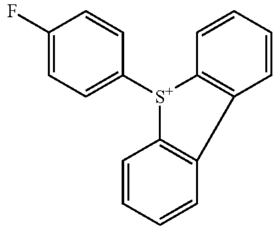

Mw = 8,300
Mw/Mn = 1.81

Polymer 5

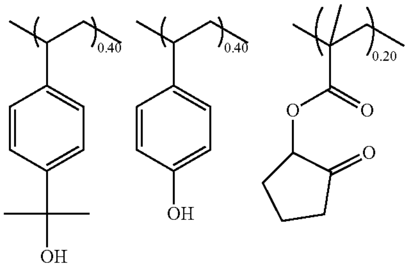

Mw = 6,900
Mw/Mn = 1.62

Examples 1 to 27, Comparative Examples 1 and 2

A solution obtained by dissolving the components in accordance with the composition shown in Tables 1 and 2 was filtered through a filter having a pore size of 0.2 μm. Thus, resist materials were prepared. The resist materials of Examples 1 to 26 and Comparative Example 1 were positive resist materials, and the resist materials of Example 27 and Comparative Example 2 were negative resist materials.

The components in Tables 1 and 2 are as follows.

Organic Solvents:

PGMEA (propylene glycol monomethyl ether acetate)

DAA (diacetone alcohol)

EL (ethyl lactate)

Acid generators: PAG 1 to 5 (see structural formulae below) and blended quencher 1, 2 (see structural formulae below)

PAG 1

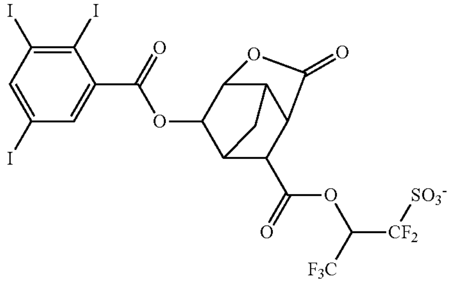

-continued

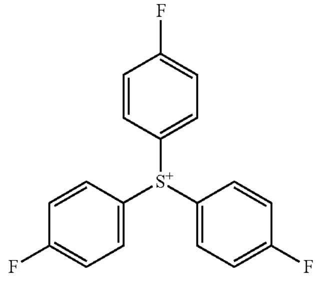

PAG 2

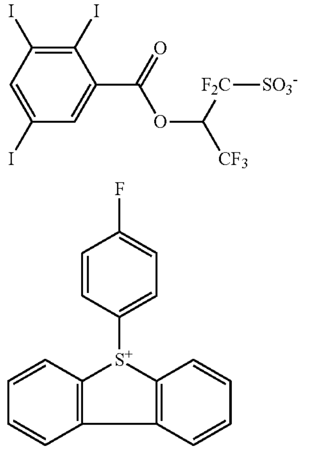

PAG 3

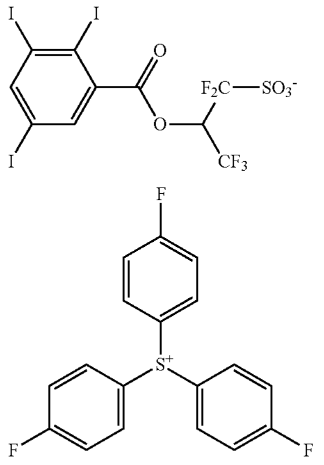

PAG 4

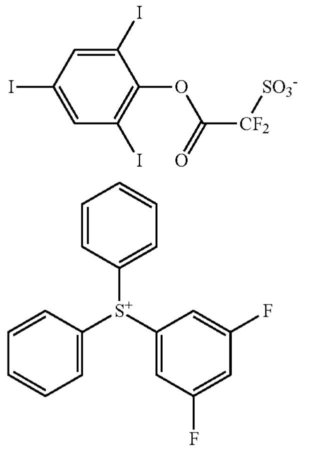

-continued

PAG 5

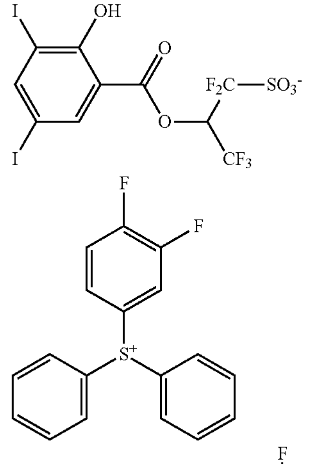

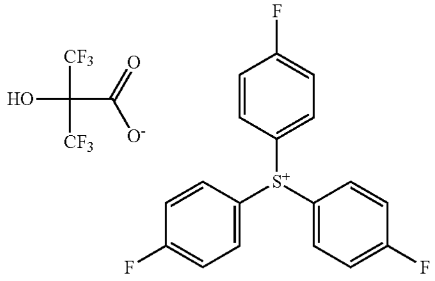

Blended quencher 1

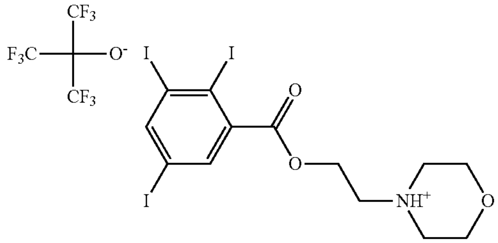

Blended quencher 2

[EUV Exposure Evaluation]

A silicon substrate with a silicon-containing spin-on hard mask SHB-A940 (silicon content: 43 mass %) manufactured by Shin-Etsu Chemical Co., Ltd. formed to have a film thickness of 20 nm was spin-coated with each resist material shown in Tables 1 and 2. The resultant was prebaked using a hot plate at 100° C. for 60 seconds to prepare a resist film having a film thickness of 50 nm. This Si substrate was exposed to an i-line on the entire surface at an exposure dose of 200 mJ/cm$^2$. Subsequently, the resist film was exposed using an EUV scanner NXE3400 (NA: 0.33, σ: 0.9/0.6, quadrupole illumination, with a mask having a hole pattern with a pitch of 44 nm and +20% bias (on-wafer size)) manufactured by ASML, followed by PEB on the hot plate at a temperature shown in Tables 1 and 2 for 60 seconds, and development with a 2.38 mass % TMAH aqueous solution for 30 seconds to obtain a hole pattern with a dimension of 22 nm in Examples 1 to 26 and Comparative Example 1, and a dot pattern with a dimension of 22 nm in Example 27 and Comparative Example 2.

Using a measurement SEM (CG6300) manufactured by Hitachi High-Technologies Corporation, an exposure dose at which the hole or dot dimension of 22 nm was formed was determined as sensitivity. In addition, the dimensions of 50 holes or dots in this event were measured, and dimensional variation (CDU, 3σ) was determined. The results are also shown in Table 1 and Table 2.

TABLE 1

| | Polymer (parts by mass) | Acid generator (parts by mass) | Quencher (parts by mass) | Organic solvent (parts by mass) | PEB temperature (° C.) | Sensitivity (mJ/cm$^2$) | CDU (nm) |
|---|---|---|---|---|---|---|---|
| Example 1 | Polymer 1 (100) | PAG1 (30) | Quencher 1 (4.17) | PGMEA (3,000) DAA (500) | 80 | 32 | 3.5 |
| Example 2 | Polymer 1 (100) | PAG2 (30) | Quencher 2 (4.31) | PGMEA (3,000) DAA (500) | 80 | 33 | 3.4 |
| Example 3 | Polymer 1 (100) | PAG2 (30) | Quencher 3 (5.51) | PGMEA (3,000) DAA (500) | 80 | 32 | 3.3 |
| Example 4 | Polymer 1 (100) | PAG2 (30) | Quencher 4 (4.79) | PGMEA (3,000) DAA (500) | 80 | 33 | 3.3 |
| Example 5 | Polymer 1 (100) | PAG2 (30) | Quencher 5 (4.91) | PGMEA (3,000) DAA (500) | 80 | 34 | 3.4 |
| Example 6 | Polymer 1 (100) | PAG2 (30) | Quencher 6 (5.23) | PGMEA (3,000) DAA (500) | 80 | 35 | 3.2 |
| Example 7 | Polymer 1 (100) | PAG2 (30) | Quencher 7 (5.61) | PGMEA (3,000) DAA (500) | 80 | 32 | 3.2 |
| Example 8 | Polymer 1 (100) | PAG2 (30) | Quencher 8 (5.67) | PGMEA (3,000) DAA (500) | 80 | 34 | 3.2 |
| Example 9 | Polymer 1 (100) | PAG3 (30) | Quencher 9 (4.99) | PGMEA (3,000) DAA (500) | 80 | 32 | 3.4 |
| Example 10 | Polymer 1 (100) | PAG3 (30) | Quencher 10 (4.45) | PGMEA (3,000) DAA (500) | 80 | 32 | 3.5 |
| Example 11 | Polymer 1 (100) | PAG3 (30) | Quencher 11 (4.59) | PGMEA (3,000) DAA (500) | 80 | 33 | 3.5 |
| Example 12 | Polymer 1 (100) | PAG3 (30) | Quencher 12 (4.85) | EL (3,000) DAA (500) | 80 | 34 | 3.4 |
| Example 13 | Polymer 1 (100) | PAG3 (30) | Quencher 13 (6.81) | EL (3,500) | 80 | 31 | 3.6 |
| Example 14 | Polymer 1 (100) | PAG3 (30) | Quencher 14 (5.11) | PGMEA (3,000) DAA (500) | 80 | 32 | 3.4 |
| Example 15 | Polymer 1 (100) | PAG3 (30) | Quencher 15 (5.61) | PGMEA (3,000) DAA (500) | 80 | 33 | 3.3 |
| Example 16 | Polymer 1 (100) | PAG3 (30) | Quencher 16 (7.37) | PGMEA (3,000) EL (500) | 80 | 34 | 3.2 |
| Example 17 | Polymer 1 (100) | PAG4 (30) | Quencher 17 (6.49) | PGMEA (3,000) EL (500) | 90 | 33 | 3.2 |
| Example 18 | Polymer 1 (100) | PAG5 (30) | Quencher 18 (6.33) | PGMEA (3,000) EL (500) | 90 | 32 | 3.4 |

TABLE 2

| | Polymer (parts by mass) | Acid generator (parts by mass) | Quencher (parts by mass) | Organic solvent (parts by mass) | PEB temperature (° C.) | Sensitivity (mJ/cm$^2$) | CDU (nm) |
|---|---|---|---|---|---|---|---|
| Example 19 | Polymer 1 (100) | PAG3 (30) | Quencher 16 (3.69) Blended quencher 1 (2.64) | PGMEA (3,000) DAA (500) | 80 | 32 | 3.1 |
| Example 20 | Polymer 1 (100) | PAG3 (30) | Quencher 16 (3.69) Blended quencher 2 (4.25) | PGMEA (3,000) DAA (500) | 80 | 34 | 3.2 |
| Example 21 | Polymer 2 (100) | — | Quencher 16 (7.37) | PGMEA (3,000) DAA (500) | 80 | 34 | 3.1 |
| Example 22 | Polymer 3 (100) | — | Quencher 16 (7.37) | PGMEA (3,000) DAA (500) | 80 | 35 | 3.0 |
| Example 23 | Polymer 3 (100) | — | Quencher 19 (5.77) | PGMEA (3,000) DAA (500) | 80 | 36 | 3.0 |
| Example 24 | Polymer 3 (100) | — | Quencher 20 (5.77) | PGMEA (3,000) DAA (500) | 80 | 34 | 3.0 |
| Example 25 | Polymer 3 (100) | — | Quencher 21 (4.71) | PGMEA (3,000) DAA (500) | 80 | 31 | 3.2 |
| Example 26 | Polymer 4 (100) | — | Quencher 16 (7.37) | PGMEA (3,000) DAA (500) | 80 | 33 | 3.1 |
| Example 27 | Polymer 5 (100) | PAG5 (20) | Quencher 1 (4.17) | PGMEA (3,000) DAA (500) | 110 | 40 | 4.0 |
| Comparative Example 1 | Polymer 1 (100) | PAG2 (30) | Comparative quencher 1 (3.84) | PGMEA (3,000) DAA (500) | 80 | 44 | 4.7 |

TABLE 2-continued

| | Polymer (parts by mass) | Acid generator (parts by mass) | Quencher (parts by mass) | Organic solvent (parts by mass) | PEB temperature (° C.) | Sensitivity ($mJ/cm^2$) | CDU (nm) |
|---|---|---|---|---|---|---|---|
| Comparative Example 2 | Polymer 5 (100) | PAG5 (20) | Comparative quencher 1 (3.84) | PGMEA (3,000) DAA (500) | 110 | 44 | 5.1 |

From the results shown in Tables 1 and 2, it was shown that the inventive resist materials, containing a sulfonium salt of a carboxylic acid bonded to a maleimide group, had high sensitivity and small CDU. It was also shown that on the contrary, the resist materials in Comparative Example 1 and Comparative Example 2, containing no sulfonium salt of a carboxylic acid bonded to a maleimide group as a quencher, had low sensitivity, and large CDU. Thus, it was revealed that the inventive resist material, containing a sulfonium salt of a carboxylic acid bonded to a maleimide group, can be used suitably as a resist material.

It should be noted that the present invention is not limited to the above-described embodiments. The embodiments are just examples, and any examples that have substantially the same feature and demonstrate the same functions and effects as those in the technical concept disclosed in claims of the present invention are included in the technical scope of the present invention.

The invention claimed is:

1. A resist material comprising a quencher, wherein the quencher contains a sulfonium salt of a carboxylic acid bonded to a maleimide group.

2. The resist material according to claim 1, wherein the sulfonium salt of the carboxylic acid bonded to the maleimide group is represented by the following general formula (1),

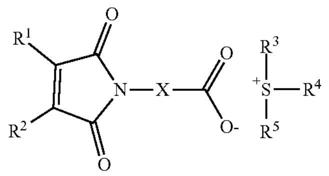

(1)

wherein $R^1$ and $R^2$ each represent a hydrogen atom, a linear alkyl group having 1 to 10 carbon atoms, a branched alkyl group having 3 to 10 carbon atoms, or a cyclic alkyl group having 3 to 10 carbon atoms, $R^1$ and $R^2$ optionally being bonded to each other to form a ring; X represents a single bond or a divalent linking group having 1 to 20 carbon atoms and optionally contains an ether group, a carbonyl group, an ester group, an amide group, a sultone group, a lactam group, a carbonate group, a halogen atom, a hydroxy group, or a carboxy group; $R^3$ to $R^5$ each independently represent a monovalent hydrocarbon group having 1 to 25 carbon atoms and optionally containing a heteroatom; and any two of $R^3$, $R^4$, and $R^5$ are optionally bonded with each other to form a ring with a sulfur atom that is bonded thereto.

3. The resist material according to claim 1, further comprising one or more selected from an acid generator for generating an acid, an organic solvent, and a surfactant.

4. The resist material according to claim 2, further comprising one or more selected from an acid generator for generating an acid, an organic solvent, and a surfactant.

5. The resist material according to claim 3, wherein the acid generator generates a sulfonic acid, imide acid, or methide acid.

6. The resist material according to claim 4, wherein the acid generator generates a sulfonic acid, imide acid, or methide acid.

7. The resist material according to claim 1, further comprising a base polymer.

8. The resist material according to claim 2, further comprising a base polymer.

9. The resist material according to claim 7, wherein the base polymer further contains at least one repeating unit selected from repeating units represented by the following general formulae (f1) to (f3), (f1)

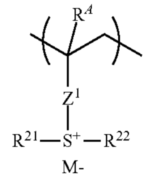

(f2)

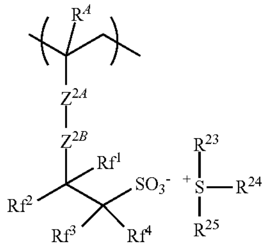

(f3)

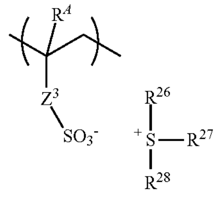

wherein each $R^A$ independently represents a hydrogen atom or a methyl group; $Z^1$ represents a single bond, a phenylene group, a naphthylene group, $-Z^{11}-$, $-O-Z^{11}-$, $-C(=O)-O-Z^{11}-$, or $-C(=O)-NH-Z^{11}-$; $Z^{11}$ represents an alkanediyl group having 1 to 6 carbon atoms, an alkenediyl group having 2 to 6 carbon atoms, or a hydrocarbon group having 1 to 20 carbon atoms and optionally containing a phenylene group and optionally contains a carbonyl group, an ester bond, an ether bond, or a hydroxy group; $Z^{2A}$ represents a single bond or an ester bond; $Z^{2B}$ represents a single bond or a divalent group having 1 to 18 carbon atoms and optionally contains an ester bond, an ether bond, a lactone ring, a bromine atom, or an iodine atom; $Z^3$ represents a single bond, a methylene group, an ethylene group, a phenylene group, a fluorinated phenylene group, a phenylene group substituted with a trifluoromethyl group, $—Z^{31}—$, $—O—Z^{31}—$, $—C({=}O)—O—Z^{31}—$, or $—C({=}O)—NH—Z^{31}—$; $Z^{31}$ represents an alkanediyl group having 1 to 15 carbon atoms, an alkenediyl group having 2 to 15 carbon atoms, or a group containing a phenylene group and optionally contains a carbonyl group, an ester bond, an ether bond, a halogen atom, or a hydroxy group; $Rf^1$ to $Rf^4$ each independently represent a hydrogen atom, a fluorine atom, an oxygen atom, or a trifluoromethyl group, provided that at least one is a fluorine atom, and that when $Rf^1$ and $Rf^2$ are respectively an oxygen atom, $Rf^1$ and $Rf^2$ are a single oxygen atom bonded to a single carbon atom to form a carbonyl group; $R^{21}$ to $R^{28}$ each independently represent a monovalent hydrocarbon group having 1 to 25 carbon atoms and optionally containing a heteroatom; any two of $R^{23}$, $R^{24}$, and $R^{25}$ or any two of $R^{26}$, $R^{27}$, and $R^{28}$ are optionally bonded with each other to form a ring with a sulfur atom that is bonded thereto; and $M^-$ represents a non-nucleophilic counter ion.

10. The resist material according to claim 8, wherein the base polymer further contains at least one repeating unit selected from repeating units represented by the following general formulae (f1) to (f3), (f1)

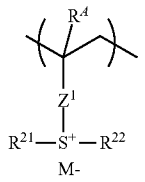

(f2)

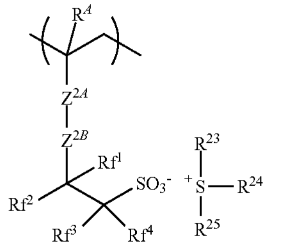

(f3)

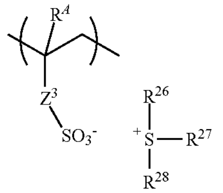

wherein each $R^A$ independently represents a hydrogen atom or a methyl group; $Z^1$ represents a single bond, a phenylene group, a naphthylene group, $—Z^{11}—$, $—O—Z^{11}—$, $—C({=}O)—O—Z^{11}—$, or $—C({=}O)—NH—Z^{11}—$; $Z^{11}$ represents an alkanediyl group having 1 to 6 carbon atoms, an alkenediyl group having 2 to 6 carbon atoms, or a hydrocarbon group having 1 to 20 carbon atoms and optionally containing a phenylene group and optionally contains a carbonyl group, an ester bond, an ether bond, or a hydroxy group; $Z^{2A}$ represents a single bond or an ester bond; $Z^{2B}$ represents a single bond or a divalent group having 1 to 18 carbon atoms and optionally contains an ester bond, an ether bond, a lactone ring, a bromine atom, or an iodine atom; $Z^3$ represents a single bond, a methylene group, an ethylene group, a phenylene group, a fluorinated phenylene group, a phenylene group substituted with a trifluoromethyl group, $—Z^{31}—$, $—O—Z^{31}—$, $—C({=}O)—O—Z^{31}—$, or $—C({=}O)—NH—Z^{31}—$; $Z^{31}$ represents an alkanediyl group having 1 to 15 carbon atoms, an alkenediyl group having 2 to 15 carbon atoms, or a group containing a phenylene group and optionally contains a carbonyl group, an ester bond, an ether bond, a halogen atom, or a hydroxy group; $Rf^1$ to $Rf^4$ each independently represent a hydrogen atom, a fluorine atom, an oxygen atom, or a trifluoromethyl group, provided that at least one is a fluorine atom, and that when $Rf^1$ and $Rf^2$ are respectively an oxygen atom, $Rf^1$ and $Rf^2$ are a single oxygen atom bonded to a single carbon atom to form a carbonyl group; $R^{21}$ to $R^{28}$ each independently represent a monovalent hydrocarbon group having 1 to 25 carbon atoms and optionally containing a heteroatom; any two of $R^{23}$, $R^{24}$, and $R^{25}$ or any two of $R^{26}$, $R^{27}$, and $R^{28}$ are optionally bonded with each other to form a ring with a sulfur atom that is bonded thereto; and $M^+$ represents a non-nucleophilic counter ion.

11. The resist material according to claim 7, wherein the base polymer contains a repeating unit represented by the following general formula (a1) or a repeating unit represented by the following formula (a2) as a repeating unit having an acid-labile group, (a1)

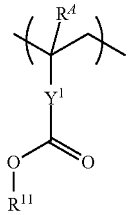

(a2)

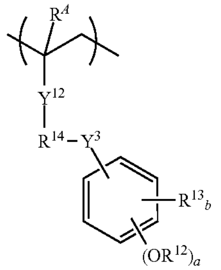

wherein each $R^A$ independently represents a hydrogen atom or a methyl group; $R^{11}$ and $R^{12}$ each represent an acid-labile group; $Y^1$ represents a single bond or a linking group having 1 to 12 carbon atoms containing at least one selected from a phenylene group, a naphthylene group, an ester bond, and a lactone ring; $Y^2$ represents a single bond, an ester bond, or an amide bond; $Y^5$ represents a single bond, an ether bond, or an ester bond; $R^{13}$ represents a fluorine atom, a trifluoromethyl group, a cyano group, or a saturated hydrocarbyl group having 1 to 6 carbon atoms; $R^{14}$ represents a single bond or an alkanediyl group having 1 to 6 carbon atoms, and some of the carbon atoms are optionally substituted with an ether bond or an ester bond; and “a” represents 1 or 2 and “b” represents an integer of 0 to 4, provided that $1 \leq a+b \leq 5$.

12. The resist material according to claim 9, wherein the base polymer contains a repeating unit represented by the following general formula (a1) or a repeating unit represented by the following formula (a2) as a repeating unit having an acid-labile group,

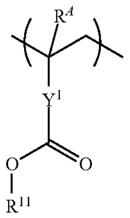
(a1)

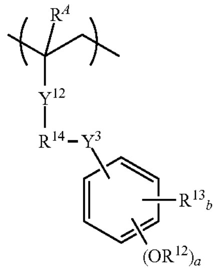
(a2)

wherein each $R^A$ independently represents a hydrogen atom or a methyl group; $R^1$ and $R^{12}$ each represent an acid-labile group; $Y^1$ represents a single bond or a linking group having 1 to 12 carbon atoms containing at least one selected from a phenylene group, a naphthylene group, an ester bond, and a lactone ring; $Y^2$ represents a single bond, an ester bond, or an amide bond; $Y^5$ represents a single bond, an ether bond, or an ester bond; $R^{13}$ represents a fluorine atom, a trifluoromethyl group, a cyano group, or a saturated hydrocarbyl group having 1 to 6 carbon atoms; $R^{14}$ represents a single bond or an alkanediyl group having 1 to 6 carbon atoms, and some of the carbon atoms are optionally substituted with an ether bond or an ester bond; and “a” represents 1 or 2 and “b” represents an integer of 0 to 4, provided that $1 \leq a+b \leq 5$.

13. The resist material according to claim 11, being a chemically amplified positive resist material.

14. The resist material according to claim 7, wherein the base polymer does not contain an acid-labile group.

15. The resist material according to claim 9, wherein the base polymer does not contain an acid-labile group.

16. The resist material according to claim 14, being a chemically amplified negative resist material.

17. A patterning process comprising the steps of:

(1) forming a resist film on a substrate by using the resist material according to claim 1;

(2) exposing the resist film to a high-energy beam; and (3) developing the exposed resist film by using a developer.

18. The patterning process according to claim 17, wherein after the step (1) and before the step (2), (1') an entire surface of the resist film is exposed to light having a wavelength at which the sulfonium salt of the carboxylic acid bonded to the maleimide group does not decompose.

19. The patterning process according to claim 18, wherein the wavelength at which the sulfonium salt does not decompose is longer than a wavelength of 300 nm.

20. The patterning process according to claim 17, wherein the high-energy beam is a KrF excimer laser beam, an ArF excimer laser beam, an electron beam, or an extreme ultraviolet ray having a wavelength of 3 to 15 nm.

* * * * *